(12) United States Patent
Farthing et al.

(10) Patent No.: US 7,358,250 B2
(45) Date of Patent: Apr. 15, 2008

(54) PYRROLO[2,3-D]PYRIMIDINES THAT MODULATE ACK1 ACTIVITY

(75) Inventors: Christopher N. Farthing, London (GB); Paul Faulder, Manchester (GB); Alexander D. Frenkel, Buxton (GB); Martin J. Harrison, Stockport (GB); Xianyun Jiao, San Mateo, CA (US); Frank Kayser, San Francisco, CA (US); David J. Kopecky, San Francisco, CA (US); Jinqian Liu, Palo Alto, CA (US); Sarah E. Lively, San Carlos, CA (US); Rajiv Sharma, Fremont, CA (US); Stephen J. Shuttleworth, Bourne End (GB)

(73) Assignee: Amgen Inc., Thousands Oaks, CA (US)

( * ) Notice: Subject to any disclaimer, the term of this patent is extended or adjusted under 35 U.S.C. 154(b) by 0 days.

(21) Appl. No.: 11/169,313

(22) Filed: Jun. 29, 2005

(65) Prior Publication Data
US 2006/0040965 A1    Feb. 23, 2006

Related U.S. Application Data

(60) Provisional application No. 60/583,682, filed on Jun. 29, 2004.

(51) Int. Cl.
| C07D 487/04 | (2006.01) |
| C07D 413/10 | (2006.01) |
| A61P 35/04 | (2006.01) |
| C07F 9/02 | (2006.01) |
| A61K 31/519 | (2006.01) |
| A61K 31/5355 | (2006.01) |
| A61K 31/675 | (2006.01) |

(52) U.S. Cl. .................. 514/234.5; 514/81; 514/265.1; 544/280; 544/117; 544/232

(58) Field of Classification Search ................ 544/280, 544/232, 117; 514/265.1, 81, 234.5, 228.5
See application file for complete search history.

(56) References Cited

U.S. PATENT DOCUMENTS

| 6,610,847 B2 | 8/2003 | Blumenkopf et al. |
| 6,627,754 B2 | 9/2003 | Blumenkopf et al. |

FOREIGN PATENT DOCUMENTS

| WO | WO 97/02266 A1 | 1/1997 |
| WO | WO 99/65908 A | 12/1999 |
| WO | WO 99/65909 A1 | 12/1999 |
| WO | WO 01/47507 A2 | 7/2001 |
| WO | WO 02/00661 A1 | 1/2002 |
| WO | WO 02/41882 A2 | 5/2002 |
| WO | WO 02/96909 A1 | 12/2002 |

OTHER PUBLICATIONS

Database Chemcats 'Online!, Chemical Abstracts Service, Columbus, Ohio (XP002353001), retrieved from STN Order Nos. (ON's): A3830/0162687, A3820/0162212 & "Chemical Block Ltd.", *Chemical Block Stock Library* catalog, Moscow, Russia, Aug. 10, 2004.

*Primary Examiner*—Brenda L. Coleman
*Assistant Examiner*—Susanna Moore
(74) *Attorney, Agent, or Firm*—Foley & Lardner LLP

(57) ABSTRACT

Compounds that modulate the action of ACK1 and LCK, and related compositions methods for treating ACK1- and LCK-mediated diseases are described. In one aspect, the compounds have the general structure:

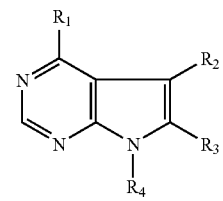

where the values of the substituents are provided herein.

22 Claims, No Drawings

PYRROLO[2,3-D]PYRIMIDINES THAT MODULATE ACK1 ACTIVITY

CROSS-REFERENCE TO RELATED APPLICATIONS

This application claims the benefit of priority of U.S. Provisional Patent Application No. 60/583,682, filed on Jun. 29, 2004.

FIELD OF THE INVENTION

This invention pertains generally to treating proliferative diseases characterized by activity of activated p21cdc42Hs-associated kinase (ACK1) and LCK. In one aspect, the present invention provides new pyrrolopyrimidine compounds, pharmaceutical formulations containing the compounds, methods of treatment using the compounds, and methods of preparing the pharmaceutical formulations and compounds.

BACKGROUND OF THE INVENTION

Cancer is the second leading cause of death in the United States, after heart disease (Boring, et al., CA Cancer J. Clin., 43:7, 1993), and it develops in one in three Americans. One of every four Americans dies of cancer. Cancer features uncontrolled cellular growth, which results either in local invasion of normal tissue or systemic spread (metastasis) of the abnormal growth. A particular type of cancer or a particular stage of cancer development may involve both elements.

Cancer is caused by inherited or acquired mutations in cancer genes, which have normal cellular functions and which induce or otherwise contribute to cancer once mutated or expressed at an abnormal level. Certain well-studied tumors carry several different independently mutated genes, including activated oncogenes and inactivated tumor suppressor genes. Each of these mutations appears to be responsible for imparting some of the traits that, in aggregate, represent the full neoplastic phenotype (Land et al., Science, 222:771, 1983; Ruley, Nature, 4:602, 1983; Hunter, Cell, 64:249, 1991).

Kinase enzymes have been shown to be important in intracellular signal transduction. One class of kinase enzymes involved in signal transduction is the Src-family of protein tyrosine kinases (PTK's), which includes, for example: Lck, Fyn(B), Fyn(T), Lyn, Src, Yes, Hck, Fgr and Blk (for review see: Bolen, J B, and Brugge, J S Annu. Rev. Immunol 1997, 15, 371). Gene disruption studies suggest that inhibition of some members of the Src family of kinases would potentially lead to therapeutic benefit. Src(–/–) mice have abnormalities in bone remodeling or osteopetrosis (Soriano, P. Cell 1991, 64, 693), suggesting that inhibition of the src kinase might be useful in diseases of bone resorption, such as osteoporosis. Lck(–/–) mice have defects in T cell maturation and activation (Anderson, S J et al. Adv. Immunol. 1994, 56, 151), suggesting that inhibition of the Lck kinase might be useful in diseases of T cell mediated inflammation. In addition, human patients have been identified with mutations effecting Lck kinase activity (Goldman, F D et al. J. Clin. Invest. 1998, 102, 421). These patients suffer from a severe combined immunodeficiency disorder (SCID).

The activated p21cdc42Hs-associated kinase (ACK1) gene encodes an intracellular, non-receptor tyrosine kinase that binds cdc42Hs in its GTP-bound form and inhibits both the intrinsic and GTPase-activating protein (GAP)-stimulated GTPase activity of p21cdc42, a Ras-like protein involved in cell growth (Manser et al., Nature 363(6427): 364-367, 1993). This binding is mediated by a unique polypeptide of 47 amino acids C-terminal to an SH3 domain. ACK1 gene contains a tyrosine kinase domain and is reported to possess tyrosine kinase activity. The protein may be involved in a regulatory mechanism that sustains the GTP-bound active form of cdc42Hs and which is directly linked to a tyrosine phosphorylation signal transduction pathway.

ACK1 is a gene that is frequently amplified and overexpressed in primary human tumors (U.S. patent application No. 20030175763). ACK1 kinase activity is regulated in the context of cell attachment and detachment, and certain cancer cells depend on ACK1's kinase activity for adhesion, anchorage independent growth and survival. Down regulation of ACK1 kinase activity or ACK1 expression levels can result in reduced tumor growth in animal models.

In addition to ACK1, other kinases have been targets for oncolytic drugs. For example, WO 01/4750782, WO 97/02266A1, and WO 02/411882A2 each disclose EGF— or VEGF-inhibiting compounds that are 5-phenyl and 6-phenyl-substituted pyrrolo[2,3-d]pyrimidines, but only in combination with 4-phenylamino or 4-benzylamino substituents. WO 99/65909A1 describes 4-piperidin-1-yl-substituted pyrrolo[2,3-d]pyrimidines that inhibit Janus Kinase 3 ("JAK3"). WO 02/096909, WO 02/00661A1, and U.S. Pat. Nos. 6,610,847B2 and 6,627,754B2 also disclose JAK3-inhibiting compounds in which the 5- and 6-positions on the pyrrolopyrimidine ring can be aryl or alkynyl; and the 4-position substituent can be of the type:

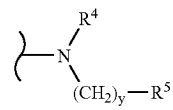

where $R^4$ can be hydrogen; y can be 0, 1, or 2; and $R^5$ is, inter alia, a substituted (C2-C9)heterocycloalkyl ring (see, e.g., the '909 and '807 publications).

Nevertheless, there remains a need for new cancer treatments. In particular, there is an especially acute need for new cancer treatments that exploit unique biochemical targets such as ACK1 and LCK. The present invention meets these and other needs.

SUMMARY OF THE INVENTION

The pyrrolopyrimidines described herein modulate the activity of tyrosine kinases such as ACK1 and LCK. Thus, in accordance with one aspect of the present invention there are provided pyrrolo[2,3-d]pyrimidine compounds useful in treating proliferative diseases such as cancer. In another aspect, there are provided pharmaceutical compositions including the pyrrolo[2,3-d]pyrimidines and methods of preparing such compositions. In still another aspect, the invention provides methods of treating animals having a proliferative disease by administering therapeutically effective amounts of pyrrolo[2,3-d]pyrimidines of the present invention to the such animals.

In a first aspect, the present invention provides compounds that are effective to inhibit or otherwise reduce the activity of ACK1. One embodiment of this aspect of the invention relates to compounds having the structure:

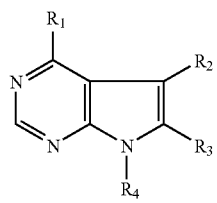

including its stereoisomers, tautomers, solvates, and pharmaceutically acceptable salts. $R_1$ is —$OR_5$, —$SR_5$, or —$NHR_5$, where $R_5$ is a (cycloheteroalkyl)alkyl or substituted (cycloheteroalkyl)alkyl moiety, wherein the cycloheteroalkyl portion of said moiety is a saturated ring. $R_2$ and $R_3$ independently are aryl, substituted aryl, heteroaryl, substituted heteroaryl, cycloalkyl, substituted cycloalkyl, cycloheteroalkyl, substituted cycloheteroalkyl, arylalkyl, substituted arylalkyl, (heteroaryl)alkyl, substituted (heteroaryl)alkyl, (cycloalkyl)alkyl, substituted (cycloalkyl)alkyl, (cycloheteroalkyl)alkyl, or substituted (cycloheteroalkyl)alkyl. $R_4$ is hydrogen, alkyl, substituted alkyl, alkylcarbonyl, substituted alkylcarbonyl, arylcarbonyl, substituted arylcarbonyl, arylalkylcarbonyl, substituted arylalkylcarbonyl, alkylsulfonyl, substituted alkylsulfonyl, arylsulfonyl, substituted arylsulfonyl, arylalkylsulfonyl, substituted arylalkylsulfonyl, trialkylsilyl, substituted trialkylsilyl, triarylalkylsilyl, substituted triarylalkylsilyl, formyl, diarylthiophosphinyl, or substituted diarylthiophosphinyl.

In some embodiments of Compound 1, $R_1$ is —$NHR_5$ defining thereby 4-(substituted amino)pyrrolo[2,3-d]pyrimidines. In more specific embodiments, $R_1$ is —$NHR_5$ and $R_2$ and $R_3$ independently are aryl, substituted aryl, heteroaryl, or substituted heteroaryl. In other embodiments, $R_5$ is (tetrahydrofuran-2-yl)methyl. In still other embodiments, $R_2$ of is phenyl defining thereby compounds of the structure:

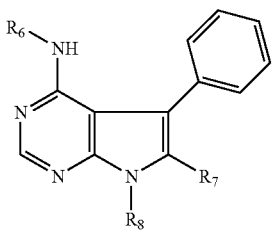

including stereoisomers thereof, tautomers thereof, solvates thereof, and pharmaceutically acceptable salts thereof. $R_6$ is a (cycloheteroalkyl)methyl moiety, wherein the cycloheteroalkyl portion of said moiety is a saturated 5- or 6-membered heteroalkyl ring containing at least one oxygen or sulfur heteroatom. $R_7$ is aryl or heteroaryl, each optionally substituted with alkylaminosulfonyl, dialkylaminosulfonyl, (heterocycloalkyl)alkylaminosulfonyl, di(alkyloxyalkyl)aminosulfonyl, alkyloxyalkylaminosulfonyl, N-morpholinosulfonyl, N-morpholinoalkylaminosulfonyl, carboxylakylaminosulfonyl, alkyloxycarbonylalkylaminosulfonyl, alkylaminocarbonyl, dialkylaminocarbonyl, (heterocycloalkyl)alkylaminocarbonyl, di(alkyloxyalkyl)aminocarbonyl, alkyloxyalkylaminocarbonyl, N-morpholinocarbonyl, N-morpholinoalkylaminocarbonyl, carboxylakylaminocarbonyl, alkyloxycarbonylalkylaminocarbonyl, cycloalkylamioncarbonyl, alkyloxy, alkylaminoalkyloxy, (dialkylamino)alkyloxy, N-morpholinoalkyloxy, or N-azacycloalkylalkyloxy, wherein each of the foregoing optional substituents is itself optionally substituted. $R_8$ is hydrogen, alkyl, substituted alkyl, alkylcarbonyl, substituted alkylcarbonyl, arylcarbonyl, substituted arylcarbonyl, arylalkylcarbonyl, arylalkylcarbonyl, substituted arylalkylcarbonyl, alkylsulfonyl, substituted alkylsulfonyl, arylsulfonyl, substituted arylsulfonyl, arylalkylsulfonyl, substituted arylalkylsulfonyl, trialkylsilyl substituted trialkylsilyl, triarylalkylsilyl, substituted triarylalkylsilyl, formyl, diarylthiophosphinyl, or substituted diarylthiophosphinyl.

In another aspect, the invention provides a method for treating an ACK1-mediated disorder in an animal, comprising administering to such animal a therapeutically effective amount of a compound described herein. In still another aspect, the invention provides a composition for treating an ACK1-mediated disorder in an animal comprising a therapeutically effective amount of a compound described herein.

These and other aspects and advantages of the invention will be apparent upon reading the following Description.

DETAILED DESCRIPTION

The present invention provides novel pyrrolo[2,3-d]pyrimidine compounds as antiproliferative agents. While not wishing to be bound by theory, it is believed that the pyrrolopyrimidines described herein act to modulate kinases involved in proliferative diseases. In particular, it is believed that the pyrrolopyrimidines modulate the activity of receptor tyrosine kinases such as ACK1 and LCK. The compounds provided herein can be formulated into pharmaceutical compositions that are useful in treating patients having tyrosine kinase-mediated disorders. Thus, in another aspect, the present invention provides methods for treating proliferative diseases such as cancer and which include administering therapeutically effective amounts of such compounds to the patients.

The following abbreviations and definitions are used throughout this application (Table 1):

TABLE 1

| | |
|---|---|
| ACK1: | Activated p21cdc42Hs-associated kinase |
| aq: | Aqueous |
| DBU: | 1,8-diazabicyclo[5.1.0]undec-7-ene |
| DCE: | Dichloroethane |
| DCM: | Dichloromethane |
| DEAD | Diethylazodicaboxylate |
| DIBALH | Diisobutylaluminum hydride |
| DIEA: | Diisopropylethylamine |
| DMA: | N,N-Dimethylacetamide |
| DMEM: | Dulbecco's modified Eagle medium |
| DMF: | N,N-Dimethylformamide |
| DMSO: | Dimethylsulfoxide |
| dppf: | 1,1'(diphenylphosphino)ferrocene |
| DTT: | Dithiothreitol |
| EDC | 1-(3-Dimethylaminopropyl)-3-ethylcarbodiimide |
| ESI | Electro Spray Ionization |
| EtOAc: | Ethyl acetate |
| EtOH: | Ethanol |
| FCS: | Fetal Calf Serum |
| g: | Gram(s) |
| h: | Hour(s) |
| HBTU: | O-Benzotriazol-1-yl-N,N,N',N'-tetramethyluronium hexafluorophosphate |
| HOBT | 1-Hydroxybenzotriazole |
| Hepes: | N-[2-Hydroxyethyl]piperazine-N'-[2-ethanesulfonic acid] |

TABLE 1-continued

| | |
|---|---|
| $IC_{50}$: | The concentration of an inhibitor that causes a 50% reduction in a measured activity. |
| LCK: | Lymphocyte specific tyrosine kinase |
| $LD_{50}$ | The concentration of an inhibitor that causes 50% mortality among tested organisms |
| LiHMDS: | Lithium bis(trimethylsilyl)amide |
| MeI: | Methyl iodide |
| MeCN: | Acetonitrile |
| MeOH: | Methanol |
| min: | Minute(s) |
| mmol: | Millimole(s) |
| NIS: | N-Iodosuccinimide |
| NMP: | 1-N-methyl-2-pyrrolidone |
| rt: | Room temperature |
| TFA: | Trifluoroacetic acid |
| THF: | Tetrahydrofuran |

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the invention. Procedures for inserting such labels into the compounds of the invention will be readily apparent to those skilled in the art based on the disclosure herein.

In general, "substituted" refers to a group as defined below in which one or more bonds to a hydrogen atom contained therein are replaced by a bond to non-hydrogen or non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfoxide groups, sulfone groups, and sulfonyl groups such as sulfonyl halides and sulfonomides; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups and others also include groups in which one or more bonds to a carbon(s) or hydrogen(s) atom is replaced by a bond to a heteroatom such as oxygen in carbonyl, carboxyl, and ester groups; and nitrogen in groups such as imines, oximes, hydrazones, and nitriles.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups, also known as cycloalkyls, as defined below. Thus, unsubstituted alkyls include primary alkyl groups, secondary alkyl groups, and tertiary alkyl groups. Unsubstituted alkyls may be bonded to one or more carbon atom(s), oxygen atom(s), nitrogen atom(s), and/or sulfur atom(s) in the parent compound. Typically, unsubstituted alkyls include straight and branched chain alkyl groups and cyclic alkyl groups having 1 to 20 carbon atoms. More typically such unsubstituted alkyl groups have from 1 to 10 carbon atoms or from 1 to 5 carbon atoms. In some embodiments, unsubstituted alkyl groups include straight and branched chain alkyl groups having from 1 to 3 carbon atoms and include methyl, ethyl, propyl, and —CH(CH$_3$)$_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfoxide groups, sulfone groups, and sulfonyl groups such as sulfone halides and sulfonamides; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. In some embodiments, substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other substituted alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted cycloalkyl" refers to cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above. Thus, typically, cycloalalkyls have from 3-20 carbon atoms, and more typically from 3-10 carbon atoms. In some embodiments, cycloalkyls have from 5-7 carbon atoms in the ring structure.

The phrase "substituted cycloalkyl" has the same meaning with respect to unsubstituted cycloalkyl groups that substituted alkyl groups have with respect to unsubstituted alkyl groups. However, a substituted cycloalkyl group also includes cycloalkyl groups in which one of the ring carbons is bonded to one of the non-carbon or non-hydrogen atoms described above and also includes cycloalkyl groups in which one or more ring carbons is bonded to a substituted and/or unsubstituted alkyl, alkenyl, or alkynyl group as defined herein. Thus, the phrase "substituted cycloalkyl" includes, but is not limited to vinylcyclohexane, and hydroxypentane among others.

The phrase "unsubstituted heteroalkyl" refers to unsubstituted alkyl groups as defined above which contain a heteroatom in place of one or more carbon atoms. For example, heteroatoms may include O, S, N, Si and P. Typically, heteroalkyl groups have 1, 2, or 3 heteroatoms or 1 or 2 heteroatoms selected from N, O, and S. For example, unsubstituted heteroalkyls include, but are not limited to, —OCH$_3$, —CH$_2$CH$_2$OCH$_3$, —OCH$_2$CH$_2$NHCH$_3$, —NHCH$_2$CH$_2$OCH$_3$, and the like.

The phrase "unsubstituted aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A typical unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g., dihydronaphthyl or tetrahydronaphthyl). Thus, the phrase "substituted aryl" includes, but is not limited to tolyl, and hydroxyphenyl among others.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

The phrase "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "unsubstituted alkynyl" refers to straight and branched chain groups such as those described with respect to unsubstituted alkyl groups as defined above, except that at least one triple bond exists between two carbon atoms. Examples include, but are not limited to —C≡CH, —C≡CCH$_3$, —C≡CCH$_2$CH$_3$, —CH$_2$C≡CH, —CH$_2$C≡CCH$_3$, and —CH$_2$C≡CCH$_2$CH$_3$ among others.

The phrase "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "unsubstituted aralkyl" refers to unsubstituted alkyl groups as defined above in which a hydrogen or carbon bond of the unsubstituted alkyl group is replaced with a bond to an aryl group as defined above. For example, methyl (—CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group). Thus the phrase includes, but is not limited to, groups such as benzyl, diphenylmethyl, and 1-phenylethyl (—CH(C$_6$H$_5$)(CH$_3$)) among others.

The phrase "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom. Examples of substituted aralkyl groups include, but are not limited to, —CH$_2$C(═O)(C$_6$H$_5$), and —CH$_2$(2-methylphenyl) among others.

The phrase "unsubstituted heterocycloalkyl" refers to saturated and unsaturated nonaromatic ring compounds including monocyclic, bicyclic, and polycyclic ring compounds containing 3 or more ring members of which one or more is a heteroatom such as, but not limited to, N, O, S, P, and Si. Typically, heterocycloalkyls contain 1-4 heteroatoms selected from N, O, and S. Although the phrase "unsubstituted heterocycloalkyl" includes bicyclic rings such as octahydro-indolyl and polycyclic rings such as quinuclidyl, it does not include heterocycloalkyl groups that have other groups such as alkyl or halo groups bonded to one of the ring members. Examples of unsubstituted heterocycloalkyl groups include, but are not limited to: unsaturated rings containing 1 to 4 nitrogen atoms such as, but not limited to dihydropyridyl; saturated rings containing 1 to 4 nitrogen atoms such as, but not limited to, pyrrolidinyl, imidazolidinyl, piperidinyl, piperazinyl; condensed heterocyclic groups containing 1 to 4 nitrogen atoms such as, but not limited to, octahydroindolyl; saturated rings containing 1 to 2 oxygen atoms such as, but not limited to, tetrahydrofuranyl; saturated rings containing 1 to 2 oxygen atoms and 1 to 3 nitrogen atoms such as, but not limited to, morpholinyl; unsaturated rings containing 1 to 3 sulfur atoms and 1 to 3 nitrogen atoms such as, but not limited to, thiazolinyl; saturated rings containing 1 to 2 sulfur atoms and 1 to 3 nitrogen atoms such as, but not limited to, thiazolodinyl; saturated and unsaturated rings containing 1 to 2 sulfur atoms such as, but not limited to, dihydrodithiinyl, dihydrodithionyl, tetrahydrothiophene, tetrahydrothiopyran; unsaturated rings containing an oxygen atom and 1 to 2 sulfur atoms such as, but not limited to, dihydrooxathiinyl; saturated rings containing 1 to 2 oxygen atoms and 1 to 2 sulfur atoms such as 1,4-oxathiane; and condensed rings containing 1 to 2 sulfur atoms such as octahydrobenzthiophene. Heterocycloalkyls also include those described above in which one or more S atoms in the ring is double-bonded to one or two oxygen atoms (sulfoxides and sulfones). For example, heterocycloalkyl groups include tetrahydrothiophene, tetrahydrothiophene oxide, and tetrahydrothiophene 1,1-dioxide. Typical heterocycloalkyl groups contain 5 or 6 ring members, such as pyrrolidinyl, piperidinyl, piperazinyl, morpholinyl, thiomorpholinyl, thiomorpholinyl in which the S atom of the thiomorpholine is bonded to one or more O atoms, tetrahydrofuranyl, dioxalanyl, dithiolanyl, dioxanyl, oxiranyl, oxathiolanyl, oxetanyl, oxazolidinyl, dithianyl, tetrahydrothiophenyl, or hexahydrothiopyranyl.

The phrase "substituted heterocycloalkyl" refers to an unsubstituted heterocycloalkyl group as defined above in which one of the ring members is bonded to a non-hydrogen atom such as described above with respect to substituted alkyl groups and substituted aryl groups. Examples include, but are not limited to, 4-methylpiperazinyl, 3-methyltetrahydrofuranyl, 1-methylpiperidinyl, and 2-chlorodihydropyridyl among others.

The phrase "unsubstituted heteroaryl" refers to monocyclic, bicyclic and polycyclic aromatic rings containing one or more heteroatoms as ring members such as N, O, and S. Thus, while the phrase encompasses condensed heteroaromatic rings such as benzimidazolyl, it does not include compounds such as 2-methylbenzimidazolyl which are substituted heteroaryl groups. Heteroaryl groups include monocyclic rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1, 2,3-triazolyl etc.), tetrazolyl, (e.g., 1H-tetrazolyl, 2H tetrazolyl, etc.); condensed heterocyclic rings containing 1 to 4 nitrogen atoms such as, but not limited to, indolyl, isoindolyl, indolinyl, indolizinyl, benzimidazolyl, quinolyl, isoquinolyl, indazolyl, benzotriazolyl; monocyclic rings containing 1 to 2 oxygen atoms and 1 to 3 nitrogen atoms such as, but not limited to, oxazolyl, isoxazolyl, oxadiazolyl (e.g., 1,2,4-oxadiazolyl, 1,3,4-oxadiazolyl, 1,2,5-oxadiazolyl, etc.); condensed heterocyclic groups containing 1 to 2 oxygen atoms and 1 to 3 nitrogen atoms, for example, benzoxazolyl, benzoxadiazolyl, benzoxazinyl (e.g., 2H-1,4-benzoxazinyl etc.); monocyclic rings containing 1 to 3 sulfur atoms and 1 to 3 nitrogen atoms such as, but not limited to, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.); monocyclic rings containing 1 to 2 sulfur atoms such as, but not limited to, thienyl, dihydrodithiinyl, dihydrodithionyl; condensed heterocyclic rings containing 1 to 2 sulfur atoms and 1 to 3 nitrogen atoms such as, but not limited to, benzothiazolyl, benzothiadiazolyl, benzothiazinyl (e.g., 2H-1,4-benzothiazinyl, etc.), dihydrobenzothiazinyl (e.g., 2H-3,4-dihydrobenzothiazinyl, etc.), monocyclic rings containing 1-2 oxygen atoms such as, but not limited to furyl; condensed heterocyclic rings containing 1 to 2 oxygen atoms such as benzodioxolyl (e.g., 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Typical heteroaryl groups contain 5 or 6 ring members or are bicyclic rings such as 5,6-fused bicyclic and 6,6-fused bicyclic groups. Thus, heteroaryl groups include pyrrolyl, imidazolyl, pyrazolyl, 1,2,3-triazolyl, 1,2,4-triazolyl, tetrazolyl, furanyl, oxazolyl, isoxazolyl, thienyl, thiazolyl, pyridinyl, benzimidazolyl, benzofuranyl, benzothiophenyl, indolyl, isoindolyl, benzoxazolyl, benzthiazolyl, quinolyl, indazolyl, purinyl, pyrimidinyl, and coumarinyl, and the like.

The phrase "substituted heteroaryl" refers to an unsubstituted heteroaryl group as defined above in which one of the ring members is bonded to a non-hydrogen atom such as described above with respect to substituted heterocycloalkyl groups and substituted aryl groups. Examples include, but are not limited to, 4-methylimidazolyl, 3-methylfuranyl, and 2-chloropyridyl among others.

The phrase "unsubstituted (heterocycloalkyl)alkyl" refers to unsubstituted alkyl groups as defined above in which a hydrogen or carbon bond of the unsubstituted alkyl group is replaced with a bond to a heterocycloalkyl group as defined above. For example, methyl (—$CH_3$) is an unsubstituted alkyl group. If a hydrogen atom of the methyl group is replaced by a bond to a heterocycloalkyl group, such as if the carbon of the methyl were bonded to carbon 2 of tetrahydrofuran (one of the carbons bonded to the 0 of the tetrahydrofuranyl) or another carbon of the tetrahydrofuranyl, then the furanylmethyl is an unsubstituted (heterocycloalkyl)alkyl group.

The phrase "substituted (heterocycloalkyl)alkyl" has the same meaning with respect to unsubstituted (heterocycloalkyl)alkyl groups that substituted aralkyl groups had with respect to unsubstituted aralkyl groups. However, a substituted (heterocycloalkyl)alkyl group also includes groups in which a non-hydrogen atom is bonded to a heteroatom in the heterocycloalkyl group of the (heterocycloalkyl)alkyl group such as, but not limited to, a nitrogen atom in the piperidine ring of a piperidinylalkyl group.

The phrase "unsubstituted (heteroaryl)alkyl" refers to unsubstituted alkyl groups as defined above in which a hydrogen or carbon bond of the unsubstituted alkyl group is replaced with a bond to a heteroaryl as defined above. For example, methyl (—$CH_3$) is an unsubstituted alkyl group. If a hydrogen atom of the methyl group is replaced by a bond to a heteroaryl group, such as if the carbon of the methyl were bonded to carbon 2 of pyridine (one of the carbons bonded to the N of the pyridine) or carbons 3 or 4 of the pyridine, then the pyridinylmethyl is an unsubstituted (heteroaryl)alkyl group.

The phrase "substituted (heteroaryl)alkyl" has the same meaning with respect to unsubstituted (heteroaryl)alkyl groups that substituted aralkyl groups had with respect to unsubstituted aralkyl groups. However, a substituted (heteroaryl)alkyl group also includes groups in which a non-hydrogen atom is bonded to a heteroatom in the heteroaryl group of the (heteroheteroaryl)alkyl group such as, but not limited to, the nitrogen atom in the an indolylalkyl group.

The phrase "substituted or unsubstituted heteroarylene" refers to a divalent substituted or unsubstituted heteroaryl as defined above. For example, if Y is (substituted or unsubstituted 5- or 6-member hetararylene)—$OR^4$, the heteroarylene group is attached both to the 6-position of the furanopyrimidine and the —$OR^4$ group.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

The instant compounds may exist as one or more stereoisomers. The various stereoisomers include enantiomers, diastereomers, atropisomers and geometric isomers. In some cases, one stereoisomer may be more active and/or may exhibit beneficial effects in comparison to other stereoisomer(s) or when separated from the other stereoisomer(s). However, it is well within the skill of the ordinary artisan to separate, and/or to selectively prepare said stereoisomers. Accordingly, "stereoisomers" of the instant invention necessarily include mixtures of stereoisomers, including racemic mixtures, individual stereoisomers, and optically active forms.

The compounds of the invention may also be solvated, especially hydrated. Hydration may occur during manufacturing of the compounds or compositions comprising the compounds, or the hydration may occur over time due to the hygroscopic nature of the compounds. Compounds of the invention may exist as organic solvates as well, including DMF, ether, and alcohol solvates among others. The identification and preparation of any particular solvate is within the skill of the ordinary artisan of synthetic organic or medicinal chemistry.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

It should be understood that certain organic compounds according to the invention may exhibit the phenomenon of tautomerism. As the chemical structures within this specification can only represent one of the possible tautomeric forms, it should be understood that the invention encompasses any tautomeric form of the drawn structure.

Certain compounds within the scope of Formula I are derivatives referred to as prodrugs or may function as prodrugs. The expression "prodrug" denotes a derivative of a direct acting drug, e.g., esters and amides, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology* 112:309-323 (1985); Bodor, N., "Novel Approaches in Prodrug Design," *Drugs of the Future* 6:165-182 (1981); and Bundgaard, H., "Design of Prodrugs: Bioreversible-Derivatives for Various Functional Groups and Chemical Entities," in *Design of Prodrugs* (H. Bundgaard, ed.), Elsevier, N.Y. (1985), Goodman and Gilmans, *The Pharmacological Basis of Therapeutics*, 8th ed., McGraw-Hill, Int. Ed. 1992.

In general, "Lck- or ACK-1-mediated disease or disease state" refers to all disease states wherein Lck and/or ACK-1 plays a role, either directly as Lck and/or ACK-1 itself, or by Lck and/or ACK-1 inducing another cytokine or disease-causing agent to be released.

In a first aspect, the present invention provides novel compositions of matter having the structure shown in Compound 1 below:

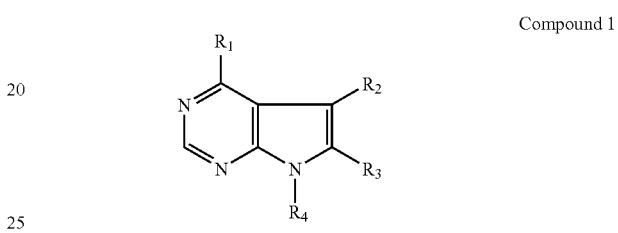

Compound 1 including its stereoisomers, tautomers, solvates, and pharmaceutically acceptable salts. $R_1$ is —$OR_5$, —$SR_5$, or —$NHR_5$, where $R_5$ is a (cycloheteroalkyl)alkyl or substituted (cycloheteroalkyl)alkyl moiety, wherein the cycloheteroalkyl portion of said moiety is a saturated ring. $R_2$ and $R_3$ independently are aryl, substituted aryl, heteroaryl, substituted heteroaryl, cycloalkyl, substituted cycloalkyl, cycloheteroalkyl, substituted cycloheteroalkyl, arylalkyl, substituted arylalkyl, (heteroaryl)alkyl, substituted (heteroaryl)alkyl, (cycloalkyl)alkyl, substituted (cycloalkyl)alkyl, (cycloheteroalkyl)alkyl, or substituted (cycloheteroalkyl)alkyl. $R_4$ is hydrogen, alkyl, substituted alkyl, alkylcarbonyl, substituted alkylcarbonyl, arylcarbonyl, substituted arylcarbonyl, arylalkylcarbonyl, substituted arylalkylcarbonyl, alkylsulfonyl, substituted alkylsulfonyl, arylsulfonyl, substituted arylsulfonyl, arylalkylsulfonyl, substituted arylalkylsulfonyl, trialkylsilyl, substituted trialkylsilyl, triarylalkylsilyl, substituted triarylalkylsilyl, formyl, diarylthiophosphinyl, or substituted diarylthiophosphinyl.

In some embodiments of Compound, $R_1$ is —$NHR_5$ defining thereby 4-(substituted amino)pyrrolo[2,3-d]pyrimidines. In more specific embodiments, $R_1$ is —$NHR_5$ and $R_2$ and $R_3$ independently are aryl, substituted aryl, heteroaryl, or substituted heteroaryl. Still more specific embodiments of Compound for which $R_1$ is —$NHR_5$ and $R_2$ and $R_3$ independently are aryl, substituted aryl, heteroaryl, or substituted heteroaryl include those wherein $R_2$ and $R_3$ independently are aryl or substituted aryl, and more specifically, those wherein $R_2$ and $R_3$ independently are phenyl or substituted phenyl; and still more specifically where $R_2$ and $R_3$ are phenyl. Other embodiments include those wherein is $R_1$ is —$NHR_5$ and $R_3$ is phenyl or substituted phenyl, and $R_2$ is phenyl. Of these compounds, still more specific embodiments include those for which $R_3$ is phenyl substituted with a moiety selected from the group consisting of: alkylaminosulfonyl, dialkylaminosulfonyl, (heterocycloalkyl)alkylaminosulfonyl, di(alkyloxyalkyl)aminosulfonyl, alkyloxyalkylaminosulfonyl, N-morpholinosulfonyl, N-morpholinoalkylaminosulfonyl, carboxylakylaminosulfonyl, alkyloxycarbonylalkylaminosulfonyl, alkylaminocarbonyl, dialkylaminocarbonyl, (heterocycloalkyl)alkylaminocarbonyl, di(alkyloxyalkyl)aminocarbonyl, alkyloxyalkylaminocarbonyl, N-morpholinocarbonyl, N-morpholinoalkylaminocarbonyl, carboxylakylaminocarbonyl, alkyloxycarbonylalkylaminocarbonyl, cycloalkylamioncarbonyl, alkyloxy, alkylaminoalkyloxy, (dialkylamino)alkyloxy, N-morpholinoalkyloxy, or N-azacycloalkylalkyloxy, wherein each of the foregoing substituents is itself optionally substituted.

In other embodiments of Compound, where $R_1$ is —$NHR_5$, $R_2$ is phenyl, and $R_3$ is phenyl substituted with a moiety selected from the group consisting of: alkylaminosulfonyl, dialkylaminosulfonyl, (heterocycloalkyl)alkylaminosulfonyl, di(alkyloxyalkyl)aminosulfonyl, alkyloxyalkylaminosulfonyl, N-morpholinosulfonyl, N-morpholinoalkylaminosulfonyl, carboxylakylaminosulfonyl, alkyloxycarbonylalkylaminosulfonyl, alkylaminocarbonyl, dialkylaminocarbonyl, (heterocycloalkyl)alkylaminocarbonyl, di(alkyloxyalkyl)aminocarbonyl, alkyloxyalkylaminocarbonyl, N-morpholinocarbonyl, N-morpholinoalkylaminocarbonyl, carboxylakylaminocarbonyl, alkyloxycarbonylalkylaminocarbonyl, cycloalkylamioncarbonyl, alkyloxy, alkylaminoalkyloxy, (dialkylamino)alkyloxy, N-morpholinoalkyloxy, or N-azacycloalkylalkyloxy, wherein each of the foregoing substituents is itself optionally substituted, $R_5$ is tetrahydrofuranylalkyl. Of these embodiments, more specific embodiments include those wherein $R_5$ is (tetrahydrofuran-2-yl)methyl.

In other embodiments of the invention, $R_2$ is phenyl (Compound 1):

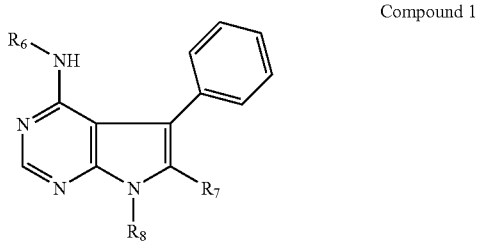

Compound 1 including stereoisomers thereof, tautomers thereof, solvates thereof, and pharmaceutically acceptable salts thereof. $R_6$ is a (cycloheteroalkyl)methyl moiety, wherein the cycloheteroalkyl portion of said moiety is a saturated 5- or 6-membered heteroalkyl ring containing at least one oxygen or sulfur heteroatom. $R_7$ is aryl or heteroaryl, each optionally substituted with alkylaminosulfonyl, dialkylaminosulfonyl, (heterocycloalkyl)alkylaminosulfonyl, di(alkyloxyalkyl)aminosulfonyl, alkyloxyalkylaminosulfonyl, N-morpholinosulfonyl, N-morpholinoalkylaminosulfonyl, carboxylakylaminosulfonyl, alkyloxycarbonylalkylaminosulfonyl, alkylaminocarbonyl, dialkylaminocarbonyl, (heterocycloalkyl)alkylaminocarbonyl, di(alkyloxyalkyl)aminocarbonyl, alkyloxyalkylaminocarbonyl, N-morpholinocarbonyl, N-morpholinoalkylaminocarbonyl, carboxylakylaminocarbonyl, alkyloxycarbonylalkylaminocarbonyl, cycloalkylamioncarbonyl, alkyloxy, alkylaminoalkyloxy, (dialkylamino)alkyloxy, N-morpholinoalkyloxy, or N-azacycloalkylalkyloxy, wherein each of the foregoing optional substituents is itself optionally substituted. $R_8$ is hydrogen, alkyl, substituted alkyl, alkylcarbonyl, substituted alkylcarbonyl, arylcarbonyl, substituted arylcarbonyl, arylalkylcarbonyl, arylalkylcarbonyl, substituted arylalkylcarbonyl, alkylsulfonyl, substituted alkylsulfonyl, arylsulfonyl, substituted arylsulfonyl, arylalkylsulfonyl, substituted arylalkylsulfonyl, trialkylsilyl substituted trialkylsilyl, triarylalkylsilyl, substituted triarylalkylsilyl, formyl, diarylthiophosphinyl, or substituted diarylthiophosphinyl.

In some embodiments of Compound 1, $R_6$ and $R_8$ retain the definitions provided, and $R_7$ is aryl. In other more specific embodiments $R_6$ and $R_8$ retain the definitions provided, and $R_7$ is phenyl. In still other embodiments of Compound 1, $R_6$ is tetrahydrofuranylmethyl, $R_7$ is phenyl, and $R_8$ retains the definition provided above. In yet more specific embodiments of Compound 1, $R_6$ is (tetrahydrofuran-2-yl)methyl, $R_7$ is phenyl, and $R_8$ retains the definition provided above. In more specific embodiments of Compound 1, $R_6$ is ((S)-tetrahydrofuran-2-yl)methyl, $R_7$ is phenyl, and $R_8$ retains the definition provided above.

Other embodiments of Compound 1 include those in which $R_6$ is tetrahydrofuranylmethyl. More specific embodiments of Compound 1 include those for which $R_6$ is (tetrahydrofuran-2-yl)methyl. Still more specific embodiments of the foregoing include those for which $R_6$ is ((S)-tetrahydrofuran-2-yl)methyl.

Compounds of the present invention can be prepared beginning with commercially available starting materials and using general synthetic techniques known to those of skill in the art. Outlined below are some reaction schemes suitable for preparing such compounds. Further exemplification is found in the specific examples provided. One of skill in the art will understand that similar methods can be used for the synthesis of the compounds.

As shown in Scheme 1, compounds of the present invention can be prepared by using a condensation reaction.

Scheme 1

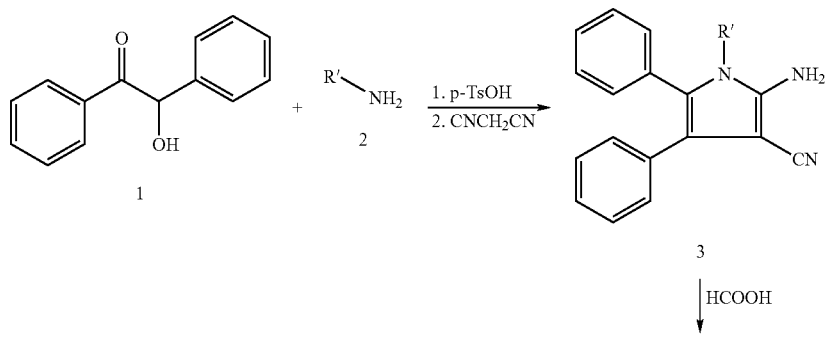

-continued

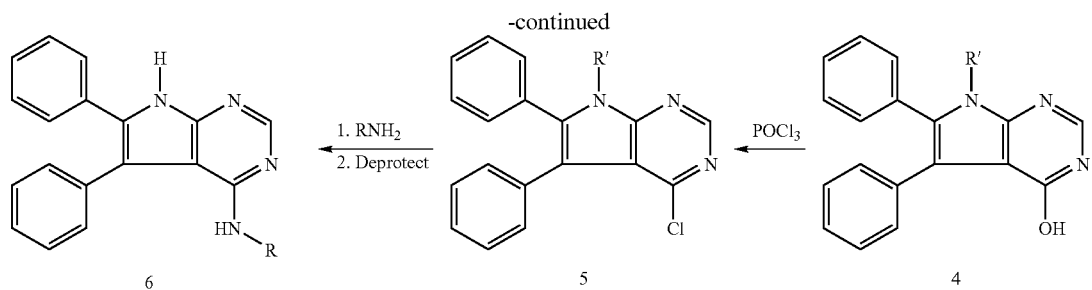

In Scheme 1, benzoin 1 is condensed with an amine 2 in a suitable organic solvent or mixture of solvents in the presence of an acid catalyst followed by addition of malononitrile to form 3 (see, e.g., H. J. Roth, K. Eger, Arch. Pharmaz. 179, (1975)). Lewis acids, such as $ZnCl_2$ or $AlCl_3$ may also be used in place of the acid catalyst. Intermediate 3 is reacted with formic acid to produce pyrrolopyrimidine 4 which can be converted into the 4-chloro derivative 5 by treatment with a chlorinating reagent such as, for example, $POCl_3$, $PCl_3$, $PCl_5$ or $SOCl_2$. Compound 5 can be treated with an amine in the presence of a base and subsequently be deprotected to provide 6. Suitable protecting groups R' are well known to those skilled in the art and include, but are not limited to, benzyl, substituted benzyl, and allyl groups. Their removal is described by sources such as Greene and Wuts, *Protecting Groups in Organic Synthesis*, 3$^{rd}$ ed., John Wiley & Sons, 1999. Those having skill in the synthetic organic and medicinal chemistry arts will understand that the phenyl groups shown in Scheme 1 can include various substituents and that the general scheme may have to be adjusted to include appropriate protection- and deprotection steps appropriate for working with different phenyl group substituents.

Reaction with a suitable alkyl halide and removal of the benzyl protecting group provides desired product 5.

Some similar alternative procedures for obtaining compounds of the present invention are shown in Schem 2 below. Here the intermediate 3 is reacted with formamide to produce pyrrolopyrimidine 7. Compound 7 may be reacted with a suitable alkylating agent such as an alkylhalide or alkyl methanesulfonate to give, after deprotection, compound 6. Compound 7 may also be acylated to give 8. For example, reaction of 7 with a carboxylic acid ($R''CO_2H$) in the presence of a coupling reagent such as 1-ethyl-3-[3-(diethylamino)propyl]carbodiimide ("EDC") and hydroxybenzotriazole ("HOBt") will accomplish such a transformation. A wide variety of conditions for such reactions are well known to those of ordinary skill in the art.

Scheme 1

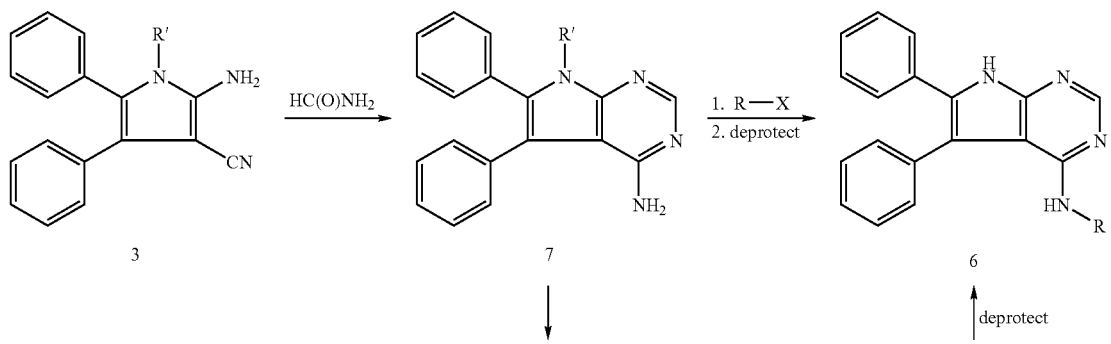

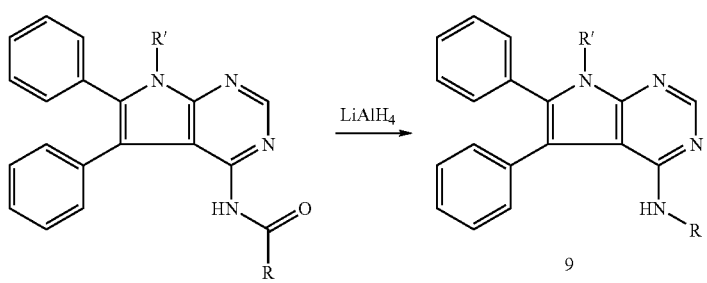

Other compounds of the present invention can be made using the synthetic approach illustrated by Scheme 3. Here, an acetylene derivative 10 is reacted with 4,6-diamino-5-iodopyrimidine 11 in the presence of a Pd catalyst to give the pyrrolopyrimidine 12. Compound 10 may be obtained by coupling an alkyl or aryl or heteroaryl halide to ethynyltrimethylsilane via a palladium mediated coupling reaction to afford (see, e.g., R. C. Larock; Comprehensive Organic Transformations, $2^{nd}$ ed., John Wiley & Sons, New York, pp. 596-599, 1999).

Palladium catalysts for such condensation reactions are well known to those skilled in the art and are produced, for example, from $Pd(OAc)_2/PPh_3$, $Pd(PPh_3)_4$, $Pd(dppf)_2Cl_2$, $Pd(PPh_3)_2Cl_2$, and many other sources (see, e.g., J. Tsuji, *Palladium Reagents and Catalysts*, John Wiley & Sons, 1997). Other metal catalysts derived from copper and nickel, for example, may also be used in addition to or in place of the palladium catalysts.

ordinary skill in the art. Reduction of the resulting amide by a reducing reagent such as $LiAlH_4$ in an appropriate organic solvent such as THF or $Et_2O$, will give the product 13. Compound 13 can be transformed into the 6-chloro, 6-bromo, or 6-iodo derivative 14 by reaction with NCS, NBS, or NIS respectively. Reaction of 15 with an arylboronic acid or arylboronic acid ester in the presence of a palladium catalyst ("Suzuki coupling") in a solvent such as, for example, DMF, DME, THF, or toluene will furnish compounds of formula 16. The preparation of arylboronic acids or arylboronic acid esters is well known to the practitioner of the art.

One of skill in the art will understand that other chemical procedures can be employed to prepare related compounds of the invention. For example, 15 can be converted to 16 via coupling with an arylzinc derivative ("Negishi coupling") or

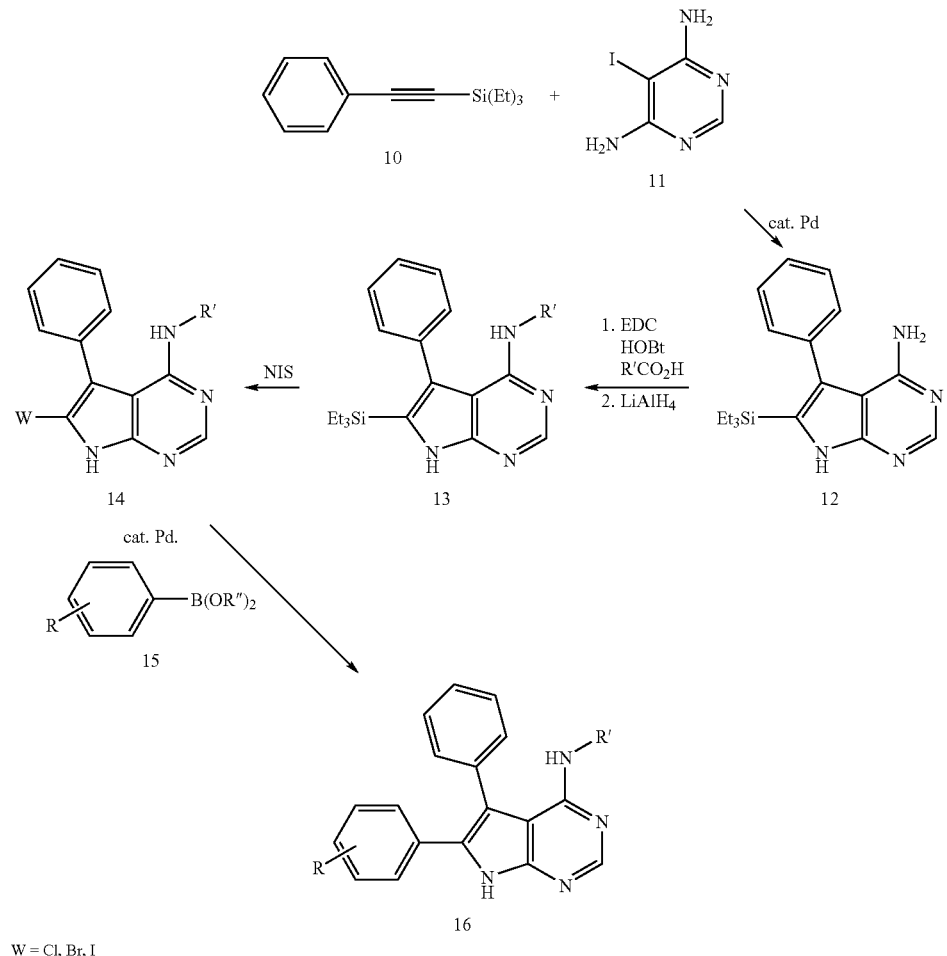

Scheme 2

W = Cl, Br, I

The intermediate 12 may be acylated, for example, by reacting 7 with a carboxylic acid chloride or a carboxylic acid ($R''CO_2H$) in the presence of a coupling reagent such as 1-ethyl-3-[3-(diethylamino)propyl]carbodiimide ("EDC") and hydroxybenzotriazole ("HOBt"). A wide variety of conditions for such reactions are well known to those of by coupling of an arylhalide in the presence of a Zn—Cu couple (see e,g., J. Tsuji, *Palladium Reagents and Catalysts*, John Wiley & Sons, 1997).

In another aspect, the invention provides a composition for treating an ACK1-mediated disorder in an animal comprising a therapeutically effective amount of a compound described herein. For example, the disorder may be mediated by the tyrosine kinase, ACK1.

"Treating" within the context of the instant invention, means an alleviation, in whole or in part, of symptoms associated with a disorder or disease, or halt of further progression or worsening of those symptoms, or prevention or prophylaxis of the disease or disorder. Similarly, as used herein, a "therapeutically effective amount" of a compound of the invention refers to an amount of the compound that alleviates, in whole or in part, symptoms associated with a disorder or disease, or halts of further progression or worsening of those symptoms, or prevents or provides prophylaxis for the disease or disorder. For example, within the context of treating patients in need of an inhibitor of ACK1, successful treatment may include a reduction in tumor adhesion and anchorage; an alleviation of symptoms related to a cancerous growth or tumor, or proliferation of diseased tissue; a halting in the progression of a disease such as cancer or in the growth of cancerous cells. Treatment may also include administering the pharmaceutical formulations of the present invention in combination with other therapies. For example, the compounds and pharmaceutical formulations of the present invention may be administered before, during, or after surgical procedure and/or radiation therapy. Alternatively, the compounds of the invention can also be administered in conjunction with other anti-proliferative agents including those used in antisense and gene therapy.

One category of suitable antiproliferative agents useful in the present invention is the alkylating agents, a group of highly reactive chemotherapeutics that form covalent linkages with nucleophilic centers (e.g., hydroxyl and carboxyl). Chemically, the alkylating agents can be divided into five groups: nitrogen mustards, ethylenimines, alkylsulfonates, triazenes, and nitrosureas. The nitrogen mustards are frequently useful in, for example, the treatment of chronic lymphocytic leukemia, Hodgkin's disease, malignant lymphoma, small cell lung cancer and breast and testicular cancer. Exemplary nitrogen mustards include chlorambucil, cyclophosphamide, ifosfamide, mechlorethamine, melphalan and uracil mustard. The ethylenimines, the most common of which is thiotepa, may be useful in bladder tumors and in breast and ovarian adenocarcinomas. The alkyl sulfonates are useful in the treatment of chronic myelogenous leukemia and other myeloproliferative disorders. Exemplary alkyl sulfonates include busulfan and piposulfan. The triazines, which include, e.g., dacarbazine, are useful in the treatment of malignant melanomas and sarcomas. Temozolomide, an analog of dacarbazine, may also be used in the methods and compositions of the present invention. Finally, the nitrosureas are especially useful against brain tumors, but also are effective for, e.g., multiple myeloma, malignant melanoma, and lymphoma. Exemplary nitrosureas include carmustine and lomustine.

Another category of antiproliferative agents suitable for use in the present invention is the antimetabolites, structural analogs of normally occurring metabolites that interfere with normal nucleic acid biosynthesis. This category of agents may be subdivided into the folic acid analogs, purine analogs and pyrimidine analogs based on the function of the metabolite with which the agent interferes. The most common folic acid analog is methotrexate, useful in the treatment of choriocarcinoma, leukemias, neoplasms and psoriasis. The purine analogs, such as mercaptopurine, thioguanine and azathioprine, may be useful in leukemias. The pyrimidine analogs are useful in the treatment of, for example, leukemia and carcinomas of the gastrointestinal tract, mammary gland, and bladder. Exemplary pyrimidine analogs include fluorouracil (5-FU), UFT (uracil and ftorafur), capecitabine, gemcitabine and cytarabine.

The vinca alkaloids, natural product-based agents that exert their cytotoxicity by binding to tubulin, represent another category of antiproliferative agents suitable for use in the present invention. The vinca alkaloids are useful in, for example, the treatment of lymphomas, leukemias, and lung, breast, testicular, bladder and head and neck cancers. Exemplary agents include vinblastine, vincristine, vinorelbine and vindesine. The taxanes, agents which promote microtubule assembly, and the podophyllotoxins, agents which inhibit topoisomerases, represent related categories of antiproliferative agents that may be useful in the methods and compositions of the present invention. Exemplary taxanes include paclitaxol and docetaxol, which are useful in breast and lung cancers, among others. Exemplary podophyllotoxins include etoposide (useful in, for example, lymphoma and Hodgkin's disease), teniposide, ironotecan (useful in, for example, colon, rectal and lung cancer) and topotecan, the latter two of which act via inhibition of topoisomerase I.

Antineoplastic antibiotics represent another category of antiproliferative agents useful in the methods and compositions of the present invention. These agents exert their effects by binding to or complexing with DNA. Exemplary agents include daunorubicin, doxorubicin, epirubicin, mitoxantrone, mitomycin, dactinomycin, plicamycin, and bleomycin. The antibiotics are useful in a diverse range of disorders, including Hodgkin's disease, leukemia, lymphoma, and lung cancer.

The methods and compositions of the present invention may comprise other antiproliferative agents, including the platinum complexes (e.g., cisplatin and carboplatin, which are especially useful in the treatment of lung, head and neck, ovarian and breast cancer); enzymes (e.g., L-asparaginase); hormone-related therapy hormone (e.g., tamoxifen, leuprolide, flutamide, megesterol acetate, diethylstilbestrol, prednisone and estradiol cypionate); hydroxyurea; methylhydrazine derivatives such as procarbazine; adrenocortical suppressants, e.g., mitotane, aminoglutethimide; aromatase inhibitors (e.g., anastrozole); and biologic response modifiers (e.g., interferon-A).

Furthermore, the methods and compositions of the present invention may comprise antiproliferative agents that result from the combination of two or more agents including, for example, prednimustine (a conjugate of prednisone and chlorambucil) and estramustine (a conjugate of nornitrogen mustard and estradiol).

The methods and compositions of the present invention may comprise a combination with another kinase inhibitor. Although the present invention is not limited to any particular kinase, kinase inhibitors contemplated for use include tyrphostin AG490 (2-cyano-3-(3,4-dihydroxyphenyl)-N-(benzyl)-2-propenamide), Iressa (ZD1839; Astra Zeneca); Gleevec (STI-571 or imatinib mesylate; Novartis); SU5416 (Pharmacia Corp./Sugen); and Tarceva (OSI-774; Roche/Genentech/OSI Pharmaceuticals).

Another embodiment of the invention relates to a method of treating arthritis, rheumatoid arthritis, psoriatic arthritis, or osteoarthritis in a mammal, the method comprising administering to the mammal a therapeutically effective amount of a compound according to any one of the above embodiments.

Thus, one embodiment of the invention relates to a method of treating organ transplant, acute transplant or heterograft or homograft rejection, or transplantation tolerance induction in a mammal, the method comprising administering to the mammal a therapeutically effective amount of a compound according to any one of the above embodiments.

Another embodiment of the invention relates to a method of treating ischemic or reperfusion injury, myocardial infarction, or stroke in a mammal, the method comprising administering to the mammal a therapeutically effective amount of a compound according to any one of the above embodiments.

Another embodiment of the invention relates to a method of treating multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal, the method comprising administering to the mammal a therapeutically-effective amount of a compound according to any one of the above embodiments.

Another embodiment of the invention relates to a method of treating colon carcinoma or thymoma in a mammal, the method comprising administering to the mammal a therapeutically-effective amount of a compound according to any one of the above embodiments.

Another embodiment of the invention relates to a method of treating a proliferative disease in a mammal, the method comprising administering to the mammal a therapeutically effective amount of a compound according to any one of the above embodiments.

Another embodiment of the invention relates to the method of treating a proliferative disease in a mammal, the method further comprising administering to the mammal a therapeutically effective amount of a second antiproliferative agent with the compound, which was administered to the mammal.

In yet other aspects, the invention provides methods for treating ACK1-and LCK-mediated disorder in an animal, comprising administering to such animal a therapeutically effective amount of a compound described herein. An "ACK1-mediated disorder" or "LCK-mediated disorder" is a disorder, disease, affliction, syndrome, or other medical condition considered to be outside the scope of normal physiological or psychological limits by one of skill in the medical arts, in which the biochemical activity of ACK1 or LCK is considered to be reasonably causally related. Non-limiting examples of ACK1-and LCK mediated disorders include proliferative diseases. Proliferative diseases include, but are not limited to, cancers of the breast, lung, pancreas, ovaries, or prostate among other organs whether benign or malignant; prostatic hyperplasia; and psoriasis. Further examples can be found in U.S. Pat. Nos. 6,713,474 and 5,792,783. A "therapeutically effective dose" as used herein is an amount of a compound of the instant invention that produces a detectable amelioration of symptoms, a reduction or cessation of further progression or worsening of those symptoms, or prevention or prophylaxis of the disorder. Similarly, "treating", within the context of the instant invention, means a detectable alleviation of symptoms associated with a disorder or disease, or a reduction or cessation of further progression or worsening of those symptoms, or prevention or prophylaxis of the disease or disorder. For example, within the context of treating patients in need of an inhibitor of ACK1 or LCK, successful treatment may include a reduction in tumor adhesion and anchorage; an alleviation of symptoms related to a cancerous growth or tumor, or proliferation of diseased tissue; a halting in the progression of a disease such as cancer or in the growth of cancerous cells. Treatment may also include administering the pharmaceutical formulations of the present invention in combination with other therapies. For example, the compounds and pharmaceutical formulations of the present invention may be administered before, during, or after surgical procedure and/or radiation therapy. The compounds of the invention can also be administered in conjunction with other anti-cancer drugs including those used in anti-sense and gene therapy.

In a more specific embodiment, the invention provides method of treating a proliferative disease comprising administering to a subject in need thereof, an effective amount of a compound having the structure:

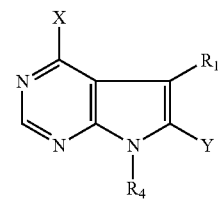

X is $OR_2$, $NR_2R_3$, or $SR_2$. Y is substituted or unsubstituted alkyl, substituted or unsubstituted cycloalkyl, substituted or unsubstituted alkenyl; substituted or unsubstituted alkynyl, substituted or unsubstituted aryl, substituted or unsubstituted aralkyl, substituted or unsubstituted heterocycloalkyl, or substituted or unsubstituted heteroaryl. $R_1$ is substituted or unsubstituted alkynyl, substituted or unsubstituted alkenyl, substituted or unsubstituted aryl, substituted or unsubstituted heterocycloalkyl, or substituted or unsubstituted heteroaryl, wherein the substituents are selected from the group consisting of F, Cl, Br, I, and $C_{1-6}$ alkyl, optionally substituted with one or more of F, Cl, Br, or I, or $C_{1-6}$ alkoxy, optionally substituted with one or more of F, Cl, Br, or I. $R_2$ and $R_3$ are independently H, substituted or unsubstituted alkyl, substituted or unsubstituted alkenyl, substituted or unsubstituted aryl, substituted or unsubstituted aralkyl, substituted or unsubstituted heterocycloalkyl; substituted or unsubstituted (heterocycloalkyl)alkyl; substituted or unsubstituted heteroaryl; or substituted or unsubstituted (heteroaryl)alkyl; or $R_2$ and $R_3$, together with the N to which they are attached, form a substituted or unsubstituted heterocycloalkyl or heteroaryl. In more specific embodiments of the method just described, X is $NHR_2$. Still more specific embodiments of this method include those wherein X is $NHR_2$ and $R_2$ is substituted or unsubstituted (heterocycloalkyl)alkyl, wherein the heterocycloalkyl group of the (heterocycloalkyl)alkyl is a saturated ring, or $R_2$ is a substituted or unsubstituted (heteroaryl)alkyl. In still more specific embodiments, the heterocycloalkyl group of the (heterocycloalkyl) alkyl or the heteroaryl group of the (heteroaryl)alkyl is tetrahydrofuranyl, furanyl, imidazolyl, dioxalanyl, dithiolanyl, dioxanyl, oxathiolanyl, oxetanyl, oxazolidinyl, dithianyl, tetrahydrothiophenyl, hexahydrothiopyranyl, piperazinyl, pyrrolidinylalkyl, morpholinyl, or thiomorpholinyl.

In another embodiment of the method, the compound described above has the structure:

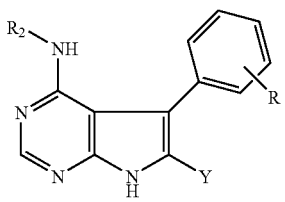

Y is substituted or unsubstituted alkyl, substituted or unsubstituted cycloalkyl, substituted or unsubstituted alkenyl; substituted or unsubstituted alkynyl, substituted or unsubstituted phenyl, substituted or unsubstituted naphthyl, (substituted or unsubstituted phenylene)-$OR_4$, substituted or unsubstituted aralkyl, substituted or unsubstituted saturated or unsaturated heterocycloalkyl, substituted or unsubstituted bicyclic heteroaryl, or (substituted or unsubstituted 5- or 6-member heteroarylene)-$OR_4$. R is H, F, Cl, Br, I, or $C_{1-6}$ alkyl, optionally substituted with one or more of F, Cl, Br, or I, or $C_{1-6}$ alkoxy, optionally substituted with one or more of F, Cl, Br, or I. A more specific embodiment is one for which Y is substituted or unsubstituted cycloalkyl, substituted or unsubstituted phenyl, substituted or unsubstituted naphthyl, (substituted or unsubstituted phenylene)-$OR_4$, substituted or unsubstituted aralkyl, substituted or unsubstituted saturated or unsaturated heterocycloalkyl, substituted or unsubstituted heteroaryl, or (substituted or unsubstituted 5- or 6-member heteroarylene)-$OR_4$.

The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

Besides those representative dosage forms described herein, pharmaceutically acceptable excipients and carriers and methods for creating therapeutically useful compositions using such are generally known to those skilled in the art of medicinal chemistry and pharmacology and are thus included in the instant invention. Such excipients, carriers, materials, and methods are described, for example, in: *Remington The Science and Practice of Pharmacy*, 20$^{th}$ Ed. (Gennaro, et al., eds.) Mack Pub. Co., New Jersey (2000); and *Pharmaceutics The Science of Dosage Form Design*, 2$^{nd}$ Ed. (Aulton, ed.) Churchill Livingstone (2002). The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or stereoisomers, solvates, prodrugs, pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, and the like may be added for oral or parenteral administration.

For nasal administration, the pharmaceutical formulations may be a spray or aerosol containing an appropriate solvent and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or a powder suitable for reconstitution as a solution. Both are prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is solid phase at room temperature but liquid phase at those temperatures suitable to release a drug inside the body, such as in the rectum. Various other agents and additives may be used in the preparation of suppositories as is well known to those of skill in the art.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. Typically, the compound or compounds of the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

EXAMPLES

The following Examples are provided to illustrate certain aspects of the present invention and to aid those of skill in the art in practicing the invention. These Examples are in no way to be considered to limit the scope of the invention in any manner.

Compound names were generated using the ChemDraw and Isis software packages.

Example 1

(5,6-Diphenyl-7H-pyrrolo[2,3-d]pyrimidin-4-yl)-(2-morpholin-4-ylethyl)-amine

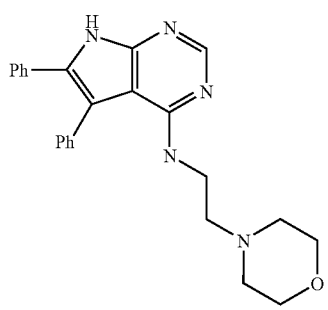

Step A: 2-Amino-1-(2,4-dimethoxybenzyl)-4,5-diphenyl-1H-pyrrole-3-carbonitrile

A solution of benzoin (6.81 g, 32.1 mmol), 2,4-dimethoxybenzylamine (5.37 g, 32.1 mmol) and p-toulene-sulfonic acid monohydrate (20 mg, cat.) in toluene (100 mL) was heated to 80° C. for 5 minutes. Malononitrile (2.12 g, 32.1 mmol) was then added and the reaction mixture was heated to reflux for 3 hours using a reflux condenser fitted with a Dean-Stark trap. The solution was then cooled, diluted with ethyl acetate (100 mL), extracted with sodium bicarbonate (conc., aq., 50 mL), hydrochloric acid (0.5N, aq., 50 mL) and water (50 mL), dried, filtered and the filtrate was concentrated under reduced pressure. Chromatography ($SiO_2$, ethyl acetate:hexane 1:2) afforded the title compound as a pale brown solid.

Step B: 7-(2,4-Dimethoxybenzyl)-5,6-diphenyl-7H-pyrrolo[2,3-d]pyrimidin-4-ylamine To a solution of 2-amino-1-(2,4-dimethoxybenzyl)-4,5-diphenyl-1H-pyrrole-3-carbonitrile in formamide (40 mL) 0.5 mL of acetic acid was added. The reaction mixture was heated to 140° C. for 3 hours, and then cooled and poured onto water (200 mL). The precipitated solid was filtered off and dried under high vacuum to give the title compound as a solid.

Step C: [7-(2,4-Dimethoxybenzyl)-5,6-diphenyl-7H-pyrrolo[2,3-d]pyrimidin-4-yl]-(2-morpholin-4-ylethyl)-amine To a solution of 7-(2,4-dimethoxybenzyl)-5,6-diphenyl-7H-pyrrolo[2,3-d]pyrimidin-4-ylamine (43.7 mg, 0.1 mmol) and sodium hydroxide powder (20 mg, 0.50 mmol) in DMF (1 mL) was added N-(2-chloroethyl)morpholine (30 mg, 0.2 mmol). The mixture was stirred for 5 minutes at 150° C. under microwave irradiation (using powerMAX™). The reaction mixture was then cooled and diluted with EtOAc (25 mL). The mixture was extracted twice with water (10 mL) and then brine. The organic layer was dried over $MgSO_4$, filtered and the filtrate was concentrated. The residue was purified by column chromatography on silica gel to give the title compound.

Step D: (5,6-Diphenyl-7H-pyrrolo[2,3-d]pyrimidin-4-yl)-(2-morpholin-4-yl-ethyl)-amine A solution of [7-(2,4-Dimethoxybenzyl)-5,6-diphenyl-7H-pyrrolo[2,3-d]pyrimidin-4-yl]-(2-morpholin-4-ylethyl)-amine (54 mg, 0.1 mmol) in 2 mL of trifluoroacetic acid was heated to reflux. After 18 hours, the solution was concentrated to dryness and purified by preparative HPLC (C8 column, water, acetonitrile, 0.1% TFA) to give the title compound. Mass Spectrum (ESI) m/e=400 (M+1).

Example 2

(5,6-Diphenyl-7H-pyrrolo[2,3-d]pyrimidin-4-yl)-(tetrahydrofuran-2-ylmethyl)-amine

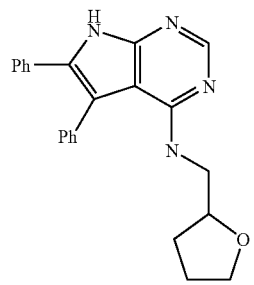

The compound was prepared using the procedures described in Example 1. $^1$H-NMR ($CDCl_3$): 1.95-1.36 (4 H, m), 3.76-3.51 (4 H, m), 3.98-3.87 (1 H, m), 5.92 (1 H, br s), 7.49-7.18 (10 H, m), 8.23 (1 H, s), 13.92 (1 H, br s). Mass Spectrum (ESI) m/e=371 (M+1).

Example 3

(5,6-Diphenyl-7H-pyrrolo[2,3-d]pyrimidin-4-yl)-(tetrahydrothiophen-2-ylmethyl)-amine

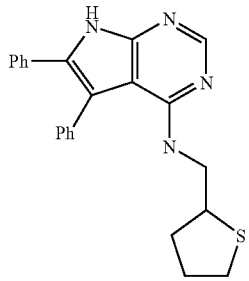

Step A: 1-Allyl-2-amino-4,5-diphenyl-1H-pyrrole-3-carbonitrile

A solution of benzoin (6.81 g, 32.1 mmol), allylamine (2 g, 35 mmol) and p-toulenesulfonic acid monohydrate (20 mg, cat.) in toluene (100 mL) was heated to 80° C. for 5 minutes. Malononitrile (2.12 g, 32.1 mmol) was then added and the reaction mixture was heated to reflux for 3 hours using a reflux condenser fitted with a Dean-Stark trap. The solution was then cooled, diluted with ethyl acetate (100 mL), extracted with sodium bicarbonate (conc., aq., 50 mL), hydrochloric acid (0.5 N, aq., 50 mL) and water (50 mL), dried, filtered and the filtrate was concentrated under reduced pressure. Chromatography ($SiO_2$, ethyl acetate: hexane 1:2) afforded the title compound as a pale brown solid.

Step B: 7-Allyl-4-chloro-5,6-diphenyl-7H-pyrrolo[2,3-d]pyrimidine

To a solution of 1-allyl-2-amino-4,5-diphenyl-1H-pyrrole-3-carbonitrile (Example 3, Step A) in 10 mL of N,N-dimethylformamide 2 mL of formic acid was added. The reaction mixture was heated to 100° C. for 2 hours, and then cooled and poured onto water (100 mL). The precipitated solid was filtered off and dried under high vacuum for 2 h. This solid was dissolved in phosphorous oxychloride (10 mL), and the reaction mixture was heated to reflux. After 1 hour, the solution was cooled and poured onto water (25 mL), and the title compound was filtered off as a brown solid. The title compound was used without further purification in subsequent reactions.

Step C: (7-Allyl-5,6-diphenyl-7H-pyrrolo[2,3-d]pyrimidin-4-yl)-(tetrahydrothiophen-2-ylmethyl)-amine To a solution of 7-allyl-4-chloro-5,6-diphenyl-7H-pyrrolo [2,3-d]pyrimidine (Example 3, Step B; 200 mg, 0.58 mmol) and 140 mg of (tetrahydrothiophen-2-yl)methylamine (1.20 mmol) in N,N-dimethylformamide (3 mL) was added potassium carbonate (200 mg, 1.45 mmol). The mixture was stirred for 5 minutes at 120° C. under microwave irradiation (using powerMAX™). The reaction mixture was then cooled and diluted with EtOAc (25 mL). The mixture was extracted twice with water (10 mL) and then brine. The organic layer was dried over $MgSO_4$, filtered and the filtrate was concentrated. The residue was purified by preparative HPLC (C8 column, water, acetonitrile, 0.1% TFA) to give the title compound.

Step D: (5,6-Diphenyl-7H-pyrrolo[2,3-d]pyrimidin-4-yl)-(tetrahydrothiophen-2-ylmethyl)-amine To a solution of (7-allyl-5,6-diphenyl-7H-pyrrolo[2,3-d] pyrimidin-4-yl)-(tetrahydrothiophen-2-ylmethyl)-amine (Example 3, Step C, 0.20 mmol) in DMSO (1 mL) was added potassium tert-butoxide (50 mg, 0.45 mmol) and the solution was heated to 110° C. for 24 hours. The solution was then cooled, diluted with ethyl acetate, extracted with water (2×25 mL), dried and concentrated under reduced pressure. Acetone (1 mL) was then added, followed by sulfuric acid (1 N, aq., 1 mL) and mercury (II) chloride (250 mg, 1 mmol). The reaction mixture was heated to reflux for 4 hours, cooled, and purified by preparative HPLC (C8 column, water, acetonitrile, 0.1% TFA) to give the title compound. $^1$H-NMR (CDCl$_3$): 1.95-1.39 (4 H, m), 2.78-2.57 (2 H, m), 3.75-3.42 (4 H, m), 5.91 (1 H, br s), 7.43-7.02 (10 H, m), 8.20 (1 H, s), 13.87 (1 H, br s). Mass Spectrum (ESI) m/e=387 (M+1).

Example 4

(5,6-Diphenyl-7H-pyrrolo[2,3-d]pyrimidin-4-yl)-(tetrahydropyran-2-ylmethyl) amine

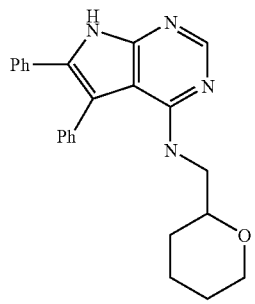

The compound was prepared using the procedure described in Example 3 using the appropriate amine: $^1$H-NMR (CDCl$_3$): 1.82-1.08 (6 H, m), 3.76-3.66 & 3.28-3.15 (2H & 3 H, 2×m), 6.03 (1 H, br s), 7.42-7.18 (10 H, m), 8.20 (1 H, s), 13.78 (1 H, br s). Mass Spectrum (ESI) m/e=385 (M+1).

Example 5

N,N-Dimethyl-4-{5-phenyl-4-[(tetrahydro-furan-2-ylmethyl)-amino]-7H-pyrrolo[2,3-d]pyrimidin-6-yl}-benzenesulfonamide

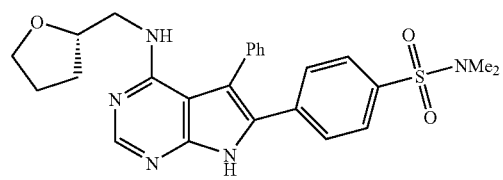

Step A: 4-Iodo-N,N-dimethyl-benzenesulfonamide

A mixture of 1.20 g (3.9 mmol) of pipsyl chloride in 10 ml chloroform and 60 ml saturated aqueous sodium bicarbonate was stirred at room temperature for 21 h. The reaction mixture was extracted with chloroform (15 ml) and the organic layer was washed with water (1×), dried over Na$_2$SO$_4$ and filtered to give the title compound. The crude product was carried on directly into the subsequent step. $^1$H-NMR (CDCl$_3$) δ 2.71 (s, 6 H), 7.47 (d, J=8.6 Hz, 2 H), 7.90 (d, J=8.6 Hz, 2 H). Mass Spectrum (ESI) m/e=312.0 (M+1), 644.7 (2M+23).

Step B: N,N-Dimethyl-4-(4,4,5,5-tetramethyl-[1,3,2]dioxaborolan-2-yl)-benzenesulfonamide A mixture of 983 mg (9.6 mmol) of KOAc, 82 mg (0.10 mmol) of Pd(dppf)$_2$Cl$_2$.CH$_2$Cl$_2$ and 950 mg (98%, 3.7 mmol) of bis(pinacolato)diboron was purged with nitrogen for 2 min. In a separate flask, 1.04 g (3.3 mmol) of 4-iodo-N,N-dimethyl-benzenesulfonamide was purged with nitrogen for 2 min and then was dissolved in 20 ml DMSO. This solution was added to the solids in the first flask, and the resulting orange slurry was heated to 80° C. for 17 h. The reaction mixture was diluted with benzene (100 ml) and washed with water (60 ml). The aqueous layer was extracted with more benzene (1×). The combined organic layers were dried over Na$_2$SO$_4$, filtered, and the filtrate was concentrated and purified by chromatography on silica gel (hexanes:EtOAc, 17:3) to give the title compound. $^1$H-NMR (CDCl$_3$) δ 1.36 (s, 12 H), 2.69 (s, 6 H), 7.75 (d, J=8.1 Hz, 2 H), 7.97 (d, J=8.0 Hz, 2 H). Mass Spectrum (ESI) m/e=312.1 (M+1).

Step C: 5-Phenyl-6-(triethylsilyl)-7-H-pyrrolo[2,3-d]pyrimidin-4-ylamine

To a slurry of 2.50 g (10.6 mmol) of 5-iodo-4,6-diaminopyrimidine, 450 mg (10.6 mmol) of LiCl, 2.25 g (21.2 mmol) of Na$_2$CO$_3$ and 870 mg (1.1 mmol) of Pd(dppf)$_2$Cl$_2$.CH$_2$Cl$_2$ in 20 ml DMF was slowly added 5.73 g (26.5 mmol) of 1-phenyl-2-(trimethylsilyl)acetylene. The reaction mixture was warmed to 95° C. and stirred for 14 h. The reaction was cooled to room temperature and dichloromethane (250 ml) was added. The mixture was washed with saturated aqueous sodium bicarbonate (1×) and brine (1×). The organic layer was dried over Na$_2$SO$_4$, filtered and the filtrate was concentrated. The residue was purified by chromatography on silica gel (hexanes:EtOAc, 1:1 grading to hexanes:EtOAc, 0:1) to give the title compound. $^1$H-NMR (400 MHz, DMSO-d$_6$) δ 0.57 (q, J=7.6 Hz, 6 H), 0.79 (t, J=7.6 Hz, 9 H), 5.54 (br, 2 H), 7.37-7.48 (m, 5 H), 8.09 (s, 1 H), 11.45 (s, 1 H). Mass Spectrum (m/e)=325.1 (M+1).

Step D: (S)-[5-Phenyl-6-(triethylsilanyl)-7-H-pyrrolo[2,3-d]pyrimidine-4-yl]-(tetrahydrofuran-2-ylmethyl)-amine To a slurry of 4.00 g (12.3 mmol) of 5-phenyl-6-(triethylsilyl)-7-H-pyrrolo[2,3-d]pyrimidin-4-amine, 3.10 g (16.0 mmol) of EDC and 2.50 g (18.5 mmol) of HOBt and catalytic DMAP in 20 ml DMF was added dropwise 1.91 g (14.8 mmol) of (S)-tetrahydro-2-furoic acid at 0° C. The reaction mixture was stirred at 0° C. for 1 h, then was warmed to room temperature and stirred for 30 h. Dichloromethane (500 ml) was added and the mixture was washed with brine (1×), saturated aqueous sodium bicarbonate (1×), and brine (1×). The organic layer was dried over Na$_2$SO$_4$ and filtered. The crude amide was dissolved in 20 ml THF and added to a solution of 700 mg (27.1 mmol) of lithium aluminum hydride in 40 ml THF at 0° C. The slurry was warmed to room temperature and stirred for 1 h, and then to 50° C. and stirred for an additional 2 h. The reaction mixture was cooled to room temperature and poured into ice water. The aqueous material was extracted with ethyl acetate (4×). The combined organic layers were washed with brine (1×), dried over Na$_2$SO$_4$, filtered and purified by chromatography on silica gel (EtOAc:MeOH:Et$_3$N, 9:1:0.1) to give the title compound. $^1$H-NMR (400 MHz, CDCl$_3$)δ, 0.61 (q, J=7.6 Hz, 6 H), 0.89 (t, J=7.6 Hz, 9 H), 1.48 (m, 1 H), 1.69-1.85 (m, 3 H), 3.59-3.62 (m, 4 H), 3.94 (m, 1 H), 5.03 (s, 1 H), 7.28 (m, 3 H), 7.45 (m, 2 H), 8.33 (s, 1 H), 8.68 (s, 1 H). Mass Spectrum (ESI) m/e=409.1 (M+1).

Step E: (S)-[6-Iodo-5-phenyl-7H-pyrrolo[2,3-d]pyrimidin-4-yl]-(tetrahydrofuran-2-ylmethyl)amine A solution of 1.00 g (2.5 mmol) of (S)-[5-phenyl-6-(triethylsilanyl)-7-H-pyrrolo[2,3-d]pyrimidine-4-yl]-(tetrahydrofuran-2-ylmethyl)-amine and 830 mg (3.7 mmol) of N-iodosuccinimide in 10 ml DMF was stirred at 45° C. for 1 h. The reaction mixture was partitioned between dichloromethane (120 ml) and a 4:1 mixture of brine and saturated aqueous sodium thiosulfate (35 ml). The organic layer was washed with saturated aqueous sodium bicarbonate (1×) and brine (1×), dried over Na$_2$SO$_4$, filtered and concentrated. The residue was dissolved in dichloromethane (10 ml), and hexanes (200 ml) was added slowly. A solid precipitate formed. The solid was filtered off and dried under high vacuum to give the title compound. $^1$H-NMR (400 MHz, CDCl$_3$) δ 1.51 (m, 1 H), 1.69-1.91 (m, 3 H), 3.19-3.69 (m, 4 H), 3.99 (m, 1 H), 5.27 (t, J=4.4 Hz, 1 H), 7.37-7.56 (m, 5 H), 8.42 (s, 1 H), 13.21 (s, 1 H). Mass Spectrum (ESI) m/e=421.0 (M+1).

Step F. N,N-Dimethyl-4-{5-phenyl-4-[(tetrahydrofuran-2-ylmethyl)-amino]-7H-pyrrolo[2,3-d]pyrimidin-6-yl}-benzenesulfonamide A mixture of 100 mg (0.2 mmol) of (S)-(6-iodo-5-phenyl-7H-pyrrolo[2,3-d]pyrimidin-4-yl)-(tetrahydrofuran-2-ylmethyl)-amine, 110 mg (0.4 mmol) of NN-dimethyl-4-(4,4,5,5-tetramethyl-[1,3,2]dioxaborolan-2-yl)-benzenesulfonamide (Example 5, Step B), 32 mg (0.8 mmol) of LiCl, 20 mg (0.02 mmol) of Pd(dppf)$_2$Cl$_2$.CH$_2$Cl$_2$ and 300 μl (0.6 mmol) of 2 M aqueous sodium carbonate solution in 3 ml toluene and 3 ml ethanol was purged with nitrogen for 2 min. The brown slurry was heated to 80° C. for 15 h and then was concentrated. The residue was purified by HPLC (Capcell Pak C$_{18}$ 5 μm, gradient of 80% A:20% B to 20% A:80% B over 45 min; A=0.5% TFA in water, B=0.5% TFA in acetonitrile) to give the title compound. $^1$H-NMR (DMSO-d$_6$) δ 1.31-1.42 (m, 1 H), 1.56-1.87 (m, 3 H), 2.59 (s, 6 H), 3.46-3.56 (m, 4 H), 3.82-3.91 (m, 1 H), 5.48 (s, 1 H), 7.37 (s, 1 H), 7.38-7.43 (m, 2 H), 7.50-7.58 (m, 4 H), 7.65 (d, J=8.6 Hz, 2 H), 8.34 (s, 1 H), 12.82 (br s, 1 H). Mass Spectrum (ESI) m/e=478.0 (M+1).

The compounds in the following table were made using the method described in Example 5 above:

TABLE

| Example | R |
|---------|---|
| 6 | SO$_2$NHMe |
| 7 | SO$_2$NEt$_2$ |
| 8 | (morpholine-substituted sulfonamide group) |

TABLE-continued

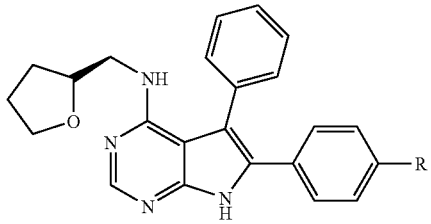

| Example | R |
|---------|---|
| 9 | 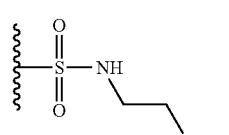 |
| 10 | 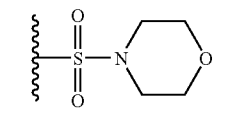 |
| 11 | 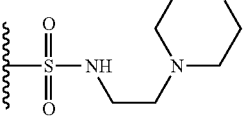 |
| 12 | 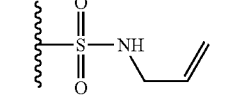 |
| 13 | 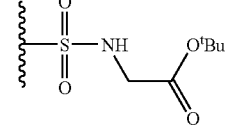 |
| 14 | 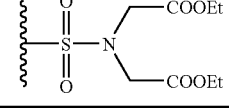 |

Example 6

N-Methyl-4-{5-phenyl-4-[(tetrahydrofuran-2-ylmethyl)-amino]-7H-pyrrolo[2,3-d]pyrimidin-6-yl}-benzenesulfonamide

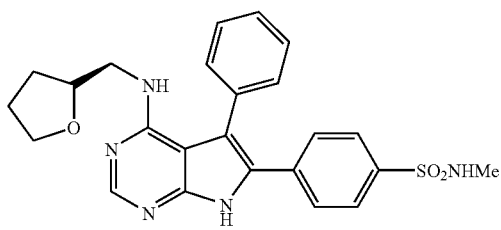

$^1$H-NMR (DMSO-d$_6$) δ 1.30-1.41 (m, 1 H), 1.56-1.86 (m, 3 H), 2.41 (s, 3 H), 3.43-3.58 (m, 4 H), 3.80-3.89 (m, 1 H), 4.98-5.04 (m, 1 H), 7.37-7.53 (m, 8 H), 7.63 (d, J=8.6 Hz, 2 H), 8.22 (s, 1 H), 12.35 (br s, 1 H). Mass Spectrum (ESI) m/e=464.0 (M+1).

Example 7

N,N-Diethyl-4-{5-phenyl-4-[(tetrahydrofuran-2-ylmethyl)-amino]-7H-pyrrolo[2,3-d]pyrimidin-6-yl}-benzenesulfonamide

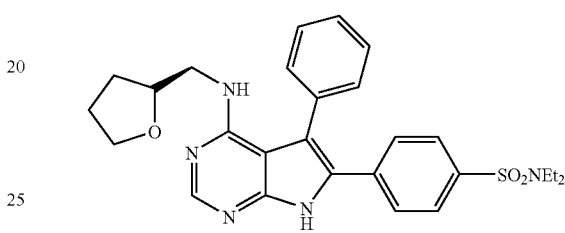

$^1$H-NMR (DMSO-d$_6$) δ 1.02 (t, J=6.8 Hz, 6 H), 1.31-1.40 (m, 1 H), 1.$^{58}$-1.87 (m, 3 H), 3.14 (q, J=6.8 Hz, 4 H), 3.47-3.58 (m, 4 H), 3.82-3.91 (m, 1 H), 5.43-5.51 (m, 1 H), 7.33-7.42 (m, 3 H), 7.47-7.53 (m, 4 H), 7.69 (d, J=8.6 Hz, 2 H), 8.33 (s, 1 H), 12.77 (br s, 1 H). Mass Spectrum (ESI) m/e=506.0 (M+1).

Example 8

N,N-Bis-(2-methoxyethyl)-4-{5-phenyl-4-[(tetrahydrofuran-2-ylmethyl)-amino]-7H-pyrrolo[2,3-d]pyrimidin-6-yl}-benzenesulfonamide

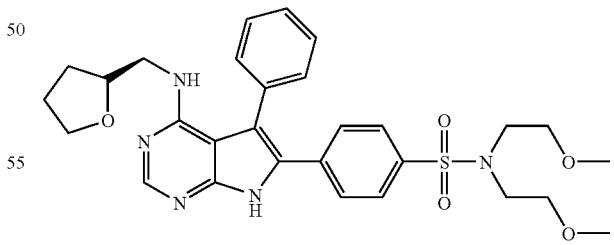

$^1$H-NMR (CDCl$_3$) δ 1.45-1.54 (m, 1 H), 1.63-1.93 (m, 3 H), 3.27 (s, 6 H), 3.41-3.68 (m, 12 H), 3.91-4.00 (m, 1 H), 5.22-5.29 (m, 1 H), 7.41-7.52 (m, 5 H), 7.55 (d, J=8.5 Hz, 2 H), 7.77 (d, J=8.5 Hz, 2 H), 8.30 (s, 1 H), 13.38 (br s, 1 H). Mass Spectrum (ESI) m/e=566.0 (M+1).

Example 9

N-(2-Methoxyethyl)-4-{5-phenyl-4-[(tetrahydrofuran-2-ylmethyl)-amino]-7H-pyrrolo[2,3-d]pyrimidin-6-yl}-benzenesulfonamide

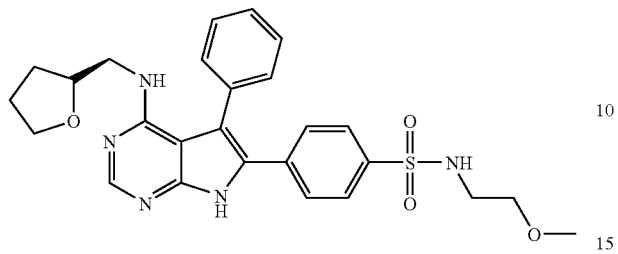

$^1$H-NMR (DMSO-$d_6$) δ 1.30-1.41 (m, 1 H), 1.58-1.87 (m, 3 H), 2.88-2.95 (m, 2 H), 3.11 (s, 3 H), 3.27 (t, J=5.7 Hz, 2 H), 3.47-3.57 (m, 4 H), 3.83-3.91 (m, 1 H), 5.40-5.51 (m, 1 H), 7.35-7.42 (m, 3 H), 7.46-7.54 (m, 4 H), 7.68 (d, J=8.5 Hz, 2 H), 7.73 (t, J=5.9 Hz, 1 H), 8.33 (s, 1 H), 12.75 (br s, 1 H). Mass Spectrum (ESI) m/e=508.0 (M+1).

Example 10

{6-[4-(Morpholin-4-sulfonyl)-phenyl]-5-phenyl-7H-pyrrolo[2,3-d]pyrimidin-4-yl}-(tetrahydrofuran-2-ylmethyl)-amine

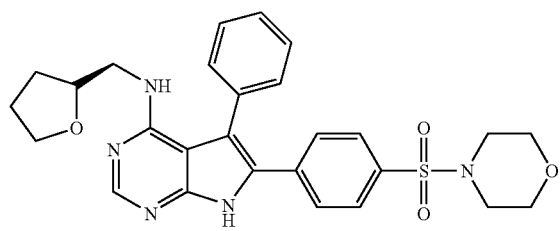

$^1$H-NMR (DMSO-$d_6$) δ 1.32-1.42 (m, 1 H), 1.59-1.89 (m, 3 H), 2.85 (t, J=4.5 Hz, 4 H), 3.48-3.56 (m, 4 H), 3.62 (t, J=4.5 Hz, 4 H), 3.84-3.92 (m, 1 H), 5.72-5.80 (m, 1 H), 7.35-7.43 (m, 3 H), 7.50-7.59 (m, 4 H), 7.66 (d, J=8.6 Hz, 2 H), 8.40 (s, 1 H), 13.10 (br s, 1 H). Mass Spectrum (ESI) m/e=520.0 (M+1).

Example 11

N-(2-Morpholin-4-yl-ethyl)-4-{5-phenyl-4-[(tetrahydrofuran-2-ylmethyl)-amino]-7H-pyrrolo[2,3-d]pyrimidin-6-yl}-benzenesulfonamide

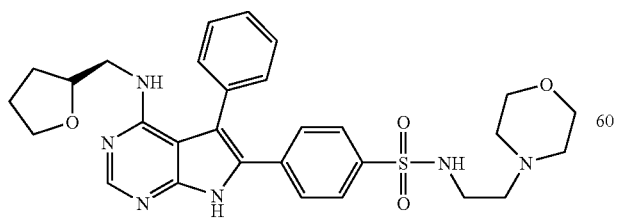

$^1$H-NMR (DMSO-$d_6$) δ 1.29-1.39 (m, 1 H), 1.56-1.84 (m, 3 H), 2.18-2.29 (m, 6 H), 2.81-2.91 (m, 2 H), 3.38-3.54 (m, 8 H), 3.78-3.88 (m, 1 H), 4.96-5.02 (m, 1 H), 7.34-7.41 (m, 3 H), 7.44-7.53 (m, 5 H), 7.66 (d, J=8.6 Hz, 2 H), 8.21 (s, 1 H), 12.34 (br s, 1 H). Mass Spectrum (ESI) m/e=563.0 (M+1).

Example 12

N-Allyl-4-{5-phenyl-4-[(tetrahydro-furan-2-ylmethyl)-amino]-7H-pyrrolo[2,3-d]pyrimidin-6-yl}-benzenesulfonamide

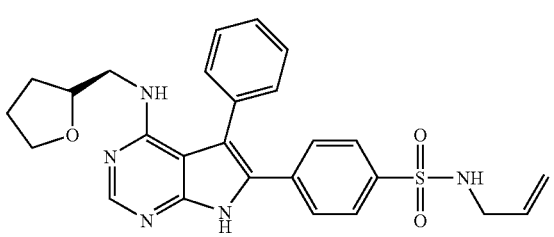

$^1$H-NMR (DMSO-$d_6$) δ 1.31-1.42 (m, 1 H), 1.58-1.87 (m, 3 H), 3.42 (t, J=5.8 Hz, 2 H), 3.48-3.57 (m, 4 H), 3.84-3.91 (m, 1 H), 5.01 (dd, J=10.3 Hz, 1.5 Hz, 1 H), 5.11 (dd, J=17.1 Hz, 1.6 Hz, 1 H), 5.53 (br s, 1 H), 5.58-5.70 (m, 1 H), 7.34-7.42 (m, 3 H), 7.46-7.55 (m, 4 H), 7.68 (d, J=8.5 Hz, 2 H), 7.80 (t, J=5.9 Hz, 1 H), 8.34 (s, 1 H), 12.82 (br s, 1 H). Mass Spectrum (ESI) m/e=490.0 (M+1).

Example 13

(4-{5-Phenyl-4-[(tetrahydrofuran-2-ylmethyl)-amino]-7H-pyrrolo[2,3-d]pyrimidin-6-yl}-benzenesulfonylamino)-acetic acid tert-butyl ester

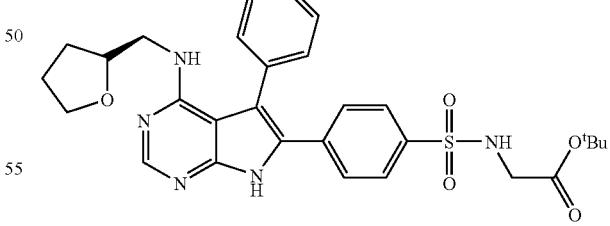

$^1$H-NMR (DMSO-$d_6$) δ 1.27-1.41 (m, 1 H), 1.28 (s, 9 H), 1.57-1.86 (m, 3 H), 3.48-3.61 (m, 6 H), 3.81-3.90 (m, 1 H), 5.21-5.40 (m, 1 H), 7.35-7.42 (m, 3 H), 7.43-7.54 (m, 4 H), 7.65 (d, J=8.4 Hz, 2 H), 8.10 (t, J=6.1 Hz, 1 H), 8.30 (s, 1 H), 12.65 (br s, 1 H). Mass Spectrum (ESI) m/e=564.1 (M+1).

Example 14

[Ethoxycarbonylmethyl-(4-{5-phenyl-4-[(tetrahydro-furan-2-ylmethyl)-amino]-7H-pyrrolo[2,3-d]pyrimidin-6-yl}-benzenesulfonyl)-amino]-acetic acid ethyl ester

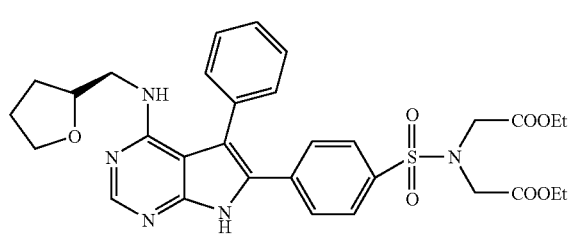

¹H-NMR (CD₃OD) δ 1.20 (t, J=7.0 Hz, 6 H), 1.39-1.55 (m, 1 H), 1.66-1.95 (m, 3 H), 3.53-3.65 (m, 4 H), 3.89-3.98 (m, 1 H), 4.04-4.28 (m, 8 H), 7.39-7.47 (m, 2 H), 7.46-7.58 (m, 5 H), 7.73 (d, J=8.3 Hz, 2 H), 8.23 (s, 1 H). Mass Spectrum (ESI) m/e=622.0 (M+1).

Example 15

4-{5-Phenyl-4-[(tetrahydrofuran-2-ylmethyl)-amino]-7H-pyrrolo[2,3-d]pyrimidin-6-yl}-benzenesulfonamide

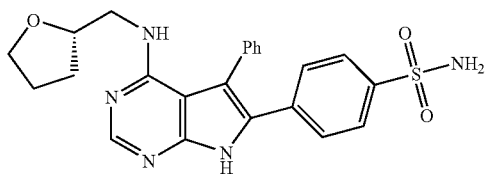

A mixture of 20 mg (0.04 mmol) of N-allyl-4-{5-phenyl-4-[(tetrahydro-furan-2-ylmethyl)-amino]-7H-pyrrolo[2,3-d]pyrimidin-6-yl}-benzenesulfonamide (Example 12) and 10 mg (0.02 mmol) of 1,3-bis(diphenylphosphino)propanenickel(II) chloride in 2.5 ml toluene was cooled to 0° C. and treated with 275 μl (0.3 mmol) of a 1.0 M solution of DIBALH in toluene. The brown slurry was warmed to room temperature and stirred for 3 h, and then an additional 100 μl (0.1 mmol) of DIBALH solution was added. After stirring for 18 h, the reaction mixture was treated with ether (1.5 ml) and 0.5 N aqueous sodium hydroxide solution (300 μl). The resultant mixture was stirred vigorously for 45 min and concentrated. The residue was purified by HPLC (Capcell Pak C₁₈ 5 μm, gradient of 80% A:20% B to 20% A:80% B over 45 min; A=0.5% TFA in water, B=0.5% TFA in acetonitrile) to give the title compound. ¹H-NMR (CD₃OD) δ 1.43-1.54 (m, 1 H), 1.71-2.03 (m, 3 H), 3.47 (dd, J=13.5 Hz, 6.0 Hz, 1 H), 3.61-3.70 (m, 3 H), 3.97-4.02 (m, 1 H), 7.42-7.48 (m, 2 H), 7.50 (d, J=8.5 Hz, 2 H), 7.52-7.58 (m, 3 H), 7.82 (d, J=8.5 Hz, 2 H), 8.35 (s, 1 H). Mass Spectrum (ESI) m/e=450.1 (M+1).

Example 16

N-(2,3-Dihydroxy-propyl)-4-{5-phenyl-4-[(tetrahydrofuran-2-ylmethyl)-amino]-7H-pyrrolo[2,3-d]pyrimidin-6-yl}-benzenesulfonamide

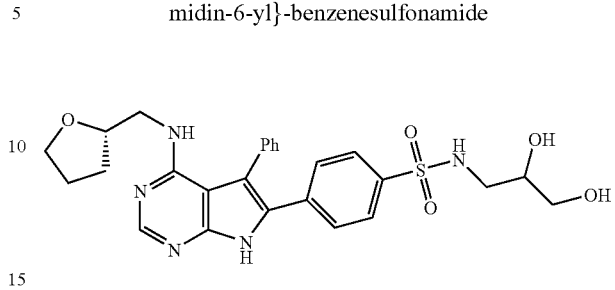

A solution of 26 mg (0.1 mmol) of N-allyl-4-{5-phenyl-4-[(tetrahydro-furan-2-ylmethyl)-amino]-7H-pyrrolo[2,3-d]pyrimidin-6-yl}-benzenesulfonamide (Example 12) in 2.8 ml acetone and 1 ml water was treated with 62 μl (0.005 mmol) of a 2.5 wt. % solution of OsO₄ in tert-butanol and 19 mg (0.2 mmol) of 4-methylmorpholine-N-oxide. The yellow solution was stirred at room temperature for 26 h, then was quenched with water (10 ml) and extracted with dichloromethane (3×). The combined organic layers were dried over Na₂SO₄, filtered, and the filtrate was purified by chromatography on silica gel (CH₂Cl₂:MeOH, 22:3) to give the title compound. ¹H-NMR (DMSO-d₆) δ 1.29-1.40 (m, 1 H), 1.53-1.84 (m, 3 H), 2.40-2.49 (m, 1 H), 2.53-2.63 (m, 1 H), 2.82-2.90 (m, 1 H), 3.21-3.59 (m, 6 H), 3.69-3.77 (m, 1 H), 4.51 (t, J=5.6 Hz, 1 H), 4.75 (d, J=5.1 Hz, 1 H), 4.97-5.03 (m, 1 H), 7.37-7.42 (m, 3 H), 7.44-7.53 (m, 5 H), 7.65 (d, J=8.5 Hz, 2 H), 8.21 (s, 1 H), 12.34 (br s, 1 H). Mass Spectrum (ESI) m/e=524.0 (M+1).

Example 17

2-(4-(N-(5-phenyl-4-(((tetrahydrofuran-2-yl)methylamino)-7H-pyrrolo[2,3-d]pyrimidin-6-yl)sulfamoyl)phenyl)acetic acid

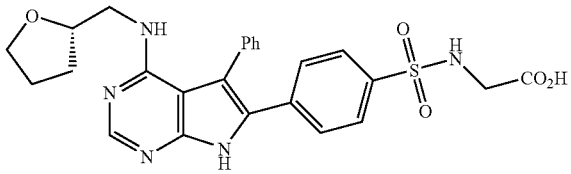

A slurry of 30 mg (0.05 mmol) of (4-{5-phenyl-4-[(tetrahydro-furan-2-ylmethyl)-amino]-7H-pyrrolo[2,3-d]pyrimidin-6-yl}-benzenesulfonylamino)-acetic acid tert-butyl ester (Example 13) in 3.5 ml CH₂Cl₂ was treated with 1 ml TFA and 1 ml water. After 1 h at room temperature, 1 ml THF was added and the dark red solution was heated to 50° C. for 19 h. The reaction mixture was concentrated and the residue was purified by HPLC (Capcell Pak C₁₈ 5 μm, gradient of 80% A:20% B to 20% A:80% B over 45 min; A=0.5% TFA in water, B=0.5% TFA in acetonitrile) to give the title compound. ¹H-NMR (DMSO-d₆) δ 1.31-1.41 (m, 1 H), 1.59-1.87 (m, 3 H), 3.44-3.61 (m, 6 H), 3.83-3.91 (m, 1 H), 5.32-5.53 (m, 1 H), 7.35-7.42 (m, 3 H), 7.45-7.54 (m, 4 H), 7.68 (d, J=8.4 Hz, 2 H), 8.04 (t, J=6.1 Hz, 1 H), 8.32 (s, 1 H), 12.75 (br s, 1 H). Mass Spectrum (ESI) m/e=508.0 (M+1).

Example 18

N-(2-Hydroxy-ethyl)-4-{5-phenyl-4-[(tetrahydro-furan-2-ylmethyl)-amino]-7H-pyrrolo[2,3-d]pyrimidin-6-yl}-benzenesulfonamide

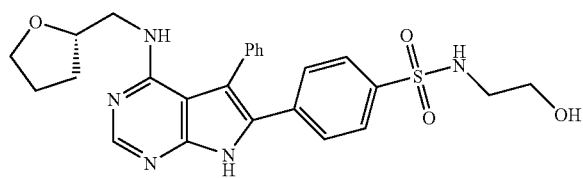

A slurry of 60 mg (0.1 mmol) of (4-{5-phenyl-4-[(tetrahydro-furan-2-ylmethyl)-amino]-7H-pyrrolo[2,3-d]pyrimidin-6-yl}-benzenesulfonylamino)-acetic acid tert-butyl ester (Example 13) in 10 ml $CH_2Cl_2$ was treated with 535 µl (0.5 mmol) of a 1 M solution of DIBALH in toluene. The orange solution was stirred at room temperature for 26 h, and then was quenched with saturated aqueous ammonium chloride solution (1 ml). The resultant mixture was stirred vigorously at room temperature for 16 h and concentrated. The residue was purified by HPLC (Capcell Pak $C_{18}$ 5 µm, gradient of 80% A:20% B to 20% A:80% B over 45 min; A=0.5% TFA in water, B=0.5% TFA in acetonitrile) and then chromatography on silica gel ($CH_2Cl_2$:MeOH, 23:2) to give the title compound. $^1$H-NMR (DMSO-$d_6$) δ 1.30-1.40 (m, 1 H), 1.56-1.85 (m, 3 H), 3.21-3.60 (m, 8 H), 3.80-3.85 (m, 1 H), 4.69 (br s, 1 H), 4.96-5.04 (m, 1 H), 7.35-7.42 (m, 2 H), 7.42-7.53 (m, 5 H), 7.66 (dd, J=11.3 Hz, 8.2 Hz, 2 H), 8.21 (s, 1 H), 12.33 (br s, 1 H). Mass Spectrum (ESI) m/e=494.0 (M+1).

Example 19

,N-Bis-(2-hydroxyethyl)-4-{5-phenyl-4-[(tetrahydro-furan-2-ylmethyl)-amino]-7H-pyrrolo[2,3-d]pyrimidin-6-yl}-benzenesulfonamide

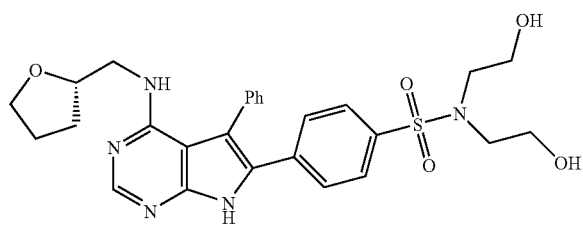

A solution of 33 mg (0.05 mmol) of [ethoxycarbonylmethyl-(4-{5-phenyl-4-[(tetrahydro-furan-2-ylmethyl)-amino]-7H-pyrrolo[2,3-d]pyrimidin-6-yl}-benzenesulfonyl)-amino]-acetic acid ethyl ester (Example 14) in 5 ml THF was cooled to 0° C. and treated with 13 mg (0.6 mmol) of $LiBH_4$. The orange solution was warmed to room temperature and stirred for 2.5 h, and then was quenched with saturated aqueous ammonium chloride (1 ml). The resultant mixture was concentrated, and the residue was purified by HPLC (Capcell Pak $C_{18}$ 5 µm, gradient of 80% A:20% B to 20% A:80% B over 45 min; A=0.5% TFA in water, B=0.5% TFA in acetonitrile) and then chromatography on silica gel ($CH_2Cl_2$:MeOH, 95:5) to give the title compound. $^1$H-NMR (CD$_3$OD) δ 1.44-1.52 (m, 1 H), 1.69-1.79 (m, 1 H), 1.79-1.95 (m, 2 H), 3.29 (t, J=5.8 Hz, 4 H), 3.56 (d, J=4.5 Hz, 2 H), 3.57-3.65 (m, 2 H), 3.72 (t, J=5.8 Hz, 4 H), 3.92-3.98 (m, 1 H), 7.44 (d, J=6.5 Hz, 2 H), 7.48-7.58 (m, 5 H), 7.74 (d, J=8.5 Hz, 2 H), 8.22 (s, 1 H). Mass Spectrum (ESI) m/e=538.0 (M+1).

Example 20

{6-[4-(2-Dimethylamino-ethoxy)-phenyl]-5-phenyl-7H-pyrrolo[2,3-d]pyrimidin-4-yl}-(tetrahydro-furan-2-ylmethyl)-amine

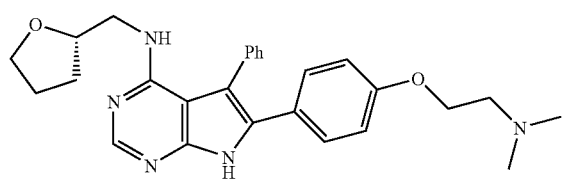

Step A: Dimethyl-{2-[4-(4,4,5,5-tetramethyl-[1,3,2]dioxaborolan-2-yl)-phenoxy]-ethyl}-amine A solution of 600 mg (2.6 mmol) of 4-(4,4,5,5-tetramethyl-1,3,2-dioxaborolan-2-yl)phenol, 900 mg (3.4 mmol) of $PPh_3$, and 345 µl (3.4 mmol) of N,N-dimethylethanolamine in 20 ml THF was cooled to 0° C. and treated with 540 µl (3.4 mmol) of DEAD dropwise. The orange solution was warmed to room temperature and stirred for 17 h. The reaction mixture was quenched with water (40 ml) and extracted with ethyl acetate (3×). The combined organic layers were dried over $Na_2SO_4$, filtered, and the filtrate was purified by HPLC (Capcell Pak $C_{18}$ 5 µm, gradient of 80% A:20% B to 20% A:80% B over 45 min; A=0.5% TFA in water, B=0.5% TFA in acetonitrile) to give the title compound. $^1$H-NMR (CDCl$_3$) δ 1.33 (s, 12 H), 3.00 (s, 6 H), 3.56 (t, J=4.4 Hz, 2 H), 4.36 (t, J=4.4 Hz, 2 H), 6.87 (d, J=8.6 Hz, 2 H), 7.76 (d, J=8.6 Hz, 2 H). Mass Spectrum (ESI) m/e=292.1 (M+1).

Step B: {6-[4-(2-Dimethylamino-ethoxy)-phenyl]-5-phenyl-7H-pyrrolo[2,3-d]pyrimidin-4-yl}-(tetrahydro-furan-2-ylmethyl)-amine A mixture of 63 mg (0.2 mmol) of (6-iodo-5-phenyl-7H-pyrrolo[2,3-d]pyrimidin-4-yl)-(tetrahydrofuran-2-ylmethyl)-amine (Example 5, Step E), 52 mg (0.2 mmol) of dimethyl-{2-[4-(4,4,5,5-tetramethyl-[1,3,2]dioxaborolan-2-yl)-phenoxy]-ethyl}-amine, 20 mg (0.5 mmol) of LiCl, 12.5 mg (0.02 mmol) of Pd(dppf)$_2$Cl$_2$.CH$_2$Cl$_2$ and 190 µl (0.4 mmol) of 2 M aqueous sodium carbonate solution in 2 ml toluene and 2 ml ethanol was purged with nitrogen for 2 min. The brown slurry was heated at 80° C. for 6 h and then 12.5 mg (0.02 mmol) of Pd(dppf)$_2$Cl$_2$.CH$_2$Cl$_2$ was added. After an additional 25 h at 80° C., the reaction mixture was concentrated. The residue was purified by HPLC (Capcell Pak $C_{18}$ 5 µm, gradient of 80% A:20% B to 20% A:80% B over 45 min; A=0.5% TFA in water, B=0.5% TFA in acetonitrile) to give the title compound. $^1$H-NMR (DMSO-$d_6$) δ 1.30-1.40 (m, 1 H), 1.57-1.87 (m, 3 H), 2.85 (s, 3 H), 2.86 (s, 3 H), 3.46-3.66 (m, 6 H), 3.81-3.90 (m, 1 H), 4.29 (t, J=4.9 Hz, 2 H), 5.39 (br s, 1 H), 6.94 (d, J=8.9 Hz, 2 H), 7.30 (d, J=8.9 Hz, 2 H), 7.36 (dd, J=7.7 Hz, 1.8 Hz, 2 H), 7.44-7.53 (m, 3 H), 8.30 (s, 1 H), 12.56 (br s, 1 H). Mass Spectrum (ESI) m/e=458.2 (M+1).

The examples in the following table were prepared as described in Example 20:

TABLE

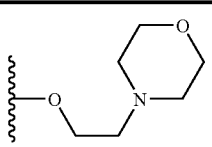

| Example | R |
|---------|---|
| 21 | 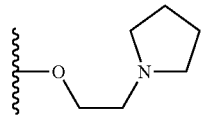 |
| 22 | 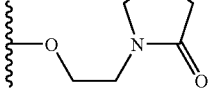 |
| 23 | 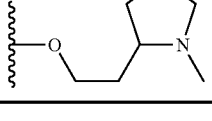 |
| 24 | |

Example 21

{6-[4-(2-Morpholin-4-yl-ethoxy)-phenyl]-5-phenyl-7H-pyrrolo[2,3-d]pyrimidin-4-yl}-(tetrahydro-furan-2-ylmethyl)-amine

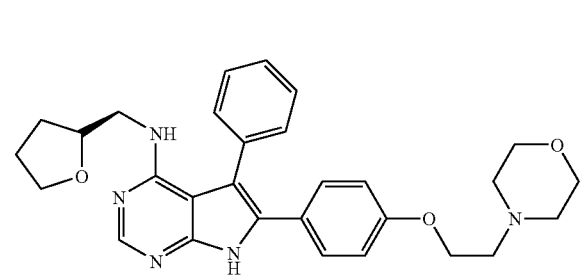

The compound was made using the procedure of Example 20 (Section 0): $^1$H-NMR (DMSO-d$_6$) δ 1.31-1.41 (m, 1 H), 1,57-1.69 (m, 1 H), 1.69-1.87 (m, 2 H), 3.14-3.27 (m, 2 H), 3.46-3.59 (m, 4 H), 3.62-3.76 (m, 2H) 3.82-3.92 (m, 1 H), 3.93-4.05 (m, 4 H), 4.34 (t, J=4.5 Hz, 2 H), 5.56 (br s 1 H), 6.95 (d, J=8.5 Hz, 2 H), 7.29 (d, J=9.0 Hz, 2 H), 7.37 (dd, J=7.6 Hz, 1.5 Hz, 2 H), 7.44-7.53 (m, 3 H), 8.34 (s, 1 H), 12.73 (br s, 1 H). Mass Spectrum (ESI) m/e=500.1 (M+1).

Example 22

{5-Phenyl-6-[4-(2-pyrrolidin-1-yl-ethoxy)-phenyl]-7H-pyrrolo[2,3-d]pyrimidin-4-yl}-(tetrahydrofuran-2-ylmethyl)-amine

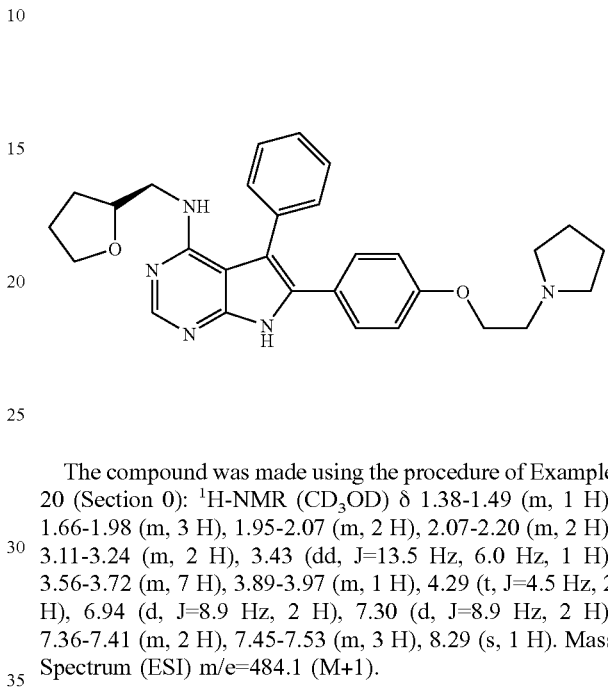

The compound was made using the procedure of Example 20 (Section 0): $^1$H-NMR (CD$_3$OD) δ 1.38-1.49 (m, 1 H), 1.66-1.98 (m, 3 H), 1.95-2.07 (m, 2 H), 2.07-2.20 (m, 2 H), 3.11-3.24 (m, 2 H), 3.43 (dd, J=13.5 Hz, 6.0 Hz, 1 H), 3.56-3.72 (m, 7 H), 3.89-3.97 (m, 1 H), 4.29 (t, J=4.5 Hz, 2 H), 6.94 (d, J=8.9 Hz, 2 H), 7.30 (d, J=8.9 Hz, 2 H), 7.36-7.41 (m, 2 H), 7.45-7.53 (m, 3 H), 8.29 (s, 1 H). Mass Spectrum (ESI) m/e=484.1 (M+1).

Example 23

1-[2-(4-{5-Phenyl-4-[(tetrahydrofuran-2-ylmethyl)-amino]-7H-pyrrolo[2,3-d]pyrimidin-6-yl}-phenoxy)-ethyl]-pyrrolidin-2-one

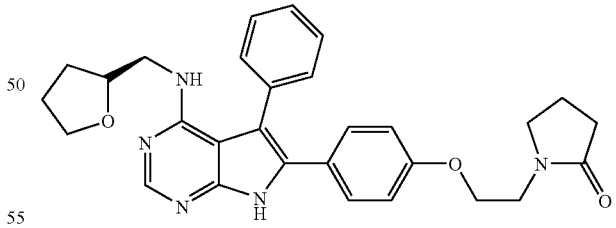

The compound was made using the procedure of Example 20: $^1$H-NMR (DMSO-d$_6$) δ 1.31-1.41 (m, 1 H), 1.61-1.70 (m, 1 H), 1.70-1.79 (m, 1 H), 1.79-1.84 (m, 3 H), 2.19 (t, J=8.0 Hz, 2 H), 3.42 (t, J=6.5 Hz, 2 H), 3.45-3.57 (m, 6 H), 3.86-3.93 (m, 1 H), 4.06 (t, J=5.0 Hz, 2 H), 5.72 (br s, 1 H), 6.89 (d, J=8.0 Hz, 2 H), 7.25 (d, J=8.5 Hz, 2 H), 7.34-7.40 (m, 3 H), 7.45-7.53 (m, 2 H), 8.37 (s, 1 H), 12.85 (br s, 1 H). Mass Spectrum (ESI) m/e=498.1 (M+1).

Example 24

(6-{4-[2-(1-Methyl-pyrrolidin-2-yl)-ethoxy]-phenyl}-5-phenyl-7H-pyrrolo[2,3-d]pyrimidin-4-yl)-(tetrahydrofuran-2-ylmethyl)-amine

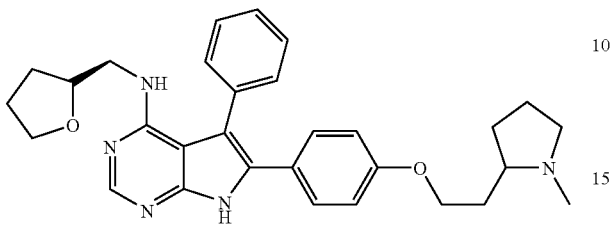

The compound was made using the procedure of Example 20: ¹H-NMR (CD₃OD) δ 1.41-1.50 (m, 1 H), 1.66-1.75 (m, 1 H), 1.76-1.91 (m, 3 H), 1.92-2.11 (m, 3 H), 2.29-2.42 (m, 2 H), 2.83 (s, 3 H), 2.95-3.06 (m, 1 H), 3.26-3.35 (m, 1 H), 3.50-3.63 (m, 5 H), 3.90-3.97 (m, 1 H), 4.04-4.16 (m, 2 H), 6.86 (d, J=9.0 Hz, 2 H), 7.28 (d, J=8.5 Hz, 2 H), 7.37 (d, J=7.0 Hz, 2 H), 7.40-7.49 (m, 3 H), 8.15 (s, 1 H). Mass Spectrum (ESI) m/e=498.1 (M+1).

Example 25

(4-{5-Phenyl-4-[(tetrahydrofuran-2-ylmethyl)-amino]-7H-pyrrolo[2,3-d]pyrimidin-6-yl}-phenoxy)-acetonitrile

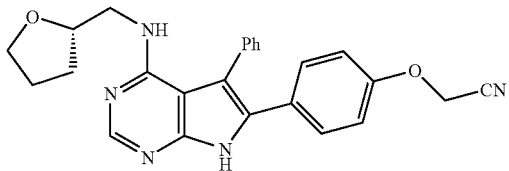

Step A: [4-(4,4,5,5-Tetramethyl-[1,3,2]dioxaborolan-2-yl)-phenoxy]-acetonitrile

A slurry of 357 mg (1.6 mmol) of 4-(4,4,5,5-tetramethyl-1,3,2-dioxaborolan-2-yl)phenol and 650 mg (4.7 mmol) of K₂CO₃ in 5 ml DMF was cooled to 0° C. and treated with 220 μl (3.2 mmol) of bromoacetonitrile dropwise. The brown slurry was warmed to room temperature, stirred for 1.5 h, then was quenched with water (20 ml) and was extracted with benzene (3×). The combined organic layers were dried over Na₂SO₄, filtered, and the filtrate was purified by chromatography on silica gel (hexanes:EtOAc, 17:3) to give the title compound. ¹H-NMR (CDCl₃) δ 1.34 (s, 12 H), 4.79 (s, 2 H), 6.96 (d, J=8.5 Hz, 2 H), 7.80 (d, J=8.5 Hz, 2 H). Mass Spectrum (ESI) m/e=260.2 (M+1, triplet).

Step B: (4-{5-Phenyl-4-[(tetrahydrofuran-2-ylmethyl)-amino]-7H-pyrrolo[2,3-d]pyrimidin-6-yl}-phenoxy)-acetonitrile The title compound was prepared as described in Example 20, Step B. ¹H-NMR (DMSO-d₆) δ 1.31-1.41 (m, 1 H), 1.59-1.87 (m, 3 H), 3.44-3.57 (m, 4 H), 3.85-3.92 (m, 1 H), 5.18 (s, 2 H), 5.61 (br s, 1 H), 7.02 (d, J=9.0 Hz, 2 H), 7.32 (d, J=9.0 Hz, 2 H), 7.34-7.42 (m, 3 H), 7.46-7.55 (m, 2 H), 8.34 (s, 1 H), 12.77 (br s, 1 H). Mass Spectrum (ESI) m/e=426.1 (M+1).

Example 26

N-Methyl-4-{5-phenyl-4-[(tetrahydrofuran-2-ylmethyl)-amino]-7H-pyrrolo[2,3-d]pyrimidin-6-yl}-benzamide

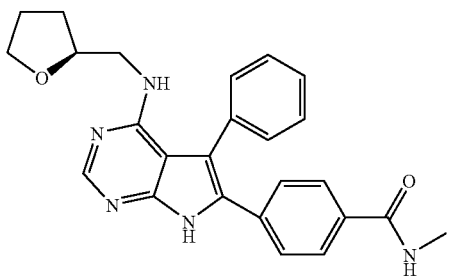

Step A: N-Methyl-(4,4,5,5-tetramethyl-[1,3,2]dioxaborolan-2-yl)-benzamide

A mixture of 4-(4,4,5,5-tetramethyl-1,3,2-dioxaborolan-2-yl)benzoic acid (1.0 g, 4.03 mmol), EDC (0.81 g, 4.23 mmol), and DMAP (catalytic amount) in 3 mL of DMF was stirred at room temperature for 1 hr, and then 2 mL of a 2M solution of N,N-dimethylamine in THF (4 mmol) was added into the reaction mixture. The resulting mixture was stirred at room temperature for 16 h. Ethyl acetate (100 mL) was added and the mixture was washed with saturated sodium bicarbonate and brine. The organic layer was dried over Na₂SO₄, filtered and the filtrate was concentrated. The solvent was removed to give the title compound which was used without further purification for the next step. Mass Spectrum (ESI) m/e=262 (M+1).

Step B: N-Methyl-4-{5-phenyl-4-[(tetrahydrofuran-2-ylmethyl)-amino]-7H-pyrrolo[2,3-d]pyrimidin-6-yl}-benzamide The title compound was prepared as described in Example 20, Step B. ¹H-NMR (400 MHz, CDCl₃)δ, 1.26-1.87 (m, 4 H), 3.02 (d, J=4.8 Hz, 3 H), 3.58-3.64 (m, 4 H), 3.96 (m, 1 H), 5.25 (s, 1 H), 6.16 (s, 1 H), 7.44-7.48 (m, 7 H), 7.71 (d, J=8.3 Hz, 2 H), 8.29 (s, 1 H), 12.66 (s, 1 H). Mass Spectrum (ESI) m/e=428 (M+1).

The following examples of Table 2 were prepared as described in Example 26.

TABLE

| Example | R |
|---|---|
| 27 | ![structure] |

TABLE-continued

| Example | R |
|---------|---|
| 28 | morpholine amide |
| 29 | cyclopropyl amide |
| 30 | 2-methoxyethyl amide |
| 31 | 2-morpholinoethyl amide |
| 32 | 2-dimethylaminoethyl amide |

Example 27

N,N-Dimethyl-4-{5-phenyl-4-[(tetrahydrofuran-2-ylmethyl)-amino]-7H-pyrrolo[2,3-d]pyrimidin-6-yl}-benzamide

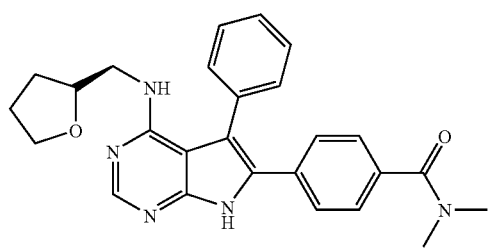

The title compound was prepared as described in Example 26: $^1$H-NMR (400 MHz, DMSO-$d_6$) δ 1.33 (m, 1 H), 1.62-1.85 (m, 3 H), 2.88 (s, 3 H), 2.95 (s, 3 H), 3.47-3.55 (m, 4 H), 3.86 (m, 1 H), 5.68 (s, 1 H), 7.32-7.54 (m, 9 H), 8.38 (s, 1 H), 12.93 (s, 1 H). Mass Spectrum (ESI) m/e=442 (M+1).

Example 28

Morpholin-4-yl-(4-{5-phenyl-4-[(tetrahydrofuran-2-ylmethyl)-amino]-7H-pyrrolo[2,3-d]pyrimidin-6-yl}-phenyl)-methanone The title compound was prepared as described in Example 26: $^1$H-NMR (400 MHz, DMSO-$d_6$) δ 1.06-1.86 (m, 4 H), 3.36-3,90 (m, 13 H), 5.91 (s, 1 H), 7.36-7.55 (m, 7 H), 7.78 (d, J=6.4 Hz, 2 H), 8.41 (s, 1 H), 13.2 (s, 1 H). Mass Spectrum (ESI) m/e=484 (M+1).

Example 29

N-Cyclopropyl-4-{5-phenyl-4-[(tetrahydrofuran-2-ylmethyl)-amino]-7H-pyrrolo[2,3-d]pyrimidin-6-yl}-benzamide The title compound was prepared as described in Example 26: $^1$H-NMR (400 MHz, CDCl$_3$) δ 0.62 (m, 2 H), 0.88 (m, 2 H), 1.44 (m, 1 H), 1.71-1.96 (m, 3 H), 2.90 (m, 1 H), 3.60-4.13 (m, 5 H), 6.06 (s, 1 H), 6.33 (s, 1 H), 7.42-7.68 (m, 7 H), 7.67 (d, J=6.8 Hz, 2 H), 8.33 (s, 1 H), 14.23 (s, 1 H). Mass Spectrum (ESI) m/e=454 (M+1).

Example 30

N-(2-Methoxyethyl)-4-{5-phenyl-4-[(tetrahydrofuran-2-ylmethyl)-amino]-7H-pyrrolo[2,3-d]pyrimidin-6-yl}-benzamide The title compound was prepared as described in Example 26: ¹H-NMR (400 MHz, DMSO-d₆) δ 1.34 (m, 1 H), 1.62-1.83 (m, 3 H), 3.26 (s, 3 H), 3.38-3.52 (m, 8 H), 3.87 (m, 1 H), 5.51 (s, 1 H), 7.33-7.52 (m, 7 H), 7.74 (d, J=6.0 Hz, 2 H), 8.33 (s, 1 H), 8.47 (t, J=4.9 Hz, 1 H), 12.77 (s, 1 H). Mass Spectrum (ESI) m/e=472 (M+1).

Example 31

N-(2-Morpholin-4-yl-ethyl)-4-{5-phenyl-4-[(tetrahydrofuran-2-ylmethyl)-amino]-7H-pyrrolo[2,3-d]pyrimidin-6-yl}-benzamide

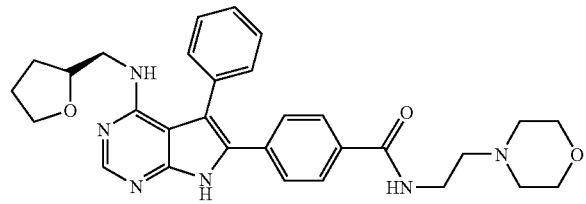

The title compound was prepared as described in Example 26: ¹H-NMR (400 MHz, DMSO-d₆) δ 1.37 (m, 1 H), 1.38-1.83 (m, 3 H), 3.13 (m, 2 H), 3.30 (m, 2 H), 3.49-3.67 (m, 10 H), 3.87 (m, 1 H), 3.99 (m, 2 H), 5.46 (s, 1 H), 7.3-7.53 (m, 7 H), 7.76 (d, J=8 Hz, 2 H), 8.33 (s, 1 H), 8.68 (t, J=4 Hz, 1 H), 12.75 (s, 1 H). Mass Spectrum (ESI) m/e=527 (M+1).

Example 32

N-(2-Dimethylamino-ethyl)-4-{5-phenyl-4-[(tetrahydrofuran-2-ylmethyl)-amino]-7H-pyrrolo[2,3-d]pyrimidin-6-yl}-benzamide

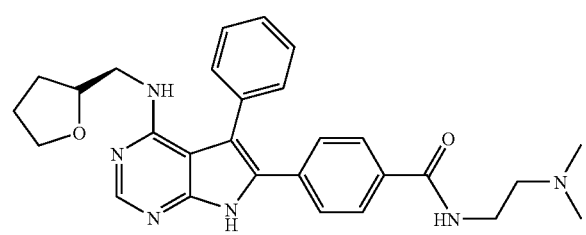

The title compound was prepared as described in Example 26: ¹H-NMR (400 MHz, DMSO-d₆) δ 1.36 (m, 1 H), 1.64-1.86 (m, 3 H), 2.83 (s, 6 H), 3.24 (m, 2 H), 3.51-3.59 (m, 6 H), 3.87 (m, 1 H), 5.50 (s, 1 H), 7.32-7.51 (m, 7 H), 7.76 (d, J=5.6 Hz, 2 H), 8.34 (s, 1 H), 8.65 (t, J=4.0 Hz, 1 H), 12.80 (s, 1 H). Mass Spectrum (ESI) m/e=485 (M+1).

Example 33

{6-[4-(2-Dimethylaminoethoxy)-phenyl]-5-phenyl-7H-pyrrolo[2,3-d]pyrimidin-4-yl}-[1,3]dithiolan-2-ylmethyl-amine

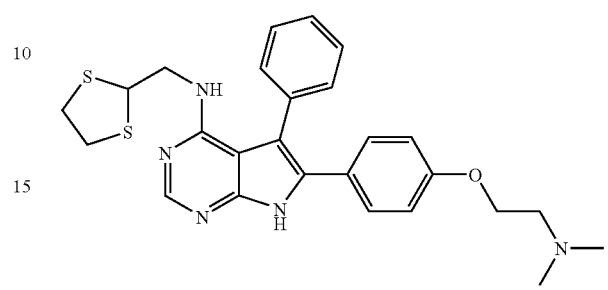

Step A: 2,2-Diethoxy-N-[5-phenyl-6-(triethyl-silan-yl)-7H-pyrrolo[2,3-d]pyrimidin-4-yl]-acetamide To a solution of 5-phenyl-6-(triethylsilyl)-7-H-pyrrolo[2,3-d]pyrimidin-4-amine (Example 5, Step C, 0.45 g, 1.38 mmol), EDC (0.34 g, 1.78 mmol) and HOBT (0.28 g, 2.07 mmol) in DMF (10.0 mL) was added 2,2-diethoxy acetic acid (0.25 g, 14.8 mmol) and the reaction mixture was stirred at rt for 16 h. Dichloromethane (50 mL) was added and the mixture was washed with brine, sat. NaHCO₃ solution and brine. The organic layer was dried over Na₂SO₄, filtered and the filtrate was concentrated. The product was dissolved in 5 mL of THF and slowly added to a 11 mL of a 1 M solution of LiAlH4 in THF (11 mmol) (40 mL) at 0° C. under N₂. The temperature of the reaction mixture was allowed to rise to room temperature for 1 hr after addition. The mixture was carefully poured into ice-water (50 mL). Ethyl acetate (50 mL) was added, and the organic layer was separated. The aqueous layer was extracted several times with ethyl acetate. The combined organic layers were washed with brine, dried over Na₂SO₄, filtered and the filtrate was concentrated. The residue was purified by chromatography on silica gel (CH₂Cl₂:MeOH=95:5) to give the title compound. ¹H-NMR (400 MHz, DMSO-d₆) δ 0.58 (q, 6H, 7.50 Hz), 0.79 (t, 9H, J=8.00 Hz), 1.04 (t, 6H, J=7.00 Hz), 3.40-3.33 (m, 2H), 3.53-3.46 (m, 4H), 4.43 (t, 1H, J=5.50 Hz), 4.84 (t, 1H, J=5.50 Hz), 7.50-7.37 (m, 5H), 8.19 (s, 1H), 11.5 (s, 1H). Mass Spectrum (ESI) m/e=441 (M+1).

Step B: (2,2-Diethoxy-ethyl)-(6-iodo-5-phenyl-7H-pyrrolo[2,3-d]pyrimidin-4-yl)-amine The title compound was prepared as described in Example 5, Step E. ¹H-NMR (400 MHz, DMSO-d₆) δ 1.03 (t, 6H, J=7.00 Hz), 3.42-3.36 (m, 2H), 3.56-3.50 (m, 4H), 4.50 (t, 1H, J=5.50 Hz), 5.01 (t, 1H, J=5.50 Hz), 7.55-7.41 (m, 5H), 8.16 (s, 1H), 12.41 (s, 1H). Mass Spectrum (ESI) m/e=453 (M+1).

Step C: (2,2-Diethoxyethyl)-{6-[4-(2-dimethylaminoethoxy)-phenyl]-5-phenyl-7H-pyrrolo[2,3-d]pyrimidin-4-yl}-amine The title compound was prepared as described in Example 20, Step B. Mass Spectrum (ESI) m/e=490 (M+1).

Step D: {6-[4-(2-Dimethylaminoethoxy)-phenyl]-5-phenyl-7H-pyrrolo[2,3-d]pyrimidin-4-yl}-[1,3]dithiolan-2-ylmethyl-amine (2,2-Diethoxyethyl)-{6-[4-(2-dimethylamino-ethoxy)-phenyl]-5-phenyl-7H-pyrrolo[2,3-d]pyrimidin-4-yl}-amine (Example 33, Step C; 50 mg, 0.12 mmol) was combined with 12 μl ethanedithiol in 5 ml toluene, then the mixture was heated to reflux for 4 h. After that time the mixture was cooled to rt, concentrated and purified by chromatography on silica gel (CH$_2$Cl$_2$:MeOH=95:5) to give the title compound. $^1$H-NMR (400 MHz, DMSO-d$_6$) δ 2.21 (s, 6H), 2.61 (t, 2H, J=5.73 Hz), 3.16-3.05 (m, 4H), 3.61 (t, 2H, J=6.07 Hz), 4.03 (t, 2H, J=5.77 Hz), 4.68 (t, 1H, J=6.29 Hz), 5.23 (t, 1H, J=5.86 Hz), 6.86 (d, 2H, J=8.84 Hz), 7.25 (d, 2H, J=8.80 Hz), 8.14-7.38 (m, 5H), 8.21 (s, 1H), 12.12 (s, 1H). Mass Spectrum (ESI) m/e=492 (M+1).

Example 34

Cyclobutylmethyl-{6-[4-(2-dimethylamino-ethoxy)-phenyl]-5-phenyl-7H-pyrrolo[2,3-d]pyrimidin-4-yl}-amine

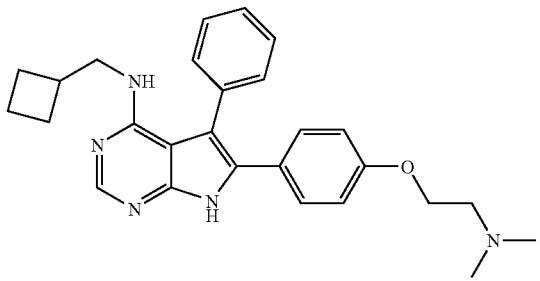

Step A. 6-(4-(2-(dimethylamino)ethoxy)phenyl)-5-phenyl-7H-pyrrolo[2,3-d]pyrimidin-4-amine A slurry of 2.08 g (6.4 mmol) of 5-phenyl-6-(triethylsilyl)-7H-pyrrolo[2,3-d]pyrimidin-4-amine (Example 5, Step C) and 1.91 g (8.4 mmol) of N-iodosuccinimide in 65 ml CH$_3$CN was stirred for 2 h. The reaction mixture was partitioned between dichloromethane (300 ml) and a 4:1 mixture of brine and saturated aqueous sodium thiosulfate (100 ml). The organic layer was washed with saturated aqueous sodium bicarbonate (1×) and brine (1×), dried over Na$_2$SO$_4$ and filtered.

A mixture of 2.69 g (8.0 mmol) of the crude iodide from above, 3.00 g (10.3 mmol) of dimethyl-{2-[4-(4,4,5,5-tetramethyl-[1,3,2]dioxaborolan-2-yl)-phenoxy]-ethyl}-amine (Example 20, Step A), 1.38 g (32.6 mmol) of LiCl, 1.62 g (2.0 mmol) of Pd(dppf)$_2$Cl$_2$.CH$_2$Cl$_2$ and 11.9 ml (23.8 mmol) of 2 M aqueous sodium carbonate solution in 75 ml toluene and 75 ml ethanol was purged with nitrogen for 2 min. The brown slurry was heated to 80° C. for 25.5 h and then was concentrated. The residue was purified by chromatography on silica gel (CH$_2$Cl$_2$:MeOH, 9:1 grading to CH$_2$Cl$_2$:MeOH, 4:1) to give the title compound. $^1$H-NMR (DMSO-d$_6$) δ 2.35 (s, 6 H), 2.80 (t, J=5.5 Hz, 2 H), 4.09 (t, J=5.5 Hz, 2 H), 6.86 (d, J=9.0 Hz, 2 H), 7.25 (d, J=9.0 Hz, 2 H), 7.35 (d, J=7.0 Hz, 2 H), 7.38-7.43 (m, 1 H), 7.43-7.48 (m, 2 H), 8.10 (s, 1 H), 12.02 (s, 1 H). Mass Spectrum (ESI) m/e=374.2 (M+1).

Step B. Cyclobutylmethyl-{6-[4-(2-dimethylamino-ethoxy)-phenyl]-5-phenyl-7H-pyrrolo[2,3-d]pyrimidin-4-yl}-amine A slurry of 80 mg (0.2 mmol) of 6-[4-(2-dimethylamino-ethoxy)-phenyl]-5-phenyl-7H-pyrrolo[2,3-d]pyrimidin-4-amine, 25 μl (0.3 mmol) of cyclobutanecarboxylic acid, 53 mg (0.3 mmol) of EDC, 43 mg (0.3 mmol) of HOBt and a catalytic amount of DMAP in 2.5 ml DMF was stirred at room temperature for 22 h, and then was warmed to 60° C. and stirred for an additional 6 h. The reaction mixture was partitioned between dichloromethane (60 ml) and brine. The organic layer was washed with saturated aqueous sodium bicarbonate (1×) and water (1×), dried over Na$_2$SO$_4$ and filtered.

A solution of the crude amide in 5 ml THF was added to a slurry of 34 mg (95%, 0.9 mmol) of lithium aluminum hydride in 5 ml THF at 0° C. Gas evolution was observed. The brown slurry was warmed to 50° C. and stirred for 14 h, and then 38 mg (95%, 1.0 mmol) of lithium aluminum hydride was added. After an additional 4 h at 50° C., the reaction mixture was cooled to room temperature and poured into ice water. The aqueous material was extracted with ethyl acetate (4×). The combined organic layers were dried over Na$_2$SO$_4$, filtered, and the filtrate was purified by HPLC (Capcell Pak C$_{18}$ 5 μm, gradient of 80% A:20% B to 20% A:80% B over 45 min; A=0.5% TFA in water, B=0.5% TFA in acetonitrile) to give the title compound. $^1$H-NMR (CD$_3$OD) δ 1.52-1.61 (m, 2 H), 1.75-1.97 (m, 4 H), 2.39-2.48 (m, 1 H), 2.94 (s, 6 H), 3.41 (d, J=6.0 Hz, 2 H), 3.56 (t, J=3.8 Hz, 2 H), 4.32 (t, J=3.8 Hz, 2 H), 6.95 (d, J=6.8 Hz, 2 H), 7.33 (d, J=6.8 Hz, 2 H), 7.37-7.44 (m, 2 H), 7.46-7.54 (m, 3 H), 8.27 (s, 1 H). Mass Spectrum (ESI) m/e=442.3 (M+1).

Example 35 trans/cis-{6-[4-(2-Dimethylamino-ethoxy)-phenyl]-5-phenyl-7H-pyrrolo[2,3-d]pyrimidin-4-yl}-(2-methoxy-cyclobutylmethyl)-amine

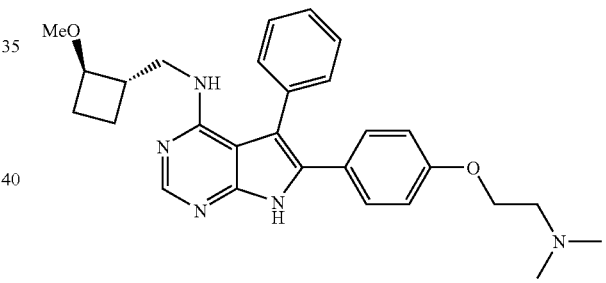

Step A. trans/cis-2-Methoxycyclobutane Carboxylic Acid

To 370 ml (370 mmol) of a 1 M solution of triisobutylaluminum in hexanes at 0° C. was added 21 ml (184 mmol) of 3,4-dihydro-2-methoxy-2H-pyran dropwise over 15 min. The colorless solution was stirred at 0° C. for 1.75 h then was heated at reflux for 24 h. The reaction mixture was cooled to 0° C., quenched by cautious addition of water (100 ml) and stirred until bubbling had subsided. Ether (200 ml) and saturated aqueous ammonium chloride (130 ml) were added and the resulting biphasic mixture was warmed to room temperature and stirred for 10 h. The precipitate was removed by filtration and the organic layer was dried over Na$_2$SO$_4$, filtered and distilled.

To a mixture of 3.18 g (27.4 mmol) of the alcohol and 440 mg (98%, 2.8 mmol) of TEMPO in 135 ml CH$_3$CN and 95 ml pH 6.7 aqueous NaOH—NaH$_2$PO$_4$ buffer at 35° C. was added a solution of 6.5 g (80%, 57.5 mmol) of sodium chlorite in 29 ml water and a solution of 1.05 ml bleach in 15 ml water simultaneously over a 50 min period. The dark red slurry was stirred at 35° C. for 25 h, then 250 μl bleach and 108 mg (98%, 0.7 mmol) of TEMPO were added. Stirring was continued at 35° C. for an additional 2 h. The reaction mixture was basified by the addition of water (210 ml) and 2 M aqueous sodium hydroxide solution (32 ml). The resulting mixture was poured into a 0° C. solution of sodium sulfite (5.3 g) in 250 ml water, warmed to room temperature, and stirred for 17 h. Ether (135 ml) was added and the layers were separated. The organic layer was discarded and the aqueous layer was diluted with ether (200 ml) and acidified with conc. HCl until pH=2. The layers were separated and the organic layer was washed with water (2×) and brine (1×), dried over Na$_2$SO$_4$ and filtered. The crude product was carried on directly into the subsequent step. $^1$H-NMR (CDCl$_3$) δ 1.76-1.85 (m, 1 H), 1.85-1.94 (m, 1 H), 1.99-2.08 (m, 1 H), 2.16-2.25 (m, 1 H), 2.99-3.06 (m, 1 H), 3.31 (s, 3 H), 4.04 (q, J=7.5 Hz, 1 H).

Step B. trans/cis-{6-[4-(2-Dimethylamino-ethoxy)-phenyl]-5-phenyl-7H-pyrrolo[2,3-d]pyrimidin-4-yl}-(2-methoxy-cyclobutylmethyl)-amine A slurry of 240 mg (0.7 mmol) of 5-phenyl-6-(triethylsilyl)-7H-pyrrolo[2,3-d]pyrimidin-4-amine (Example 5, Step C), 116 mg (0.9 mmol) of trans/cis-2-methoxycyclobutane carboxylic acid, 188 mg (1.0 mmol) of EDC, 150 mg (1.1 mmol) of HOBt and a catalytic amount of DMAP in 5 ml DMF was stirred at room temperature for 20 h. The reaction mixture was partitioned between dichloromethane (60 ml) and brine. The organic layer was washed with saturated aqueous sodium bicarbonate (1×) and water (1×), dried over Na$_2$SO$_4$ and filtered.

A solution of the crude amide in 5 ml THF was added to a slurry of 64 mg (95%, 1.6 mmol) of lithium aluminum hydride in 5 ml THF at 0° C. Gas evolution was observed. The brown slurry was warmed to 50° C. and stirred for 19 h, and then 34 mg (95%, 0.9 mmol) of lithium aluminum hydride was added. After an additional 3.5 h at 50° C., the reaction mixture was cooled to room temperature and poured into ice water. The aqueous material was extracted with ethyl acetate (4×). The combined organic layers were dried over Na$_2$SO$_4$, filtered, and the filtrate was purified by chromatography on silica gel (CH$_2$Cl$_2$:MeOH, 95:5).

A slurry of 108 mg (0.3 mmol) of the silane and 72 mg (0.3 mmol) N-iodosuccinimide in 7 ml CH$_3$CN was stirred for 1.75 h. The reaction mixture was partitioned between dichloromethane (70 ml) and a 4:1 mixture of brine and saturated aqueous sodium thiosulfate (30 ml). The organic layer was washed with saturated aqueous sodium bicarbonate (1×) and brine (1×), dried over Na$_2$SO$_4$ and filtered.

A mixture of the crude iodide, 139 mg (0.5 mmol) of dimethyl-{2-[4-(4,4,5,5-tetramethyl-[1,3,2]dioxaborolan-2-yl)-phenoxy]-ethyl}-amine (Example 20, Step A), 48 mg (1.1 mmol) of LiCl, 59 mg (0.07 mmol) of Pd(dppf)$_2$Cl$_2$.CH$_2$Cl$_2$ and 435 µl (0.9 mmol) of 2 M aqueous sodium carbonate solution in 5 ml toluene and 5 ml ethanol was purged with nitrogen for 2 min. The brown slurry was heated to 80° C. for 15 h and then was concentrated. The residue was purified by chromatography on silica gel (CH$_2$Cl$_2$:MeOH, 9:1 grading to CH$_2$Cl$_2$:MeOH, 43:7) to give the title compound. $^1$H-NMR (CD$_3$OD) δ 1.10-1.21 (m, 1 H), 1.65-1.79 (m, 2 H), 2.10-2.20 (m, 1 H), 2.31-2.40 (m, 1 H), 2.99 (s, 6 H), 3.16 (s, 3 H), 3.44-3.63 (m, 3 H), 4.36 (t, J=5.0 Hz, 2 H), 7.01 (d, J=6.9 Hz, 2 H), 7.37 (d, J=6.9 Hz, 2 H), 7.43-7.48 (m, 2 H), 7.53-7.60 (m, 1 H), 8.34 (s, 1 H). Mass Spectrum (ESI) m/e=472.3 (M+1).

Example 36 trans/cis-2-({6-[4-(2-Dimethylamino-ethoxy)-phenyl]-5-phenyl-7H-pyrrolo[2,3-d]pyrimidin-4-ylamino}-methyl)-cyclobutanol

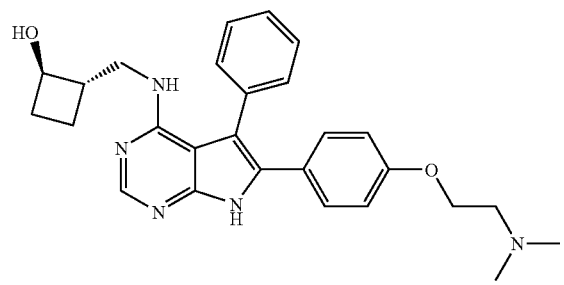

A solution of 34 mg (0.07 mmol) of trans/cis-{6-[4-(2-dimethylamino-ethoxy)-phenyl]-5-phenyl-7H-pyrrolo[2,3-d]pyrimidin-4-yl}-(2-methoxy-cyclobutylmethyl)-amine (Example 35, Step B) in 5 ml dichloromethane was cooled to −78° C. and treated with 80 µl (0.08 mmol) of 1 M solution of BBr$_3$ in dichloromethane. The orange slurry was stirred at −78° C. for 6.5 h, and then was warmed to 0° C. for 20 min. The reaction mixture was quenched with saturated aqueous sodium bicarbonate (5 ml) and stirred overnight. Water was added and the mixture was extracted with dichloromethane (3×). The combined organic layers were dried over Na$_2$SO$_4$, filtered and purified by chromatography on silica gel (CH$_2$Cl$_2$:MeOH, 4:1 grading to CH$_2$Cl$_2$:MeOH, 1:1) to give the title compound. $^1$H-NMR (CD$_3$OD) δ 0.91-0.99 (m, 1 H), 1.52-1.71 (m, 2 H), 2.03-2.10 (m, 1 H), 2.14-2.24 (m, 1 H), 2.39 (s, 6 H), 2.81 (t, J=4.0 Hz, 2 H), 3.50-3.57 (m, 1 H), 3.61-3.70 (m, 2 H), 4.10 (t, J=4.4 Hz, 2 H), 6.86 (d, J=6.8 Hz, 2 H), 7.27 (d, J=6.8 Hz, 2 H), 7.40 (d, J=6.0 Hz, 2 H), 7.42-7.51 (m, 3 H), 8.16 (s, 1 H). Mass Spectrum (ESI) m/e=458.2 (M+1).

Example 37 cis-2-({6-[4-(2-Dimethylamino-ethoxy)-phenyl]-5-phenyl-7H-pyrrolo[2,3-d]pyrimidin-4-ylamino}-methyl)-cyclopentanol

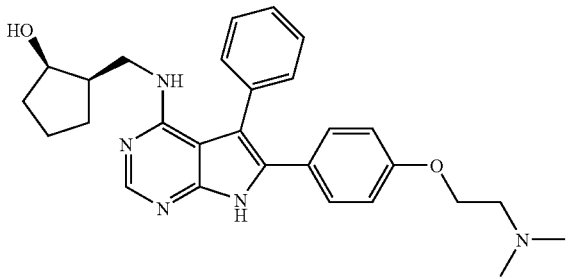

Step A. cis-tert-butyldimethylsilyl 2-(tert-butyldimethyl-silyloxy)cyclopentanecarboxylate A solution of 1.64 g (12.5 mmol) of cis-2-hydroxycyclopentanecarboxylic acid, 6.18 g (39.8 mmol) of imidazole and 6.27 g (92.1 mmol) of TBSCl in 11 ml DMF was stirred for 3 d. The reaction mixture was partitioned between ether (100 ml) and water. The organic layer was washed with water (2×) and brine (1×), dried over $Na_2SO_4$, filtered and purified by chromatography on silica gel (hexanes:EtOAc, 98.5:1.5) to give the title compound. $^1$H-NMR (CDCl$_3$) δ 0.03 (s, 3 H), 0.05 (s, 3 H), 0.26 (s, 3 H), 0.28 (s, 3 H), 0.85 (s, 9 H), 0.94 (s, 9 H), 1.51-1.62 (m, 1 H), 1.70-1.79 (m, 3 H), 1.83-1.93 (m, 1 H), 2.07-2.15 (m, 1 H), 2.67-2.74 (m, 1 H), 4.43-4.49 (m, 1 H).

Step B. cis-2-(tert-butyldimethylsilyloxy)cyclopentanecarboxylic acid

A solution of 1.25 g (3.5 mmol) of cis-2-(tert-butyldimethylsilyloxy)cyclopentanecarboxylic acid in 20 ml THF was treated with 10 ml of 1 M aqueous hydrochloric acid solution. The colorless solution was stirred for 3 h and then was extracted with ethyl acetate (3×). The combined organic layers were dried over $Na_2SO_4$, filtered and purified by chromatography on silica gel (hexanes:EtOAc, 97:3 grading to hexanes:EtOAc=44:6) to give the title compound. $^1$H-NMR (CDCl$_3$) δ 0.09 (s, 3 H), 0.10 (s, 3 H), 0.87 (s, 9 H), 1.55-1.65 (m, 1 H), 1.65-1.74 (m, 1 H), 1.74-1.94 (m, 3 H), 2.10-2.21 (m, 1 H), 2.71-2.78 (m, 1 H), 4.45-4.52 (m, 1 H).

Step C. cis-2-({6-[4-(2-Dimethylamino-ethoxy)-phenyl]-5-phenyl-7H-pyrrolo[2,3-d]pyrimidin-4-ylamino}-methyl)-cyclopentanol A slurry of 260 mg (0.7 mmol) of 6-[4-(2-dimethylamino-ethoxy)-phenyl]-5-phenyl-7H-pyrrolo[2,3-d]pyrimidin-4-ylamine (Example 34, Step A), 203 mg (0.8 mmol) of cis-2-(tert-butyldimethylsilyloxy)cyclopentanecarboxylic acid, 284 mg (1.5 mmol) of EDC, 233 mg (1.7 mmol) of HOBt and a catalytic amount of DMAP in 5 ml DMF was stirred at room temperature for 23 h. The reaction mixture was partitioned between dichloromethane (120 ml) and brine. The organic layer was washed with saturated aqueous sodium bicarbonate (1×) and water (1×), dried over $Na_2SO_4$ and filtered.

A solution of the crude amide in 10 ml THF was added to a slurry of 198 mg (95%, 5.0 mmol) of lithium aluminum hydride in 10 ml THF at 0° C. Gas evolution was observed. The brown slurry was warmed to 50° C. and stirred for 24.5 h. The reaction mixture was cooled to 0° C. and quenched by the sequential addition of water (300 µl), 15% aqueous sodium hydroxide solution (300 µl) and water (900 µl). The resulting slurry was warmed to room temperature and stirred for 2 h. The mixture was filtered, and the filtered solids were rinsed with hot THF. The filtrate was concentrated and purified by HPLC (Capcell Pak C$_{18}$ 5 µm, gradient of 80% A:20% B to 20% A:80% B over 45 min; A=0.5% TFA in water, B=0.5% TFA in acetonitrile) to give the title compound. $^1$H-NMR (CD$_3$OD) δ 1.02-1.12 (m, 1 H), 1.41-1.57 (m, 2 H), 1.58-1.86 (m, 4 H), 2.92 (s, 6 H), 3.42 (d, J=6.9 Hz, 2 H), 3.54 (t, J=5.0 Hz, 2 H), 3.59-3.66 (m, 1 H), 4.30 (t, J=4.9 Hz, 2 H), 6.92 (dd, J=8.9 Hz, 2.9 Hz, 2 H), 7.27 (d, J=8.9 Hz, 2 H), 7.34-7.42 (m, 2 H), 7.42-7.51 (m, 3 H), 8.26 (s, 1 H). Mass Spectrum (ESI) m/e=472.3 (M+1).

Example 38 cis-(2-Amino-cyclopentylmethyl)-{6-[4-(2-dimethylamino-ethoxy)-phenyl]-5-phenyl-7H-pyrrolo[2,3-d]pyrimidin-4-yl}-amine

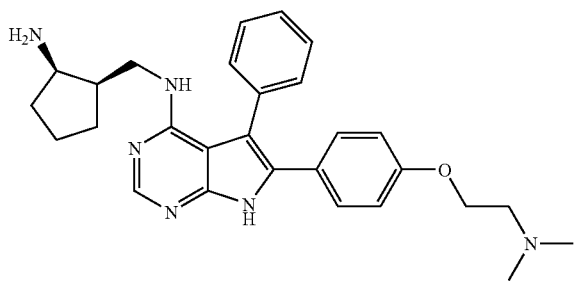

A slurry of 376 mg (1.1 mmol) of 6-[4-(2-dimethylamino-ethoxy)-phenyl]-5-phenyl-7H-pyrrolo[2,3-d]pyrimidin-4-amine (Example 34, Step A), 300 mg (1.3 mmol) of cis-2-(tert-butoxycarbonylamino)-1-cyclopentanecarboxylic acid, 274 mg (1.4 mmol) of EDC, 217 mg (1.6 mmol) of HOBt and a catalytic amount of DMAP in 5 ml DMF was stirred at room temperature for 19 h. At this time, 110 mg (0.5 mmol) of cis-2-(tert-butoxycarbonylamino)-1-cyclopentanecarboxylic acid, 274 mg (1.4 mmol) of EDC, 217 mg (1.6 mmol) of HOBt and additional catalytic DMAP were added. The brown slurry was warmed to 60° C. and stirred for 8 h. The reaction mixture was partitioned between dichloromethane (120 ml) and brine. The organic layer was washed with saturated aqueous sodium bicarbonate (1×) and water (1×), dried over $Na_2SO_4$ and filtered.

A solution of the crude amide in 6 ml CH$_2$Cl$_2$ was treated with 3 ml TFA. The brown solution was warmed to 40° C. and stirred for 25 min. The mixture was concentrated and the residue was dissolved in 10 ml THF. The solution was cooled to 0° C. and treated with 308 mg (95%, 7.7 mmol) of lithium aluminum hydride. Gas evolution was observed. The brown slurry was warmed to 50° C. and stirred for 20.5 h. The reaction mixture was cooled to 0° C. and quenched by the sequential addition of water (310 µl), 15% aqueous sodium hydroxide solution (310 µl) and water (930 µl). The resulting slurry was warmed to room temperature and stirred for 2 h. The mixture was filtered, and the filtered solids were rinsed with hot THF. The residue was purified by chromatography on silica gel (CH$_2$Cl$_2$:MeOH:NH$_4$OH, 95:5:1 grading to CH$_2$Cl$_2$:MeOH:NH$_4$OH, 90:10:1) followed by HPLC (Capcell Pak C$_{18}$ 5 µm, gradient of 80% A:20% B to 20% A:80% B over 45 min; A=0.5% TFA in water, B=0.5% TFA in acetonitrile) to give the title compound. $^1$H-NMR (CD$_3$OD) δ 1.20-1.29 (m, 1 H), 1.63-1.85 (m, 4 H), 2.02-2.11 (m, 1 H), 2.13-2.22 (m, 1 H), 2.96 (s, 6 H), 3.18-3.26 (m, 1 H), 3.44 (dd, J=13.6 Hz, 8.8 Hz, 1 H), 3.58 (t, J=4.9 Hz, 2 H), 3.76 (dd, J=13.6 Hz, 4.7 Hz, 1 H), 4.11 (t, J=5.2 Hz, 2 H), 6.97 (dd, J=8.8 Hz, 2.9 Hz, 2 H), 7.33 (d, J=8.8 Hz, 2 H), 7.42-7.47 (m, 2 H), 7.49-7.56 (m, 3 H), 8.44 (s, 1 H). Mass Spectrum (ESI) m/e=471.3 (M+1).

Example 39 cis-N-[2-({6-[4-(2-Dimethylamino-ethoxy)-phenyl]-5-phenyl-7H-pyrrolo[2,3-d]pyrimidin-4-ylamino}-methyl)-cyclopentyl]-methanesulfonamide

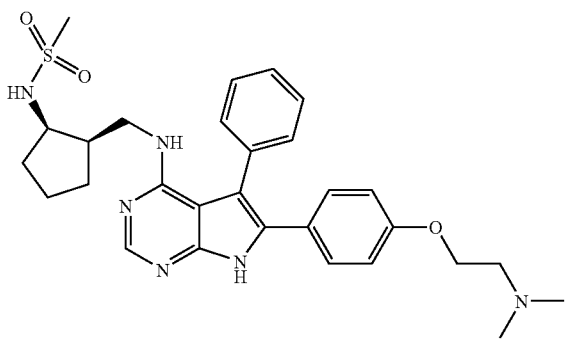

A solution of 33 mg (0.07 mmol) of cis-(2-amino-cyclopentylmethyl)-{6-[4-(2-dimethylamino-ethoxy)-phenyl]-5-phenyl-7H-pyrrolo[2,3-d]pyrimidin-4-yl}-amine (Example 38) in 2.5 ml dichloromethane was cooled to 0° C. and treated with 20 µl (0.1 mmol) of Et$_3$N and 9 µl (0.1 mmol) of MsCl. The yellow solution was warmed to room temperature and stirred for 2 h. The reaction mixture was quenched with water (50 µl) and concentrated. The residue was purified by HPLC (Capcell Pak C$_{18}$ 5 µm, gradient of 80% A:20% B to 20% A:80% B over 45 min; A=0.5% TFA in water, B=0.5% TFA in acetonitrile) to give the title compound. $^1$H-NMR (CD$_3$OD) δ 0.97-1.06 (m, 1 H), 1.46-1.59 (m, 2 H), 1.58-1.71 (m, 2 H), 1.81-1.92 (m, 1 H), 1.99-2.07 (m, 1 H), 2.88 (s, 3 H), 2.96 (s, 6 H), 3.16-3.25 (m, 1 H), 3.44 (dd, J=13.0 Hz, 6.5 Hz, 1 H), 3.57 (t, J=4.8 Hz, 2 H), 3.66 (dd, J=13.0 Hz, 5.0 Hz, 1 H), 4.33 (t, J=4.8 Hz, 2 H), 6.96 (d, J=8.5 Hz, 2 H), 7.32 (dd, J=8.5 Hz, 7.0 Hz, 2 H), 7.41-7.56 (m, 5 H), 8.30 (s, 1 H). Mass Spectrum (ESI) m/e=549.3 (M+1).

Example 40 trans-(2-Amino-cyclopentylmethyl)-{6-[4-(2-dimethylamino-ethoxy)-phenyl]-5-phenyl-7H-pyrrolo[2,3-d]pyrimidin-4-yl}-amine

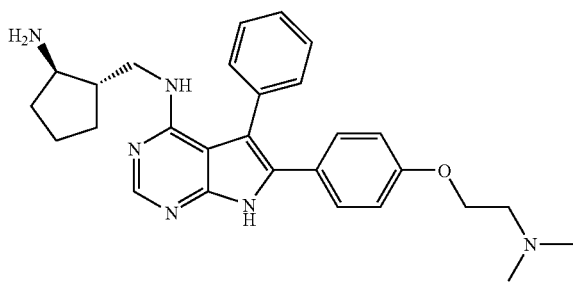

A slurry of 352 mg (0.9 mmol) of 6-[4-(2-dimethylamino-ethoxy)-phenyl]-5-phenyl-7H-pyrrolo[2,3-d]pyrimidin-4-amine (Example 34, Step A), 366 mg (1.6 mmol) of trans-2-(tert-butoxycarbonylamino)-1-cyclopentanecarboxylic acid, 471 mg (12.5 mmol) of EDC, 380 mg (2.8 mmol) of HOBt and a catalytic amount of DMAP in 5 ml DMF was stirred at 60° C. for 14 h. The reaction mixture was partitioned between dichloromethane (120 ml) and brine. The organic layer was washed with saturated aqueous sodium bicarbonate (1×) and water (1×), dried over Na$_2$SO$_4$ and filtered.

A solution of the crude amide in 6 ml CH$_2$Cl$_2$ was treated with 3 ml TFA. The brown solution was warmed to 40° C. and stirred for 20 min. The mixture was concentrated and the residue was dissolved in 10 ml THF. The solution was cooled to 0° C. and treated with 267 mg (95%, 6.7 mmol) of lithium aluminum hydride. Gas evolution was observed. The brown slurry was warmed to 50° C. and stirred for 19 h. The reaction mixture was cooled to 0° C. and quenched by the sequential addition of water (300 µl), 15% aqueous sodium hydroxide solution (300 µl) and water (900 µl). The resulting slurry was warmed to room temperature and stirred for 1.5 h. The mixture was filtered, and the filtered solids were rinsed with hot THF. The residue was purified by chromatography on silica gel (CH$_2$Cl$_2$:MeOH:NH$_4$OH, 92:8:1) to give the title compound. $^1$H-NMR (CD$_3$OD) δ 1.16-1.25 (m, 1 H), 1.59-1.82 (m, 4 H), 1.95-2.06 (m, 1 H), 2.12-2.20 (m, 1 H), 2.93 (s, 6 H), 3.15-3.22 (m, 1 H), 3.41 (dd, J=13.5 Hz, 8.5 Hz, 1 H), 3.54 (t, J=5.0 Hz, 2 H), 3.74 (dd, J=13.5 Hz, 5.0 Hz, 1 H), 4.30 (t, J=5.0 Hz, 2 H), 6.93 (d, J=8.5 Hz, 2 H), 7.29 (d, J=8.5 Hz, 2 H), 7.38-7.43 (m, 2 H), 7.44-7.52 (m, 3 H), 8.41 (s, 1 H). Mass Spectrum (ESI) m/e=471.3 (M+1).

Example 41 trans-N-[2-({6-[4-(2-Dimethylamino-ethoxy)-phenyl]-5-phenyl-7H-pyrrolo[2,3-d]pyrimidin-4-ylamino}-methyl)-cyclopentyl]-methanesulfonamide

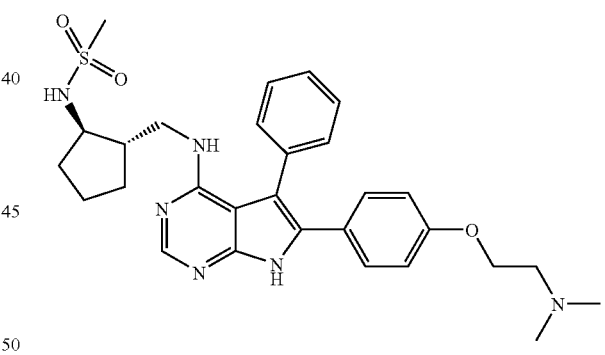

A solution of 17 mg (0.04 mmol) of trans-(2-amino-cyclopentylmethyl)-{6-[4-(2-dimethylamino-ethoxy)-phenyl]-5-phenyl-7H-pyrrolo[2,3-d]pyrimidin-4-yl}-amine (Example 40) in 2.5 ml dichloromethane was cooled to 0° C. and treated with 15 µl (0.1 mmol) of Et$_3$N and 5 µl (0.1 mmol) of MsCl. The yellow solution was warmed to room temperature and stirred for 2 h. The reaction mixture was quenched with water (40 µl) and concentrated. The residue was purified by HPLC (Capcell Pak C$_{18}$ 5 µm, gradient of 80% A:20% B to 20% A:80% B over 45 min; A=0.5% TFA in water, B=0.5% TFA in acetonitrile) to give the title compound. $^1$H-NMR (CD$_3$OD) δ 1.02-1.12 (m, 1 H), 1.51-1.64 (m, 2 H), 1.65-1.78 (m, 2 H), 1.84-1.95 (m, 1 H), 2.03-2.13 (m, 1 H), 2.92 (s, 3 H), 3.00 (s, 6 H), 3.21-3.31 (m, 1 H), 3.46 (dd, J=13.0 Hz, 6.0 Hz, 1 H), 3.61 (t, J=5.0 Hz, 2 H), 3.68 (dd, J=13.0 Hz, 5.0 Hz, 1 H), 4.37 (t, J=4.8 Hz, 2 H), 7.01 (d, J=8.5 Hz, 2 H), 7.38 (d, J=9.0 Hz, 2 H), 7.46-7.63 (m, 5 H), 8.31 (s, 1 H). Mass Spectrum (ESI) m/e=549.3 (M+1).

ACK1 Enzymatic Assay $IC_{50}$ values of inventive compounds may be assessed as follows. The ACK1 kinase assay utilizes a protein expressed in baculovirus infected Hi-5 cells (a fusion of an N-terminal (His)6 Tag with amino acids 117 to 489 of ACK1) purified by affinity chromatography on a Ni—NTA column. The substrate of for the reaction is ACK1 itself (autophosphorylation) and poly-Glutamic acid-Tyrosine (PGT (4:1), Sigma catalog #PO275). The PGT is coated to Nunc 96 well plates at 80 μg/mL overnight at 4° C. The morning after coating, the plates are washed twice, and 80 μL reaction buffer (10 mM Hepes, pH 7.6; 20 mM $MgCl_2$; 75 mM NaCl, 0.125% TWEEN20 (polyoxyethylene sorbitan monolaurate); 1 mM DTT) with 5 μM ATP are added to each well. Test compounds are added in 10 μL DMSO, and the reaction is started by addition of 10 μL kinase in assay buffer. The reaction proceeds 2 h at room temperature. Next the plates are washed four times, and the level of tyrosine phosphorylation in a given well is quantified by standard ELISA assay utilizing a phosphotyrosine antibody (PY20, Pierce). Each of the above compounds will display an $IC_{50}$ value of less than about 30 μM with respect to ACK1.

ACK1 Cell Based Assay

The ACK1 cell based assay is designed to find inhibitors of ACK1 kinase activity which would be prime candidates for the development of anticancer drugs. The assay is based on the dependence of certain transformed cell lines (e.g., C8 cells, a Ras and E1A transformed fibroblast line) on ACK1 for survival under low serum conditions, whereas other cell lines (e.g., HeLa) do not. This dependency was confirmed utilizing ACK1 specific siRNAs.

For this assay, test (C8) and control (HeLa) cell lines are seeded in 96 well tissue culture plates (BD Falcon) at a density of 2 to $4\times10^4$ in DMEM/F12 (C8) or DMEM (HeLa) with 0.125% FCS in the presence of ACK1 inhibitors (final DMSO concentration is 0.5%, all tissue culture media are from Cellgro). After 20 to 24 h incubation at 37° C. and 5% $CO_2$, cell viability is determined using the Cytotox One kit (Promega) according to the manufacturer's instructions.

As an example, the compound of example 20 was tested in the above cell assay and found to be cytotoxic to C8 cells. By contrast, the compound of example 20 had no cytotoxic effect on HeLa cells under these conditions. These results demonstrate that inventive compounds can selectively kill transformed cells and are not merely unselective cytotoxic agents. Compounds of the invention therefore will be found to possess selective cytotoxic activity against cancer cells.

LCK-Homogeneous Time Resolved Fluorescent (HTRF) Kinase Assay

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents.

The LCK HTRF assay is comprised of 10 μL of compound in 100% DMSO, 15 μL of ATP and biotinylated Gastrin, and 15 μL of LCK KD GST (225-509) for a final volume of 40 μL. The final concentration of gastrin is 1.2 μM. The final concentration of ATP is 0.5 μM (Km app=0.61M+/−0.1) and the final concentration of LCK is 250 μM. Buffer conditions are as follows: 50 mM HEPES pH 7.5, 50 mM NaCl, 20 mM MgCl, 5 mM MnCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0004 mg/mL, and europilated anti-phosphotyrosine Ab (Eu-anti-PY) at a final conc of 0.025 nM.

The assay plate is read in either a Discovery or a RubyStar. The eu-anti-PY is excited at 320 nm and emits at 615 nm to excite the SA-APC which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

Compounds of the invention having useful activity as measured by $K_i$ and $IC_{50}$ are shown in Table 2.

TABLE 2

| Ex | Structure | Name | Ack1 $K_i$ | ACK1 Cell-based $IC_{50}$ | LcK $K_i$ |
|---|---|---|---|---|---|
| 1 | 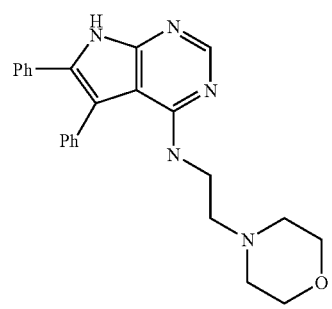 | (5,6-Diphenyl-7H-pyrrolo[2,3-d]pyrimidin-4-yl)-(2-morpholin-4-ylethyl)-amine | ++ | + | ++ |

TABLE 2-continued

| Ex | Structure | Name | Ack1 K$_i$ | ACK1 Cell-based IC$_{50}$ | LcK K$_i$ |
|---|---|---|---|---|---|
| 2 | 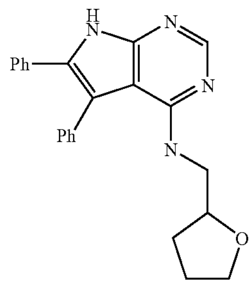 | (5,6-Diphenyl-7H-pyrrolo[2,3-d]pyrimidin-4-yl)-(tetrahydrofuran-2-ylmethyl)-amine | +++ | + | +++ |
| 3 | 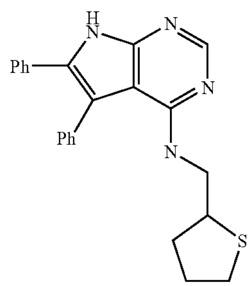 | (5,6-Diphenyl-7H-pyrrolo[2,3-d]pyrimidin-4-yl)-(tetrahydrothiophen-2-ylmethyl)-amine | ++ | + | +++ |
| 4 | 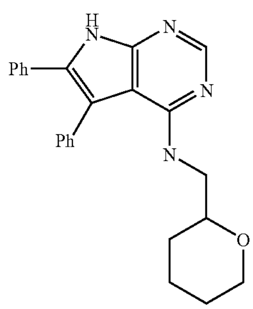 | (5,6-Diphenyl-7H-pyrrolo[2,3-d]pyrimidin-4-yl)-(tetrahydropyran-2-ylmethyl) amine | ++ | + | +++ |
| 5 | 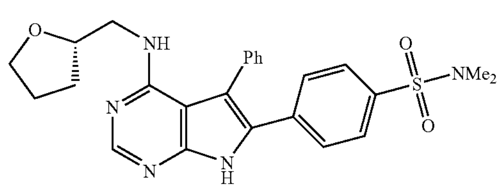 | N,N-Dimethyl-4-{5-phenyl-4-[(tetrahydro-furan-2-ylmethyl)-amino]-7H-pyrrolo[2,3-d]pyrimidin-6-yl}-benzenesulfonamide | +++ | ++ | +++ |
| — | 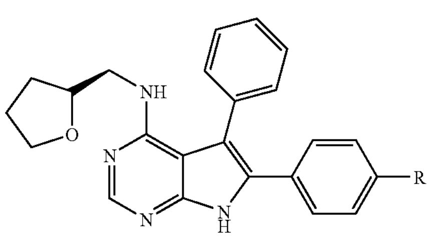 | — | — | — | — |
| 6 | R=SO$_2$NHMe | N-Methyl-4-{5-phenyl-4-[(tetrahydrofuran-2-ylmethyl)-amino]-7H-pyrrolo[2,3-d]pyrimidin-6-yl}-benzenesulfonamide | +++ | ++ | +++ |
| 7 | SO$_2$NEt$_2$ | N,N-Diethyl-4-{5-phenyl-4-[(tetrahydrofuran-2- | +++ | + | +++ |

TABLE 2-continued

| Ex | Structure | Name | Ack1 $K_i$ | ACK1 Cell-based $IC_{50}$ | LcK $K_i$ |
|---|---|---|---|---|---|
| | | ylmethyl)-amino]-7H-pyrrolo[2,3-d]pyrimidin-6-yl}-benzenesulfonamide | | | |
| 8 | 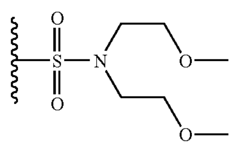 | N,N-Bis-(2-methoxyethyl)-4-{5-phenyl-4-[(tetrahydrofuran-2-ylmethyl)-amino]-7H-pyrrolo[2,3-d]pyrimidin-6-yl}-benzenesulfonamide | +++ | + | +++ |
| 9 | 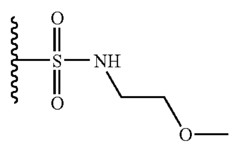 | N-(2-Methoxyethyl)-4-{5-phenyl-4-[(tetrahydrofuran-2-ylmethyl)-amino]-7H-pyrrolo[2,3-d]pyrimidin-6-yl}-benzenesulfonamide | +++ | ++ | +++ |
| 10 | 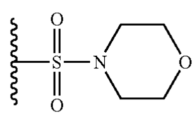 | {6-[4-(Morpholin-4-sulfonyl)-phenyl]-5-phenyl-7H-pyrrolo[2,3-d]pyrimidin-4-yl}-(tetrahydrofuran-2-ylmethyl)-amine | +++ | + | +++ |
| 11 | 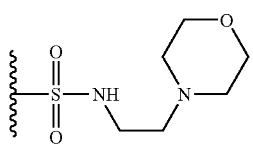 | N-(2-Morpholin-4-yl-ethyl)-4-{5-phenyl-4-[(tetrahydrofuran-2-ylmethyl)-amino]-7H-pyrrolo[2,3-d]pyrimidin-6-yl}-benzenesulfonamide | +++ | ++ | +++ |
| 12 | 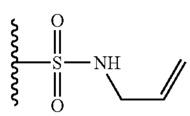 | N-Allyl-4-{5-phenyl-4-[(tetrahydro-furan-2-ylmethyl)-amino]-7H-pyrrolo[2,3-d]pyrimidin-6-yl}-benzenesulfonamide | +++ | + | +++ |
| 13 | 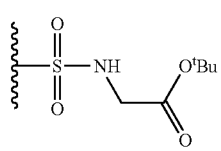 | (4-{5-Phenyl-4-[(tetrahydrofuran-2-ylmethyl)-amino]-7H-pyrrolo[2,3-d]pyrimidin-6-yl}-benzenesulfonyl-amino)-acetic acid tert-butyl ester | ++ | + | ++ |
| 14 | 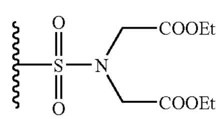 | [Ethoxycarbonyl-methyl-(4-{5-phenyl-4-[(tetrahydrofuran-2-ylmethyl)-amino]-7H-pyrrolo[2,3-d]pyrimidin-6-yl}-benzenesulfonyl)-amino]-acetic acid ethyl ester | +++ | + | ++ |
| 15 | 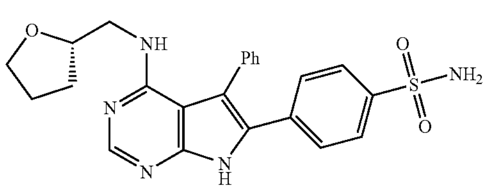 | 4-{5-Phenyl-4-[(tetrahydrofuran-2-ylmethyl)-amino]-7H-pyrrolo[2,3-d]pyrimidin-6-yl}-benzenesulfonamide | +++ | + | ++ |

TABLE 2-continued

| Ex | Structure | Name | Ack1 $K_i$ | ACK1 Cell-based $IC_{50}$ | LcK $K_i$ |
|---|---|---|---|---|---|
| 16 | 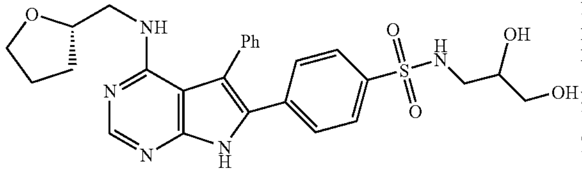 | N-(2,3-dihydroxy-propyl)-4-{5-phenyl-4-[(tetrahydrofuran-2-ylmethyl)-amino]-7H-pyrrolo[2,3-d]pyrimidin-6-yl}-benzenesulfonamide | +++ | + | +++ |
| 17 | 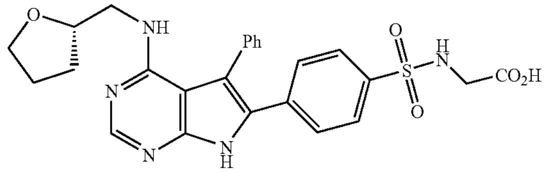 | 4-[(Tetrahydrofuran-2-ylmethyl)-amino]-7H-pyrrolo[2,3-d]pyrimidin-6-yl}-benzenesulfonyl-amino)-acetic acid | +++ | + | ++ |
| 18 | 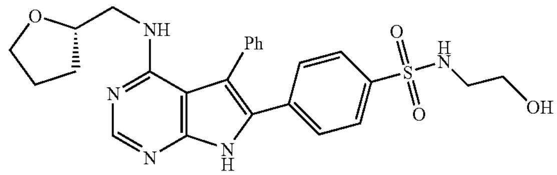 | N-(2-Hydroxy-ethyl)-4-{5-phenyl-4-[(tetrahydr-furan-2-ylmethyl)-amino]-7H-pyrrolo[2,3-d]pyrimidin-6-yl}-benzenesulfonamide | +++ | + | +++ |
| 19 | 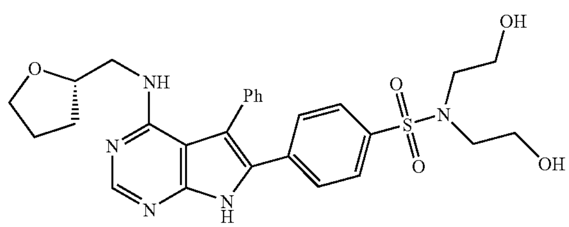 | N,N-Bis-(2-hydroxyethyl)-4-{5-phenyl-4-[(tetrahydro-furan-2-ylmethyl)-amino]-7H-pyrrolo[2,3-d]pyrimidin-6-yl}-benzenesulfonamide | +++ | + | +++ |
| 20 | 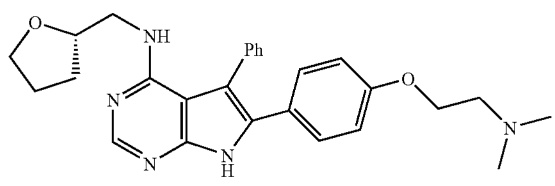 | {6-[4-(2-Dimethylamino-ethoxy)-phenyl]-5-phenyl-7H-pyrrolo[2,3-d]pyrimidin-4-yl}-(tetrahydro-furan-2-ylmethyl)-amine | +++ | ++ | +++ |
| | | | — | — | — |
| 21 | 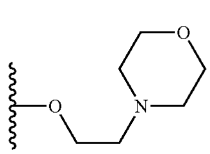 | {6-[4-(2-Morpholin-4-yl-ethoxy)-phenyl]-5-phenyl-7H-pyrrolo[2,3-d]pyrimidin-4-yl}-(tetrahydro-furan-2-ylmethyl)-amine | +++ | ++ | +++ |

TABLE 2-continued

| Ex | Structure | Name | Ack1 $K_i$ | ACK1 Cell-based $IC_{50}$ | LcK $K_i$ |
|---|---|---|---|---|---|
| 22 | (structure: ~O-CH2CH2-pyrrolidin-1-yl) | {5-Phenyl-6-[4-(2-pyrrolidin-1-yl-ethoxy)-phenyl]-7H-pyrrolo[2,3-d]pyrimidin-4-yl}-(tetrahydrofuran-2-ylmethyl)-amine | +++ | ++ | +++ |
| 23 | (structure: ~O-CH2CH2-N-pyrrolidin-2-one) | 1-[2-(4-{5-Phenyl-4-[(tetrahydrofuran-2-ylmethyl)-amino]-7H-pyrrolo[2,3-d]pyrimidin-6-yl}-phenoxy)-ethyl]-pyrrolidin-2-one | +++ | ++ | +++ |
| 24 | (structure: ~O-CH2CH2-(1-methylpyrrolidin-2-yl)) | (6-{4-[2-(1-Methyl-pyrrolidin-2-yl)-ethoxy]-phenyl}-5-phenyl-7H-pyrrolo[2,3-d]pyrimidin-4-yl)-(tetrahydrofuran-2-ylmethyl)-amine | ++ | + | ++ |
| 25 | (full structure with O-CH2-CN) | (4-{5-Phenyl-4-[(tetrahydrofuran-2-ylmethyl)-amino]-7H-pyrrolo[2,3-d]pyrimidin-6-yl}-phenoxy)-acetonitrile | +++ | ++ | ++ |
| 26 | (full structure with C(O)NHMe) | N-Methyl-4-{5-phenyl-4-[(tetrahydrofuran-2-ylmethyl)-amino]-7H-pyrrolo[2,3-d]pyrimidin-6-yl}-benzamide | +++ | ++ | +++ |
| — | (core structure with R) | — | — | — | — |
| 27 | (structure: ~C(O)N(Me)2) | N,N-Dimethyl-4-{5-phenyl-4-[(tetrahydrofuran-2-ylmethyl)-amino]-7H-pyrrolo[2,3-d]pyrimidin-6-yl}-benzamide | +++ | ++ | +++ |
| 28 | (structure: ~C(O)-morpholine) | Morpholin-4-yl-(4-{5-phenyl-4-[(tetrahydrofuran-2-ylmethyl)-amino]-7H-pyrrolo[2,3-d]pyrimidin-6-yl}-phenyl)-methanone | +++ | ++ | + |

TABLE 2-continued

| Ex | Structure | Name | Ack1 $K_i$ | ACK1 Cell-based $IC_{50}$ | LcK $K_i$ |
|---|---|---|---|---|---|
| 29 | 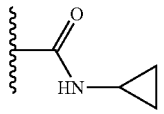 | N-Cyclopropyl-4-{5-phenyl-4-[(tetrahydrofuran-2-ylmethyl)-amino]-7H-pyrrolo[2,3-d]pyrimidin-6-yl}-benzamide | +++ | ++ | +++ |
| 30 | 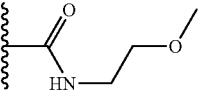 | N-(2-Methoxyethyl)-4-{5-phenyl-4-[(tetrahydrofuran-2-ylmethyl)-amino]-7H-pyrrolo[2,3-d]pyrimidin-6-yl}-benzamide | +++ | ++ | +++ |
| 31 | 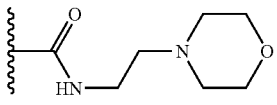 | N-(2-Morpholin-4-yl-ethyl)-4-{5-phenyl-4-[(tetrahydrofuran-2-ylmethyl)-amino]-7H-pyrrolo[2,3-d]pyrimidin-6-yl}-benzamide | +++ | + | +++ |
| 32 | 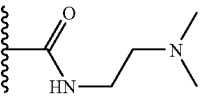 | N-(2-Dimethylamino-ethyl)-4-{5-phenyl-4-[(tetrahydrofuran-2-ylmethyl)-amino]-7H-pyrrolo[2,3-d]pyrimidin-6-yl}-benzamide | +++ | ++ | +++ |
| 33 | 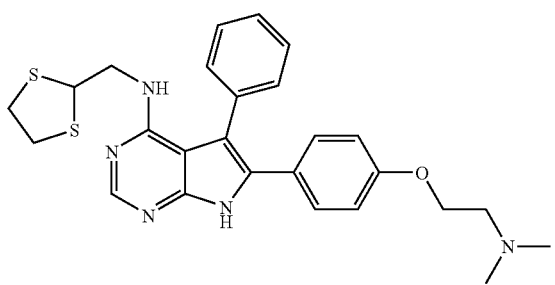 | {6-[4-(2-Dimethylamino-ethoxy)-phenyl]-5-phenyl-7H-pyrrolo[2,3-d]pyrimidin-4-yl}-[1,3]dithiolan-2-ylmethyl-amine | +++ | +++ | +++ |
| 34 | 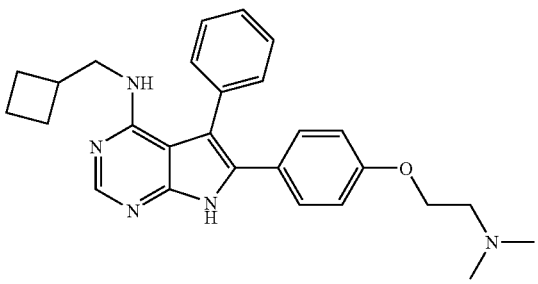 | Cyclobutylmethyl-{6-[4-(2-dimethylamino-ethoxy)-phenyl]-5-phenyl-7H-pyrrolo[2,3-d]pyrimidin-4-yl}-amine | ++ | + | +++ |

TABLE 2-continued

| Ex | Structure | Name | Ack1 $K_i$ | ACK1 Cell-based $IC_{50}$ | LcK $K_i$ |
|---|---|---|---|---|---|
| 35 | 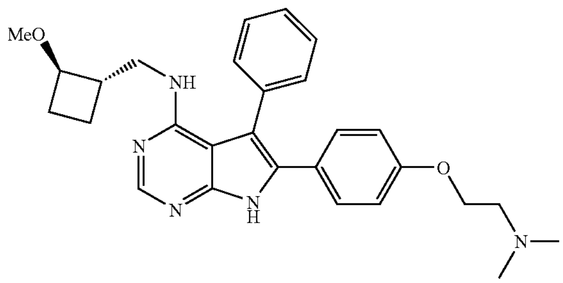 | trans-{6-[4-(2-Dimethylamino-ethoxy)-phenyl]-5-phenyl-7H-pyrrolo[2,3-d]pyrimidin-4-yl}-(2-methoxy-cyclobutylmethyl)-amine | ++ | + | +++ |
| 36 | 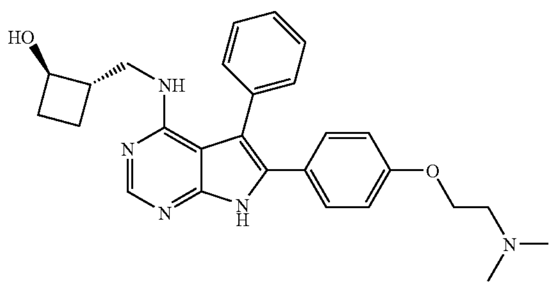 | trans-2-({6-[4-(2-Dimethylamino-ethoxy)-phenyl]-5-phenyl-7H-pyrrolo[2,3-d]pyrimidin-4-ylamino}-methyl)-cyclobutanol | ++ | + | nd |
| 37 | 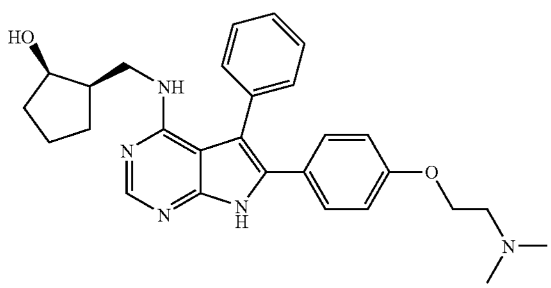 | cis-2-({6-[4-(2-Dimethylamino-ethoxy)-phenyl]-5-phenyl-7H-pyrrolo[2,3-d]pyrimidin-4-ylamino}-methyl)-cyclopentanol | ++ | + | +++ |
| 38 | 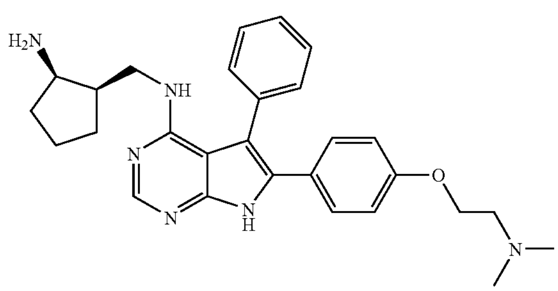 | cis-(2-Amino-cyclopentylmethyl)-{6-[4-(2-dimethylamino-ethoxy)-phenyl]-5-phenyl-7H-pyrrolo[2,3-d]pyrimidin-4-yl}-amine | + | + | ++ |
| 39 | 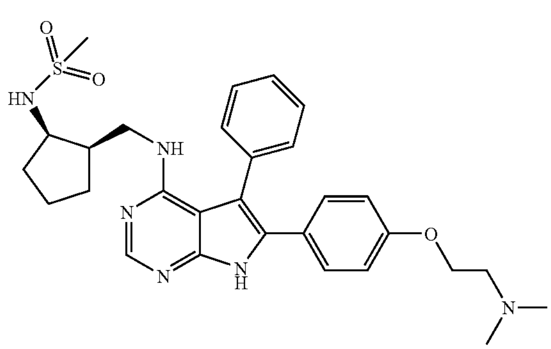 | cis-N-[2-({6-[4-(2-Dimethylamino-ethoxy)-phenyl]-5-phenyl-7H-pyrrolo[2,3-d]pyrimidin-4-ylamino}-methyl)-cyclopentyl]-methanesulfonamide | + | + | +++ |

TABLE 2-continued

| Ex | Structure | Name | Ack1 $K_i$ | ACK1 Cell-based $IC_{50}$ | LcK $K_i$ |
|---|---|---|---|---|---|
| 40 | 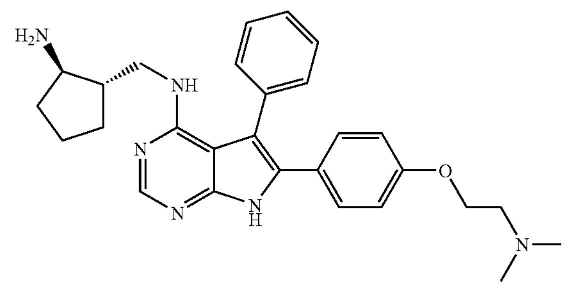 | trans-(2-Amino-cyclopentylmethyl)-{6-[4-(2-dimethylamino-ethoxy)-phenyl]-5-phenyl-7H-pyrrolo[2,3-d]pyrimidin-4-yl}-amine | + | + | +++ |
| 41 | 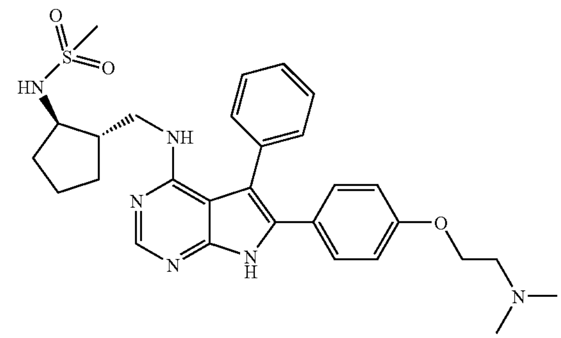 | trans-N-[2-({6-[4-(2-Dimethylamino-ethoxy)-phenyl]-5-phenyl-7H-pyrrolo[2,3-d]pyrimidin-4-ylamino}-methyl)-cyclopentyl]-methanesulfonamide | ++ | + | +++ |

Legend:
"+" represents: IC50 value > 0.1 μM
"++" represents: 0.1 μM > IC50 value > 0.01 μM
"+++" represents: IC50 value < 0.01 μM It is understood that the invention is not limited to the embodiments set forth herein for illustration, but embraces all such forms thereof as come within the scope of the following claims.

What is claimed is:

1. A compound having the structure:

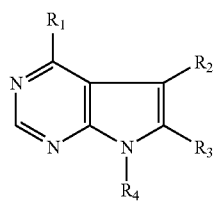

including stereoisomers thereof, tautomers thereof, and pharmaceutically acceptable salts thereof, wherein:

$R_1$ is —$OR_5$, —$SR_5$, or —$NHR_5$;

$R_2$ and $R_3$ independently are aryl, substituted aryl, heteroaryl, substituted heteroaryl, cycloalkyl, substituted cycloalkyl, cycloheteroalkyl, substituted cycloheteroalkyl, arylalkyl, substituted arylalkyl, (heteroaryl)alkyl, substituted (heteroaryl)alkyl, (cycloalkyl)alkyl, substituted (cycloalkyl)alkyl, (cycloheteroalkyl)alkyl, or substituted (cycloheteroalkyl)alkyl;

$R_4$ is hydrogen, alkyl, substituted alkyl, alkylcarbonyl, substituted alkylcarbonyl, arylcarbonyl, substituted arylcarbonyl, arylalkylcarbonyl, substituted arylalkylcarbonyl, alkylsulfonyl, substituted alkylsulfonyl, arylsulfonyl, substituted arylsulfonyl, arylalkylsulfonyl, substituted arylalkylsulfonyl, trialkylsilyl, substituted trialkylsilyl, triarylalkylsilyl, substituted triarylalkylsilyl, formyl, diarylthiophosphinyl, or substituted diarylthiophosphinyl; and $R_5$ is a (cycloheteroalkyl)alkyl or substituted (cycloheteroalkyl)alkyl moiety, wherein the cycloheteroalkyl portion of said moiety is a saturated ring.

2. The compound of claim 1, wherein $R_1$ is —$NHR_5$.

3. The compound of claim 2, wherein $R_2$ and $R_3$ independently are aryl, substituted aryl, heteroaryl, or substituted heteroaryl.

4. The compound of claim 3, wherein $R_2$ and $R_3$ independently are aryl or substituted aryl.

5. The compound of claim 4, wherein $R_2$ and $R_3$ independently are phenyl or substituted phenyl.

6. The compound of claim 5, wherein $R_2$ and $R_3$ are phenyl.

7. The compound of claim 5, wherein $R_2$ is phenyl.

8. The compound of claim 7, wherein $R_3$ is phenyl substituted with a moiety selected from the group consisting of: alkylaminosulfonyl, dialkylaminosulfonyl, (heterocycloalkyl)alkylaminosulfonyl, di(alkyloxyalkyl)aminosulfonyl, alkyloxyalkylaminosulfonyl, N-morpholinosulfonyl, N-morpholinoalkylaminosulfonyl, carboxylakylaminosulfonyl, alkyloxycarbonylalkylaminosulfonyl, alkylaminocarbonyl, dialkylaminocarbonyl, (heterocycloalkyl)alkylaminocarbonyl, di(alkyloxyalkyl)aminocarbonyl, alkyloxyalkylaminocarbonyl, N-morpholinocarbonyl, N-morpholinoalkylaminocarbonyl, carboxylakylaminocarbonyl, alkyloxycarbonylalkylaminocarbonyl, cycloalkylamioncarbonyl, alkyloxy, alkylaminoalkyloxy, (dialkylamino)alkyloxy, N-morpholinoalkyloxy, or N-azacycloalkylalkyloxy, wherein each of the foregoing substituents is itself optionally substituted.

9. The compound of claim 8, wherein $R_5$ is tetrahydrofuranylalkyl.

10. The compound of claim 9, wherein $R_5$ is (tetrahydrofuran-2-yl)methyl.

11. A compound having the structure:

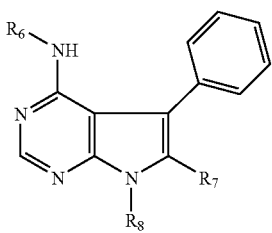

including stereoisomers thereof, tautomers thereof, and pharmaceutically acceptable salts thereof, wherein:

$R_6$ is a (cycloheteroalkyl)methyl moiety, wherein the cycloheteroalkyl portion of said moiety is a saturated 5- or 6-membered heteroalkyl ring containing at least one oxygen or sulfur heteroatom;

$R_7$ is aryl or heteroaryl, each optionally substituted with alkylaminosulfonyl, dialkylaminosulfonyl, (heterocycloalkyl)alkylaminosulfonyl, di(alkyloxyalkyl)aminosulfonyl, alkyloxyalkylaminosulfonyl, N-morpholinosulfonyl, N-morpholinoalkylaminosulfonyl, carboxylakylaminosulfonyl, alkyloxycarbonylalkylaminosulfonyl, alkylaminocarbonyl, dialkylaminocarbonyl, (heterocycloalkyl)alkylaminocarbonyl, di(alkyloxyalkyl)aminocarbonyl, alkyloxyalkylaminocarbonyl, N-morpholinocarbonyl, N-morpholinoalkylaminocarbonyl, carboxylakylaminocarbonyl, alkyloxycarbonylalkylaminocarbonyl, cycloalkylamioncarbonyl, alkyloxy, alkylaminoalkyloxy, (dialkylamino)alkyloxy, N-morpholinoalkyloxy, or N-azacycloalkylalkyloxy, wherein each of the foregoing optional substituents is itself optionally substituted; and $R_8$ is hydrogen, alkyl, substituted alkyl, alkylcarbonyl, substituted alkylcarbonyl, arylcarbonyl, substituted arylcarbonyl, arylalkylcarbonyl, substituted arylalkylcarbonyl, alkylsulfonyl, substituted alkylsulfonyl, arylsulfonyl, substituted arylsulfonyl, arylalkylsulfonyl, substituted arylalkylsulfonyl, trialkylsilyl, substituted trialkylsilyl, triarylalkylsilyl, substituted triarylalkylsilyl, formyl, diarylthiophosphinyl, or substituted diarylthiophosphinyl.

12. The compound of claim 11, wherein $R_7$ is aryl.

13. The compound of claim 12, wherein $R_7$ is phenyl.

14. The compound of claim 12, wherein $R_6$ is tetrahydrofuranylmethyl.

15. The compound of claim 13, wherein $R_6$ is (tetrahydrofuran-2-yl)methyl.

16. The compound of claim 14, wherein $R_6$ is ((S)-tetrahydrofuran-2-yl)methyl.

17. The compound of claim 11, wherein $R_6$ is tetrahydrofuranylmethyl.

18. The compound of claim 17, wherein $R_6$ is (tetrahydrofuran-2-yl)methyl.

19. The compound of claim 18, wherein $R_6$ is ((S)-tetrahydrofuran-2-yl)methyl.

20. The compound of claim 1, wherein said compound is selected from the group consisting of:
- (5,6-Diphenyl-7H-pyrrolo[2,3-d]pyrimidin-4-yl)-(2-morpholin-4-ylethyl)-amine,
- (5,6-Diphenyl-7H-pyrrolo[2,3-d]pyrimidin-4-yl)-(tetrahydrofuran-2-ylmethyl)-amine,
- (5,6-Diphenyl-7H-pyrrolo[2,3-d]pyrimidin-4-yl)-(tetrahydrothiophen-2-ylmethyl)-amine,
- (5,6-Diphenyl-7H-pyrrolo[2,3-d]pyrimidin-4-yl)-(tetrahydropyran-2-ylmethyl) amine,
- N,N-Dimethyl-4-{5-phenyl-4-[(tetrahydro-furan-2-ylmethyl)-amino]-7H-pyrrolo[2,3-d]pyrimidin-6-yl}-benzenesulfonamide,
- N-Methyl-4-{5-phenyl-4-[(tetrahydrofuran-2-ylmethyl)-amino]-7H-pyrrolo[2,3-d]pyrimidin-6-yl}-benzenesulfonamide,
- N,N-Diethyl-4-{5-phenyl-4-[(tetrahydrofuran-2-ylmethyl)-amino]-7H-pyrrolo[2,3-d]pyrimidin-6-yl}-benzenesulfonamide,
- N,N-Bis-(2-methoxyethyl)-4-{5-phenyl-4-[(tetrahydrofuran-2-ylmethyl)-amino]-7H-pyrrolo[2,3-d]pyrimidin-6-yl}-benzenesulfonamide,
- N-(2-Methoxyethyl)-4-{5-phenyl-4-[(tetrahydrofuran-2-ylmethyl)-amino]-7H-pyrrolo[2,3-d]pyrimidin-6-yl}-benzenesulfonamide,
- {6-[4-(Morpholin-4-sulfonyl)-phenyl]-5-phenyl-7H-pyrrolo[2,3-d]pyrimidin-4-yl}-(tetrahydrofuran-2-ylmethyl)-amine,
- N-(2-Morpholin-4-yl-ethyl)-4-{5-phenyl-4-[(tetrahydrofuran-2-ylmethyl)-amino]-7H-pyrrolo[2,3-d]pyrimidin-6-yl}-benzenesulfonamide,
- N-Allyl-4-{5-phenyl-4-[(tetrahydro-furan-2-ylmethyl)-amino]-7H-pyrrolo[2,3-d]pyrimidin-6-yl}-benzenesulfonamide,
- (4-{5-Phenyl-4-[(tetrahydrofuran-2-ylmethyl)-amino]-7H-pyrrolo[2,3-d]pyrimidin-6-yl}-benzenesulfonylamino)-acetic acid tert-butyl ester,
- [Ethoxycarbonylmethyl-(4-{5-phenyl-4-[(tetrahydrofuran-2-ylmethyl)-amino]-7H-pyrrolo[2,3-d]pyrimidin-6-yl}-benzenesulfonyl)-amino]-acetic acid ethyl ester,
- 4-{5-Phenyl-4-[(tetrahydrofuran-2-ylmethyl)-amino]-7H-pyrrolo[2,3-d]pyrimidin-6-yl}.

21. A method for treating prostate cancer, lung cancer, or ovarian cancer in an animal, comprising administering to such animal a therapeutically effective amount of a compound of claim 1.

22. A pharmaceutical composition comprising a therapeutically effective amount of a compound of claim 1 in a pharmaceutically effective carrier.

* * * * *